(12) United States Patent
Dewey et al.

(10) Patent No.: US 11,807,859 B2
(45) Date of Patent: *Nov. 7, 2023

(54) ALTERATION OF TOBACCO ALKALOID CONTENT THROUGH MODIFICATION OF SPECIFIC CYTOCHROME P450 GENES

(71) Applicants: North Carolina State University, Raleigh, NC (US); University of Kentucky Research Foundation, Lexington, KY (US)

(72) Inventors: Ralph E. Dewey, Apex, NC (US); Balazs Siminszky, Neuchatel (CH); Steven W. Bowen, Raleigh, NC (US); Lily Gavilano, Raleigh, NC (US)

(73) Assignees: North Carolina State University, Raleigh, NC (US); University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/653,059

(22) Filed: Mar. 1, 2022

(65) Prior Publication Data

US 2022/0275388 A1 Sep. 1, 2022

Related U.S. Application Data

(60) Continuation of application No. 16/860,542, filed on Apr. 28, 2020, now Pat. No. 11,293,031, which is a continuation of application No. 15/631,873, filed on Jun. 23, 2017, now Pat. No. 10,687,490, which is a continuation of application No. 14/950,155, filed on Nov. 24, 2015, now Pat. No. 10,292,353, which is a continuation of application No. 13/361,235, filed on Jan. 30, 2012, now Pat. No. 9,228,195, and a continuation of application No. 13/361,159, filed on Jan. 30, 2012, now Pat. No. 9,228,194, which is a division of application No. 12/269,531, filed on Nov. 12, 2008, now Pat. No. 8,124,851, said application No. 13/361,235 is a division of application No. 12/269,531, filed on Nov. 12, 2008, now Pat. No. 8,124,851.

(60) Provisional application No. 60/987,243, filed on Nov. 12, 2007.

(51) Int. Cl.
*C12N 15/82* (2006.01)
*A01H 1/06* (2006.01)
*C12N 9/02* (2006.01)
*C12Q 1/6895* (2018.01)

(52) U.S. Cl.
CPC .......... *C12N 15/8243* (2013.01); *A01H 1/06* (2013.01); *C12N 9/0073* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,693,976 A | 9/1987 | Schilperoort et al. |
| 4,732,856 A | 3/1988 | Federoff |
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller et al. |
| 5,149,645 A | 9/1992 | Hoekema et al. |
| 5,159,135 A | 10/1992 | Umbeck |
| 5,177,010 A | 1/1993 | Goldman et al. |

(Continued)

FOREIGN PATENT DOCUMENTS

| | | |
|---|---|---|
| EP | 0 120 516 A3 | 10/1984 |
| EP | 0 267 159 A3 | 5/1988 |

(Continued)

OTHER PUBLICATIONS

U.S. Appl. No. 16/860,542, filed Apr. 28, 2020, U.S. Pat. No. 11/293,031, Issued.

(Continued)

*Primary Examiner* — Weihua Fan
(74) *Attorney, Agent, or Firm* — Alston & Bird LLP

(57) ABSTRACT

Compositions and methods for reducing the level of nornicotine and N'-nitrosonornicotine (NNN) in *Nicotiana* plants and plant parts thereof are provided. The compositions comprise isolated polynucleotides and polypeptides for cytochrome P450s that are involved in the metabolic conversion of nicotine to nornicotine in these plants. Expression cassettes, vectors, plants, and plant parts thereof comprising inhibitory sequences that target expression or function of the disclosed cytochrome P450 polypeptides are also provided. Methods for the use of these novel sequences to inhibit expression or function of cytochrome P450 polypeptides involved in this metabolic conversion are also provided. The methods find use in the production of tobacco products that have reduced levels of nornicotine and its carcinogenic metabolite, NNN, and thus reduced carcinogenic potential for individuals consuming these tobacco products or exposed to secondary smoke derived from these products.

21 Claims, 4 Drawing Sheets
Specification includes a Sequence Listing.

(56) References Cited

U.S. PATENT DOCUMENTS

| | | | |
|---|---|---|---|
| 5,231,019 A | 7/1993 | Paszkowski et al. | |
| 5,302,523 A | 4/1994 | Coffee et al. | |
| 5,352,605 A | 10/1994 | Fraley et al. | |
| 5,378,619 A | 1/1995 | Rogers | |
| 5,384,253 A | 1/1995 | Krzyzek et al. | |
| 5,463,174 A | 10/1995 | Moloney et al. | |
| 5,464,763 A | 11/1995 | Schilperoort et al. | |
| 5,464,765 A | 11/1995 | Coffee et al. | |
| 5,469,976 A | 11/1995 | Burchell | |
| 5,472,869 A | 12/1995 | Krzyzek et al. | |
| 5,583,021 A | 12/1996 | Dougherty et al. | |
| 5,595,733 A | 1/1997 | Carswell et al. | |
| 5,614,399 A | 3/1997 | Quail et al. | |
| 5,641,664 A | 6/1997 | D'Halluin et al. | |
| 5,668,295 A | 9/1997 | Wahab et al. | |
| 5,679,558 A | 10/1997 | Göbel et al. | |
| 5,684,241 A | 11/1997 | Nakatani et al. | |
| 5,712,135 A | 1/1998 | D'Halluin et al. | |
| 5,713,376 A | 2/1998 | Berger | |
| 5,766,900 A | 6/1998 | Shillito et al. | |
| 5,929,304 A | 7/1999 | Radin et al. | |
| 6,002,070 A | 12/1999 | D'Halluin et al. | |
| 6,074,877 A | 6/2000 | D'Halluin et al. | |
| 6,907,887 B2 | 6/2005 | Conkling | |
| 6,953,040 B2 | 10/2005 | Atchley et al. | |
| 7,032,601 B2 | 4/2006 | Atchley et al. | |
| 7,700,834 B2 | 4/2010 | Xu et al. | |
| 7,700,851 B2 | 4/2010 | Xu | |
| 7,812,227 B2 | 10/2010 | Xu | |
| 7,855,318 B2 | 12/2010 | Xu | |
| 7,884,263 B2 | 2/2011 | Dewey et al. | |
| 8,058,504 B2 | 11/2011 | Xu | |
| 8,124,851 B2 | 2/2012 | Dewey et al. | |
| 8,319,011 B2 | 11/2012 | Xu et al. | |
| 9,228,194 B2 | 1/2016 | Dewey et al. | |
| 9,228,195 B2 | 1/2016 | Dewey et al. | |
| 9,247,706 B2 | 2/2016 | Dewey et al. | |
| 10,292,353 B2* | 5/2019 | Dewey | A01H 1/06 |
| 11,293,031 B2* | 4/2022 | Dewey | A01H 6/823 |
| 2002/0042934 A1 | 4/2002 | Staub et al. | |
| 2004/0103449 A1 | 5/2004 | Xu | |
| 2004/0111759 A1 | 6/2004 | Xu | |
| 2004/0117869 A1 | 6/2004 | Xu | |
| 2004/0162420 A1 | 8/2004 | Xu | |
| 2004/0250821 A1 | 12/2004 | Perfetti et al. | |
| 2005/0132444 A1 | 6/2005 | Xu | |
| 2005/0160493 A9 | 7/2005 | Ratcliffe et al. | |
| 2005/0178398 A1 | 8/2005 | Breslin et al. | |
| 2005/0223442 A1 | 10/2005 | Xu | |
| 2005/0244521 A1 | 11/2005 | Strickland et al. | |
| 2006/0037096 A1 | 2/2006 | Xu | |
| 2006/0037623 A1 | 2/2006 | Lawrence | |
| 2006/0041949 A1 | 2/2006 | Xu | |
| 2006/0157072 A1 | 7/2006 | Albino et al. | |
| 2006/0185686 A1 | 8/2006 | Lawrence | |
| 2006/0191548 A1 | 8/2006 | Strickland et al. | |
| 2007/0149408 A1 | 6/2007 | Thomas et al. | |
| 2007/0199097 A1 | 8/2007 | Xu et al. | |
| 2007/0292871 A1 | 12/2007 | Xu | |
| 2008/0076126 A1 | 3/2008 | Xu | |
| 2008/0202541 A1 | 8/2008 | Dewey et al. | |
| 2008/0245377 A1 | 10/2008 | Marshall et al. | |
| 2009/0119788 A1 | 5/2009 | Mallman et al. | |
| 2009/0205072 A1 | 8/2009 | Dewey et al. | |
| 2010/0218270 A1 | 8/2010 | Xu et al. | |
| 2010/0235938 A1 | 9/2010 | Xu et al. | |
| 2010/0235945 A1 | 9/2010 | Xu et al. | |
| 2010/0235952 A1 | 9/2010 | Xu et al. | |
| 2011/0048437 A1 | 3/2011 | Xu | |
| 2011/0078817 A1 | 3/2011 | Xu | |
| 2011/0174322 A1 | 7/2011 | Dewey et al. | |
| 2011/0263328 A1 | 10/2011 | Yamashita et al. | |

FOREIGN PATENT DOCUMENTS

| | | |
|---|---|---|
| EP | 0 292 435 B1 | 11/1988 |
| EP | 0 320 500 B1 | 6/1989 |
| EP | 0 116 718 B1 | 5/1990 |
| EP | 0 159 418 B1 | 5/1990 |
| EP | 0 176 112 B1 | 5/1990 |
| EP | 0 131 624 B1 | 9/1992 |
| EP | 0 627 752 B1 | 7/1997 |
| EP | 1 033 405 A3 | 9/2000 |
| EP | 0 290 799 B9 | 11/2003 |
| WO | WO 87/06614 A1 | 11/1987 |
| WO | WO 92/09696 A1 | 6/1992 |
| WO | WO 93/21335 A2 | 10/1993 |
| WO | WO 94/01930 A1 | 1/1994 |
| WO | WO 00/67558 A1 | 11/2000 |
| WO | WO 02/07275 8 A2 | 9/2002 |
| WO | WO 02/100199 A2 | 12/2002 |
| WO | WO 2003/078577 A2 | 9/2003 |
| WO | WO 2004/035745 A2 | 4/2004 |
| WO | WO 2005/038018 A2 | 4/2005 |
| WO | WO 2005/038033 A2 | 4/2005 |
| WO | WO 2005/046363 A2 | 5/2005 |
| WO | WO 2005/111217 A2 | 11/2005 |
| WO | WO 2005/116199 A2 | 12/2005 |
| WO | WO 2006/022784 A1 | 3/2006 |
| WO | WO 2006/091194 A1 | 8/2006 |
| WO | WO 2006/120570 A2 | 11/2006 |
| WO | WO 2008/070274 A2 | 6/2008 |
| WO | WO 2008/076802 A2 | 6/2008 |
| WO | WO 2009/064771 A2 | 5/2009 |
| WO | WO 2011/088180 A1 | 7/2011 |
| WO | WO 2012/118779 A1 | 9/2012 |

OTHER PUBLICATIONS

U.S. Appl. No. 15/631,873, filed Jun. 23, 2017, U.S. Pat. No. 10,687,490, Issued.
U.S. Appl. No. 14/950,155, filed Nov. 24, 2015, U.S. Pat. No. 10.292,353, Issued.
U.S. Appl. No. 13/361,235, filed Jan. 30, 2012, U.S. Pat. No. 9,228,195, Issued.
U.S. Appl. No. 13/361,159, filed Jan. 30, 2012, U.S. Pat. No. 9,228,194, Issued.
U.S. Appl. No. 12/269,531, filed Nov. 12, 2008, U.S. Pat. No. 8,124,851, Issued.
U.S. Appl. No. 60/337,684, filed Nov. 13, 2001, Xu.
U.S. Appl. No. 60/347,444, filed Jan. 11, 2002, Xu.
U.S. Appl. No. 60/363,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 18, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/665,451, filed Mar. 24, 2005, Xu.
Adams et al., "Genes duplicated by polyploidy show unequal contributions to the transcriptome and organ-specific reciprocal silencing," PNAS, 100(8):4649-54 (2003).
Allen et al., "RNAi-mediated replacement of morphine with the nonnarcotic alkaloid reticuline in opium poppy," Nature Biotechnology, 22(12):1559-1566 (2004).
Alonso et al., "A Hox gene mutation that triggers nonsense-mediated RNA decay and affects alternative splicing during *Drosophila* development," Nucleic Acids Research, 31(14):3873-3880 (2003).
Arciga-Reyes et al., "UPF1 is required for nonsense-mediated mRNA decay (NMD) and RNAi in *Arabidopsis*" The Plant Journal, 47:480-489 (2006).
Arndt et al., "Colocalization of antisense RNAs and ribozymes with their target mRNAs," Genome, 40:785-797 (1997).
ARS-GRIN: PI 551280, "Nicotiana tabacum," http://www.ars-grin.gov/cgi-bin/npgs/acc/display.pl?1446216, accessed Feb. 2009).
Bak et al., "Transgenic Tobacco and *Arabidopsis* Plants Expressing the Two Multifunctional Sorghum Cytochrome P450 Enzymes,

(56) References Cited

OTHER PUBLICATIONS

CYP79A1 and CYP71E1, Are Cyanogenic and Accumulate Metabolites Derived from Intermediates in Dhurrin Biosynthesis," Plant Physiol., 123:1437-1448 (2000).
Bartoszewski et al., "Cloning of a Wound Inducible Lycopersicon esculentum Cytochrome P450 Gene and Lack of Regeneration of Transgenic Plants with Sense or Antisense Constructs," J. Am. Soc. Hort. Sci., 127(4):535-539 (2002).
Baseggio et al., "Size and genomic location of the pMGA multigene family of Mycoplasma gallisepticum," Microbiology, 142:1429-1435 (1996).
Batard et al., "Increasing Expression of P450 and P450-Reductase Proteins from Monocots in Heterologous Systems," Arch. Biochem. Biophys., 379:161-169 (2000).
Baulcombe, "Fast Forward Genetics Based on Virus-Induced Gene Silencing," Current Opinion in Plant Biology, 2:109-113 (1999).
Bolitho et al., "Antisense apple ACC-oxidase RNA reduces ethylene production in transgenic tomato fruit," Plant Science, 122:91-99 (1997).
Bosher et al., "RNA interference: genetic wand and genetic watchdog," Nat. Cell Biol., 2:E31-E36 (2000).
Bosl et al., "The role of noise and positive feedback in the onset of autosomal dominant diseases," BMC Systems Biology, 4:1-15 (2010).
Boyette et al., "Results of year 2000 TSNA sampling program in flue-cured tobacco," Recent Advances in Tobacco Science, 27:17-22 (2001).
Branch, "A good antisense molecule is hard to find," TIBS, 23:45-50 (1998).
Brignetti et al., "Viral pathogenicity determinants are suppressors of transgene silencing in Nicotiana benthamiana," EMBO J., 17(22):6739-6746 (1998).
Burns et al., "Large-scale analysis of gene expression, protein localization, and gene disruption in *Saccharomyces cerevisiae*," Genes Dev., 8:1087-1105 (1994).
Burton et al., Changes in Chemical Composition of Burley Tobacco During Senescence and Curing. 2. Acylated Pyridine Alkaloids, American Chemical Society, pp. 579-583 (1988).
Burton et al., "Distribution of Tobacco Constituents in Tobacco Leaf Tissue. 1. Tobacco-Specific Nitrosamines, Nitrate, Nitrite, and Alkaloids," J. Agric. Food Chem., 40:1050-1055 (1992).
Burton et al., "Changes in Chemical Composition of Burley Tobacco during Senescence and Curing. 2. Acylated Pyridine Alkaloids," J .Agric. Food Chem., 38(3):579-584 (1998).
Bush et al., "Formation of tobacco-specific nitrosamines in air-cured tobacco," Rec. Adv. Tob. Sci, 27:23-46 (2001).
Byers et al., "Killing the messenger: new insights into nonsense-mediated mRNA decay" The Journal of Clinical Investigation, 109(1):3-6 (2002).
Byzova et al., "Transforming petals into sepaloid organs in *Arabidopsis* and oilseed rape: implementation of the hairpin RNA-mediated gene silencing technology in an organ-specific manner," Planta, 218:379-387 (2004).
Callis et al., "Introns increase gene expression in cultured maize cells," Genes and Dev., 1:1183-1200 (1987).
Carron et al., "Genetic modification of condensed tannin biosynthesis in Lotus comiculatus. 1. Heterologous antisense dihydroflavonol reductase down-regulates tannin accumulation in "hairy root" cultures," Theoretical and Applied Genetics, 87(8): 1006-1015 (1994).
Caruthers, "Chapter 1: New Methods for Chemically Synthesizing Deoxyoligonucleotides," Methods of DNA and RNA Sequencing, Weissman (ed.), Praeger Publishers, New York, pp. 1-22 (1983).
Chai et al., "Reducing the maize amylopectin content through RNA interference manipulation," Zhi Wu Sheng Li Yu Fen Zi Sheng Wu Xue Xue Buo, 31:625-630 (2005) (English Abstract only).
Chakrabarti et al., "CYP82E4-mediated nicotine to nomicotine conversion in tobacco is regulated by a senescence-specific signaling pathway," Plant Mol. Biol., 66: 415-427 (2008).

Chang et al., "Predicting and Testing Physical Locations of Genetically Mapped Loci on Tomato Pachytene Chromosome," Genetics, 176:2131-2138 (2007).
Chao et al., "A silent mutation induces exon skipping in the phenylalanine hydroxylase gene in phenylketonuria," Hum. Genet., 108:14-19 (2001).
Chappell, "Biochemistry and Molecular Biology of the Isoprenoid Biosynthetic Pathway in Plants," Annu. Rev. Plant Physiol. Plant Mol. Biol., 46:521-547 (1995).
Chapple, "Molecular-Genetic Analysis of Plant Cytochrome P450-Dependent Monooxygenases," Annu. Rev. Plant Physiol. Plant Mol. Biol., 49:311-343 (1998).
Chelvarajan et al., "Study of Nicotine Demethylation in Nicotiana otophora," J. Agric. Food Chem., 41:858-862 (1993).
Chen et al., "Toxicological analysis of low-nicotine and nocotine-free cigarettes," Toxicology, 249: (2008).
Cheung et al., "A Floral Transmitting Tissue-Specific Glycoprotein Attracts Pollen Tubes and Stimulates Their Growth," Cell, 82:383-393 (1995).
Cho et al., "Transcriptome Analysis and Physical Mapping of Barley Genes in Wheat-Barley Chromosome Addition Lines," Genetics, 172:1277-1285 (2006).
Chou et al., "Chromosome Rearrangements in *Arabidopsis thaliana* Generated Through Cre-lox Site Specific Recombination," Plant and Animal Genome VII Conference, Abstract No. P133, 1 page (1999).
Chuang et al., "Specific and heritable genetic interference by double-stranded RNA in *Arabidopsis thaliana*," PNAS, 97(9):4985-4990 (2000).
Cogoni et al., "Post-transcriptional gene silencing across kingdoms," Curr. Opin. Genet. Dev., 10:638-643 (2000).
Colbert et al., "High-throughput screening for induced point mutations," Plant Physiology, 126:480-484 (2001).
Collier et al., "A Method for Specific Amplification and PCR Sequencing of Individual Members of Multigene Families: Application to the Study of Steroid 21-Hydroxylase Deficiency," PCR Methods and Applications, 1:181-186 (1992).
Colliver et al., "Differential modification of flavonoid and isoflavonoid biosynthesis with an antisense chaicone synthase construct in transgenic Lotus corniculatus," Plant Mol. Biol., 35(4):509-522 (1997).
Crookshanks et al., "The potato tuber transcriptome: analysis of 6077 expressed sequence tags," FEBS Lett., 506:123-126 (2001).
Davuluri et al., "Fruit-specific RNAi-mediated suppression of DET1 enhances carotenoid and favonoid content in tomatoes," Nat. Biotechnol., 23:890-895 (2005).
Dekeyser et al., "Transient Gene Expression in Intact and Organized Rice Tissues," Plant Cell, 2:591-602 (1990).
Dewey et al., Meeting Abstract dated Sep. 27, 2005, 1 page.
Dewey et al., Power point presentation titled "Functional characterization of the nicotine N-Demethylase gene of tobacco," Philip Morris USA, 21 pages, 2006.
Donato et al., "Fluorescence-Based Assays in Intact Cells Expressing Individual Activities for Screening Nine Cytochrome P450 (P450) Human P450 Enzymes," Drug Metab. Dispos., 32(7):699-706 (2004).
D'Souza et al., "Missense and silent tan gene mutations cause frontotemporal dementia with parkinsonism-chromosome 17 type, by affecting multiple alternative RNA splicing regulatory elements" PNAS, 96:5598-5603 (1999).
EBI Accession AV557806, dated Jun. 16, 2000, 2 pages.
Einset, "Differential expression of antisense in regenerated tobacco plants transformed with an antisense version of a tomato ACC oxidase gene," Plant Cell Tissue and Organ Culture, 46(2): 137-141 (1996).
Elkind et al., "Abnormal plant development and down-regulation of phenylpropanoid biosynthesis in transgenic tobacco containing a heterologous phenylalanine ammonia-lyase gene," PNAS, 87(22):9057-61 (1990).
Escobar et al., "RNAi-mediated oncogene silencing confers resistance to crown gall tumorigenesis," PNAS, 98: 13437-13442 (2001).
European Search Report completed on Feb. 10, 2010, in European Application No. EP 07 86 5628, 4 pages.

(56) References Cited

OTHER PUBLICATIONS

European Search Report completed on Mar. 31, 2011, in European Application No. EP 10 01 5540, 8 pages.
Falcon-Perez et al., "Functional Domain Analysis of the Yeast ABC Transporter Ycf1p by Site-directed Mutagenesis," J. Biol. Chem., 274(33):23584-23590 (1999).
Fang et al., "Multiple cis regulatory elements for maximal expression of the cauliflower mosaic virus 35S promoter in transgenic plants," Plant Cell, 1:141-150 (1989).
Fannin et al., "Nicotine demethylation in Nicotiana," Med. Sci. Res., 20:807-808 (1992).
Faske et al., "Transgenic Tobacco Plants Expressing Pea Chloroplast Nmdh cDNA in Sense and Antisense Orientation," Plant Physiol, 115(2): 705-715 (1997).
Fedoroff et al., "Cloning of the bronze locus in maize by a simple and generalizable procedure using the transposable controlling element Activator (Ac)," PNAS, 81:3825-3829 (1984).
Fire et al., "Potent and specific genetic interference by double-stranded RNA in Caenorhabditis elegans," Nature, 391:806-811 (1998).
Force et al., "Preservation of Duplicate Genes by Complementary, Degenerative Mutations," Genetics, 151:1531-1545 (1999).
Forsthoefel et al., "T-DNA Insertion Mutagenesis in *Arabidopsis*: Prospects and Perspectives," Aust. J. Plant Physiol., 19:353-366 (1992).
Frank et al., "Cloning of Wound-Induced Cytochrome P450 Monooxygenases Expressed in Pea," Plant Physiol., 110:1035-1046 (1996).
Freeman et al., "Quantitative RT-PCR: Pitfalls and Potential," BioTechniques, 26:112-125 (1999).
Fromm et al., "An octopine synthase enhancer element directs tissue-specific expression and binds ASF-1, a factor from tobacco nuclear extracts," Plant Cell, 1:977-984 (1989).
GenBank Accession No. CAA64635, dated Sep. 12, 1996, 2 pages.
GenBank Accession No. BAA35080, dated Sep. 26, 2000, 2 pages.
GenBank Accession No. AAK62347, dated Jun. 14, 2001, 2 pages.
GenBank Accession No. AAK62343, dated Feb. 11, 2002, 2 pages.
GenBank Accession No. AAK62346, dated Feb. 11, 2002, 2 pages.
GenBank Accession No. AEK08729 dated Feb. 23, 2005, 2 pages.
GenBank Accession No. AAK62342, Sep. 20, 2005, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07807, dated Oct. 13, 2005, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131888, dated Oct. 13, 2005, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006, 2 pages.
GenBank Accession No. DQ219348, dated Oct. 1, 2006, 2 pages.
GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ219352, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBank Accession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBank Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350337, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350341, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350355, dated Dec. 31, 2006, 2 pages.
GenBank Accession No. DQ350356, dated Dec. 31, 2006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.
GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
GenBank Accession No. DQ205656, dated Jan. 18, 2007, 2 pages.
GenBank Accession No. ABA07806, dated Mar. 7, 2007, 2 pages.
GenBank Accession No. DQ131887, dated Mar. 7, 2007, 2 pages.
Ghosh, "Polyamines and plant alkaloids," Indian J. Exp. Biol., 38:1086-1091 (2000).
Goldrick et al., "Molecular Genetic Analysis of the User Group Associated with Two Mouse Light Chain Genetic Markers," J. Exp. Med., 162:713-728 (1985).
Graham-Lorence et al., "P450s: Structural similarities and functional differences," FASEB J., 10:206-214 (1996).
Guo et al., "Protein Tolerance to Random Amino Acid Change," PNAS, 101(25):9205-9210 (2004).
Hao et al., "Mechanism of Nicotine N-Demethylation in Tobacco Cell Suspension Cultures," Phytochemistry, 41(2):477-482 (1995).
Hao et al., "Nicotine N-Demethylase in Cell-Free Preparations from Tobacco Cell Cultures," Phvtochemistry, 42(2):325-329 (1996).
Hao et al., "Evidence in Favour of an Oxidative N-Demethylation of Nicotine to Nornicotine in Tobacco Cell Cultures," Journal Plant Physiology, 152:420-426 (1998).
Haseloff et al., "Simple RNA enzymes with new and highly specific endoribonuclease activities," Nature, 334:585-591 (1998).
Hayes et al., "Blotting techniques for the study of DNA, RNA, and proteins," BMJ, 299(14):965-968 (1989).
Hecht et al., "The relevance of tobacco-specific nitrosamines to human cancer," Cancer Surveys, 8(2):273-294 (1989).
Hecht, "Biochemistry, Biology, and Carcinogenicity of Tobacco-Specific N-Nitrosamines," Chemical Research in Toxicology, 11(6):559-603 (1998).
Helene et al., "Control of Gene Expression by Triple Helix-Forming Oligonucleotides," Ann. N.Y. Acad. Sci., 660:27-36 (1992).
Helene, "The anti-gene strategy: control of gene expression by triplex-forming-oligonucleotides," Anti-Cancer Drug Des., 6:569-584 (1991).

(56) References Cited

OTHER PUBLICATIONS

Helliwell et al., "High-throughput vectors for efficient gene silencing in plants," Funct. Plant Biol., 29:1217-1225 (2002).
Henikoff et al., "Single-Nucleotide Mutations for Plant Functional Genomics," Annu. Rev. Plant Biol., 54:375-401 (2003).
Herbik et al., "Isolation, characterization and cDNA cloning of nicotianamine synthase from barley," Eur J Biochem, 265(1): 231-9 (1999).
Hibino et al., "Increase of Cinnamaldehyde Groups in Lignin of Transgenic Tobacco Plants Carrying an Antisense Gene for Cinnamyl Alcohol Dehydrogenase," Biosci. Biotec. Biochem, 59:929-931 (1995).
Hildering et al., "Chimeric Stmcture of the Tomato Plant After Seed Treatment with EMS and X-Rays," The Use of Induced Mutations in Plant Breeding, Pergamon Press, pp. 317-320 (1965).
Hill et al., "Functional analysis of conserved histidines in ADP-glucose pyrophosphorylase from *Escerichia coli*," Biochem. Biophys. Res. Commun., 244:573-577 (1998) (Abstract only).
Hoekema et al., "A binary plant vector strategy based on separation of the vir- and T-region of the Agrobacterium tumefaciens Ti-plasmid," Nature, 303:179-180 (1983).
Hoffmann et al., "Tobacco-specific N-nitrosamines and Areca-derived N-nitrosamines: chemistry, biochemistry, carcinogenicity, and relevance to humans," Journal of Toxicology and Environmental Health, 41:1-52 (1994).
Huang et al., "Insights into Regulation and Function of the Major Stress-Induced hsp70 Molecular Chaperone In Vivo: Analysis of Mice with Targeted Gene Disruption of the hsp70. 1 or hsp70.3 Gene," Mol Cell Biol, 21(24):8575-8591 (2001).
Ingelbrecht et al., "Posttranscriptional silencing of reporter transgenes in tobacco correlates with DNA methylation," PNAS, 91:10502-10506 (1994).
International Preliminary Report on Patentability in PCT/US07/087386 dated Jun. 25, 2009, 6 pages.
International Search Report and the Written Opinion of the International Searching Authority, or the Declaration dated May 4, 2012, in International Application No. PCT/US2012/026864 (13 pages).
International Search Report and the Written Opinion of the International Searching Authority, or the Declaration dated Jul. 4, 2012, in International Application No. PCT/US2012/026795 (15 pages).
International Search Report dated Apr. 23, 2014, in International Patent Application No. PCT/US2014/011035 (4 pages).
Invitation to Pay Additional Fees dated Jun. 23, 2014, in International Patent Application No. PCT/US2014/019381, 8 pages.
Isshiki et al., "Nonsense-mediated decay of mutant waxy mRNA in rice," Plant Physiology, 125:1388-1395 (2001).
Jack et al., "Relative stability of nicotine to nomicotine conversion in three hurley cultivars," Coresta Congress, Kyoto, Agro-Phyto groups, Abstract AP2 (2004).
Johnston et al., "Dosage-sensitive function of retinoblastoma related and convergent epigenetic control are required during the *Arabidopsis* life cycle," PLoS Genet, 6(6):e1000988 (2010).
Jorgensen et al., "Chaicone synthase cosuppression phenotypes in petunia flowers: comparison of sense vs. antisense constructs and single-copy vs. complex T-DNA sequences," Plant Mol. Biol., 31:957-973 (1996).
Julio et al. "Reducing the content of nomicotine in tobacco via targeted mutation breeding," Mol. Breeding, 21:369-381 (2008).
Julio et al., "Targeted Mutation Breeding as a tool for tobacco crop improvement," presentation made in Oct. 2008.
Kafri et al., "The regulatory utilization of genetic redundancy through responsive backup circuits," PNAS, 103(31):11653-11658 (2006).
Kempin et al., "Targeted disruption in *Arabidopsis*," Nature, 389:802-803 (1997).
Keskin et al., "A new, structurally nonredundant, diverse data set of protein-protein interfaces and its implications," Protein Science, 13:1043-1055 (2004).

Kim et al., "*Arabidopsis* CYP85A2, a Cytochrome P450, Mediates the Baeyer-Villiger Oxidation of Castasterone to Brassinolide in Brassinosteroid Biosynthesis," Plant Cell, 17:2397-2412 (2005).
Klahre et al., "High molecular weight RNAs and small interfering RNAs induce systemic posttranscriptional gene silencing in plants," PNAS, 99:11981-11986 (2002).
Klink et al., "The Efficacy of RNAi in the Study of the Plant Cytoskeleton," J. Plant Growth Regul., 19:371-384 (2000).
Koornneef, "Chapter 1: Classical mutagenesis in higher plants," Molecular Plant Biology, Gilmartin and Bowler, ed., Oxford University Press, pp. 1-11 (2002).
Koshinsky et al., "Cre-lox site-specific recombination between *Arabidopsis* and tobacco chromosomes," Plant J., 23(6):715-722 (2000).
Kusaba et al., "Low glutelin content1: A Dominant Mutation That Suppresses the Glutelin Multigene Family via RNA Silencing in Rice," Plant Cell, 15:1455-1467 (2003).
Kynast et al., "Dissecting the maize genome by using chromosome addition and radiation hybrid lines," PNAS, 101(26):9921-9926 (2004).
Lazar et al., "Transforming Growth Factor α Mutation of Aspartic Acid 47 and Leucine 48 Results in Different Biological Activities," Mol. Cell. Biol., 8(3):1247-1252 (1988).
Levin et al., "Methods of double-stranded RNA-mediated gene inactivation in *Arabidopsis* and their use to define an essential gene in methionine biosynthesis," Plant Mol. Biol., 44:759-775 (2000).
Lewis et al., "Three nicotine demethylase genes mediate nomicotine biosynthesis in *Nicotiana tabacum* L.: Functional characterization of the CYP82E10 gene," Phytochemistry, 71:1988-1998 (2010).
Lewis, et al. "RNA interference (RNAi)-induced suppression of nicotine demethylase activity reduces levels of a key carcinogen in cured tobacco leaves." Plant Biotechnology Journal, 6:1-9 (2008).
Liu et al., "High-Stearic and High-Oleic Cottonseed Oils Produced by Hairpin RNA-Mediated Post-Transcriptional Gene Silencing," Plant Physiol., 129:1732-1743 (2002).
Liu et al., "Identification and characterization of HTD2: a novel gene negatively regulating tiller bud outgrowth in rice," Planta, 230(4):649-658 (2009).
Liu et al "Genetic and transformation studies reveal negative regulation of ERS1 ethylene receptor signaling in *Arabidopsis*," BMC Plant Biol, 10:60-73 (2010).
Maher, "DNA Triple-Helix Formation: An Approach to Artificial Gene Repressors?" BioEssays, 14(12):807-815 (1992).
Maniatis et al., "Regulation of inducible and tissue-specific gene expression," Science, 236:1237-1245 (1987).
Mansoor et al. "Engineering novel traits in plants through RNA interference," Trends in Plant Science, 11(11):1-7 (2006).
Maquat, "Nonsense-mediated mRNA decay," Curr. Biol., 12(6):R196-R197 (2002).
Matthew, "RNAi for plant functional genomics," Comparative and Functional Genomics, 5:240-244 (2004).
McDougall et al., "Detection of Viral DNA and RNA by In Situ Hybridization," J. Histochem. Cytochem., 34:33-38 (1986).
McKinney et al., "Sequence-based identification of T-DNA insertion mutations in *Arabidopsis*: actin mutants act2-1 and act4-1," Plant J., 8(4):613-622 (1995).
Mesnard et al., "Evidence for the involvement of tetrahydrofolate in the demethylation of nicotine by Nicotiana plumbaginifolia cell-suspension cultures," Planta, 214:911-919 (2002).
Mette et al., "Transcriptional silencing and promoter methylation triggered by double-stranded RNA," EMBO J., 19(19):5194-5201 (2000).
Mol et al., "Regulation of plant gene expression by antisense RNA," FEBS Lett., 268(2):427-430 (1990).
Napoli et al., "Introduction of a Chimeric Chaicone Synthase Gene into Petunia Results in Reversible Co-Suppression of Homologous Genes in trans," Plant Cell, 2:279-289 (1990).
Nawrath et al., "Salicylic Acid Induction-Deficient Mutants of *Arabidopsis* Express PR-2 and PR-5 and Accumulate High Levels of Camalexin after Pathogen Inoculation," Plant Cell, 11:1393-1404 (1999).

(56) References Cited

OTHER PUBLICATIONS

Needleman et al., "A General Method Applicable to the Search for Similarities in the Amino Acid Sequence of Two Proteins," J. Mol. Biol., 48:443-453 (1970).
Nelson et al., "Comparative Genomics of Rice and *Arabidopsis*. Analysis of 727 Cytochrome P450 Genes and Pseudogenes from a Monocot and a Dicot," Plant Physiol., 135:756-772 (2004).
Nelson et al., "Comparison of cytochrome P450 (CYP) genes from the mouse and human genomes, including nomenclature recommendations for genes, pseudogenes and alternative-splice variants," Pharmacogenetics, 14:1-18 (2004).
Ng et al., "Specific Detection and Confirmation of Campylobacter jejuni by DNA Hybridization and PCR," Appl. Environ. Microbiol., 63(11):4558-4563 (1997).
Nishihara et al., "Flavanoid components and flower color change in transgenic tobacco plants by suppression of chaicone isomerase gene," FEBS Lett., 579:6074-6078 (2005).
Odell et al., "Identification of DNA sequences required for activity of the cauliflower mosaic virus 35S promoter," Nature, 313:810-812 (1985).
Office Action dated Oct. 18, 2006, in U.S. Appl. No. 10/293,252.
Office Action dated Oct. 30, 2006, in U.S. Appl. No. 10/686,947.
Office Action dated Nov. 14, 2006, in U.S. Appl. No. 10/387,346.
Office Action dated Nov. 14, 2006, in U.S. Appl. No. 10/340,861.
Office Action dated May 4, 2007, in U.S. Appl. No. 10/943,507.
Office Action dated Jun. 12, 2007, in U.S. Appl. No. 10/934,944.
Ogita et al., "Application of RNAi to confirm theobromine as the major intermediate for caffeine biosynthesis in coffee plants with potential for construction of decaffeinated varieties," Plant Mol. Biol., 54:931-941 (2004).
Ohshima et al., "Nucleotide sequence of the PR-1 gene of Nicotiana tabacum," FEBS Letters, 225:243-246 (1987).
Oliver et al., "Inhibition of tobacco NADH-hydroxypyruvate reductase by expression of a heterologous antisense RNA derived from a cucumber cDNA: Implications for the mechanism of action of antisense RNAs," Mol Gen Genet, 239(3):425-34 (1993).
Pearson et al., "Improved tools for biological sequence comparison," PNAS, 85:2444-2448 (1988).
Peele et al., "Formation of Tobacco-specific Nitrosamines in Flue-cured Tobacco," CORESTA Meeting, Agro-Phyto Groups, Suzhou, China (1999).
Pickett et al., "Seeing Double: Appreciating Genetic Redundancy," Plant Cell, 7:1347-1356 (1995).
Plant Variety Protection Office (USDA-AMS, Beltsville, MD, http://www.ars-grin.gov/cgi-bin/npgs/htmllpvp.pl?Tobbaco, accessed Feb. 2009).
Puchta et al., "Two different but related mechanisms are used in plants for the repair of genomic double-strand breaks by homologous recombination," PNAS, 93:5055-5060 (1996).
Qin et al., "Cre recombinase-mediated site-specific recombination between plant chromosomes," PNAS, 91:1706-1710 (1994).
Qiu et al. "A computational study of off-target effects of RNA interference." Nucleic Acids Research, 33(6)1834-1847 (2005).
Ralston et al., "Cloning, Heterologous Aristolochene-1,3-Dihydroxylase from Expression, and Functional Characterization of 5-epi-Tobacco (*Nicotiana tabacum*)," Arch. Biochem. Biophys., 393(2):222-235 (2001).
Reid et al., "Studies on the Fermentation of Tobacco 1. The Microflora of Cured and Fermenting Cigar-leaf Tobacco," Bulletin 356, Pennsylvania Agricultural Experiment Station, State College, PA, 18 pages (1938).
Rodermel et al., "Nuclear-Organelle Interactions: Nuclear Antisense Gene Inhibits Ribulose Biphosphate Carboxylase Enzyme Levels in Transformed Tobacco Plants," Cell, 55:673-681(1988).
Rohr et al., "Tandem inverted repeat system for selection of effective transgenic RNAi strains of Chlamydomonas," Plant J., 40:611-621 (2004).
Ruiz et al., "Nicotine-free and salt-tolerant tobacco plants obtained by grafting to salinity-resistant rootstocks of tomato," Physiologia Plantarum, 24:(4):465-475 (2005).

Salehuzzaman et al., "Isolation and characterization of a cDNA encoding granule-bound starch synthase in cassava (*Manihot esculenta* Crantz) and its antisense expression in potato," Plant Mol Biol, 23(5):947-62 (1993).
Schenk et al., "Coordinated plant defense responses in *Arabidopsis* revealed by microarray analysis," PNAS, 97(21):11655-11660 (2000).
Schnable et al., "Genetic recombination in plants," Curr. Opin. Plant Biol., 1:123-129 (1998).
Schopfer et al., "Identification of elicitor-induced cytochrome P450s of soybean (*Glycine max* L.) using differential display of mRNA," Mol. Gen. Genet., 258:315-322 (1998).
Seal et al., "Isolation of a Pseudomonas solanacearum-Specific DNA Probe by Subtraction Hybridization and Construction of Species-Specific Oligonucleotide Primers for Sensitive Detection by the Polymerase Chain Reaction," Appl. Environ. Microbiol., 58(2):3751-3758 (1992).
Sequence 6912fl obtained from the Internet at http://mrg.pscsiken.go.ip/nicotiana/menu/069.html on Dec. 6, 2007, 1 page.
Shah et al., "Expression of Silent Mutations in Disease Phenotype," Abstract for presentation at 11th International Congress of Human Genetics, 1 page, (2006).
Shen et al., "Resistance Gene Candidates Identified by PCR with Degenerate Oligonucleotide Primers Map to Clusters of Resistance Genes in Lettuce," Molecular Plant-Microbe Interactions, 11(8):815-823 (1998).
Shew et al. (Eds.), "Compendium of Tobacco Diseases," published by American Phytopathology Society, 99 pages (1991).
Sinvany-Villalobo et al., "Expression in Multigene Families. Analysis of Chloroplast and Mitochondrial Proteases," Plant Physiol, 135:1336-1345 (2004).
Skarnes, "Entrapment Vectors: A New Tool for Mammalian Genetics," Bio/Technology, 8:827-831 (1990).
Smith et al., "Comparison of Biosequences," Adv. Appl. Math., 2:482-489 (1981).
Smith et al., "Total silencing by intron-spliced hairpin RNAs," Nature, 407:319-320 (2000).
Spradling et al., "Gene disruptions using P transposable elements: An integral component of the *Drosophila* genome project," PNAS, 92:10824-10830 (1995).
Stalberg et al., "Deletion analysis of a 2S seed storage protein promoter of *Brassica napus* in transgenic tobacco," Plant Mol. Biol., 23:671-683 (1993).
Sundaresan et al., "Patterns of gene action in plant development revealed by enhancer trap and gene trap transposable elements," Genes Dev., 9:1797-1810 (1995).
Sureka et al., "Positive Feedback and Noise Activate the Stringent Response Regulator Rel in Mycobacteria," PLoS One, 3(3):e1771 (2008).
Takeda et al., "Differentiation between Wild and Vaccine-Derived Strains of Poliovirus by Stringent Microplate Hybridization of PCR Products," J. Clin. Microbiol., 32:202-204 (1994).
Takemoto et al., "Molecular Cloning of a Defense-Response-Related Cytochrome P450 Gene from Tobacco," Plant Cell Physiol., 40(12):1232-1242 (1999).
Takken et al. "A functional cloning strategy, based on a binary PVX-expression vector, to isolate HR-inducing cDNAs of plant pathogens." The Plant Journal, 24(2): 275-283 (2000).
Tavernarakis et al., "Heritable and inducible genetic interference by double-stranded RNA encoded by transgenes," Nat. Genet., 24:180-183 (2000).
Temple et al., "Modulation of glutamine synthetase gene expression in tobacco by the introduction of an alfalfa glutamine synthetase gene in sense and antisense orientation: molecular and biochemical analysis," Mol Gen Genet, 236(2-3):315-25 (1993).
Thomas et al., "Size constraints for targeting post-transcriptional gene silencing and for RNAdirected methylation in Nicotiana benthamiana using a potato virus X vector," Plant J., 25(4):417-425 (2001).
Thornton et al., "From structure to function: Approaches and limitations," Nature Structural Biology, Structural Genomics Supplement, pp. 991-994 (2000).
Till et al., "Discovery of induced point mutations in maize genes by TILLING," BMC Plant Biology, 4:12 (2004).

(56) References Cited

OTHER PUBLICATIONS

Toscano et al., "A silent mutation (2939G>A, exon 6; CYP2D6*59) leading to impaired expression and function of CYP2D6," Pharmacogenet. Genomics, 16(10):767-770 (2006).
Travella, et al. "RNA Interference-Based Gene Silencing as an Efficient Tool for Functional Genomics in Hexapioid Bread Wheat." Plant Physiology, 142:6-20 (2006).
Trevanion et al., "NADP-Malate Dehydrogenase in the C4 Plant *Flaveria bidentis*," Plant Physiol, 113(4):1153-1165 (1997).
Turner et al., "Post-transcriptional gene-silencing and RNA interference: genetic immunity, mechanisms and applications," J. Chem. Technol. Biotechnol., 75:869-882 (2000).
United States, "Tobacco in the United States," Miscellaneous Publication No. 867, U.S. Dept. of Agriculture, Agricultural Marketing Service, 27 pages (1979).
Vaistij et al., "Spreading of RNA Targeting and DNA Methylation in RNA Silencing Requires Transcription of the Target Gene and a Putative RNA-Dependent RNA Polymerase," Plant Cell, 14:857-867 (2002).
Van der Krol et al., "An anti-sense chaicone synthase gene in transgenic plants inhibits flower pigmentation," Nature, 333:866-869 (1988).
Van der Krol et al., "Antisense genes in plants: an overview," Gene, 72:45-50 (1988).
Vaucheret et al., "Post-transcriptional gene silencing in plants," J. Cell Sci., 114:3083-3091 (2001).
Veena et al., "Glyoxalase I from *Brassica juncea*: molecular cloning, regulation and its overexpression confer tolerance in transgenic tobacco under stress," Plant Journal, 17(4):385-395 (1999).
Verdaguer et al., "Functional organization of the cassava vein mosaic virus (CsVMV) promoter," Plant Mol. Biol., 37(6):1055-1067 (1998).
Verkerk, "Chimerism of the tomato plant after seed irradiation with fast neutrons," Neth. J. Agric. Sci., 19:197-203 (1971).
Voss et al., "The role of enhancers in the regulation of cell-type-specific transcriptional control," Trends Biochem. Sci., 11(7):287-289 (1986).
Wang et al., "Suppression of a P450 hydroxylase gene in plant trichome glands enhances natural product-based aphid resistance," Nat. Biotechnol., 19:371-374 (2001).
Wang et al., "Isolation and characterization of the CYP71D16 trichome-specific promoter from *Nicotania tabacum* L," J. Exp. Botany, 53(376):1891-1897 (2002).
Wang et al., "Elucidation of the functions of genes central to diterpene metabolism in tobacco trichomes using post-transcriptional gene silencing," Planta, 216:686-691 (2003).
Waterhouse et al., "Virus resistance and gene silencing in plants can be induced by simultaneous expression of sense and antisense RNA," PNAS, 95:13959-13964 (1998).
Weigel et al., "A developmental switch sufficient for flower initiation in diverse plants," Nature, 377:495-500 (1995).
Weising et al., "Foreign Genes in Plants: Transfer, Structure, Expression, and Applications," Ann. Rev. Genetics, 22:421-477 (1988).
Werck-Reichhart et al., "Cytochromes P450: a success story," Genome Biology, 1(6):reviews3003.1-3003.9 (2000).
Werck-Reichhart et al., "Cytochromes P450," The *Arabidopsis* Book, American Society of Plant Biologists, 28 pages (2002).
Wernsman et al., "Time and site of nicotine conversion in tobacco," Tobacco Science, 167(22):226-228 (1968).
Wernsman et al., "Relative Stability of Alleles at the Nicotine Conversion Locus of Tobacco," Tobacco Science, 14:34-36 (1970).
Wernsman et al., "Chapter Seventeen: Tobacco." Cultivar Development. Crop Species., W. H. Fehr (ed.), MacMillan Publishing Go., Inc., New York, N.Y., pp. 669-698 (1987).
Wesley et al., "Construct design for efficient, effective and high-throughput gene silencing in plants," The Plant Journal, 27(6):581-590 (2001).
Wetmur, "DNA Probes: Applications of the Principles of Nucleic Acid Hybridization" Critical Reviews in Bio. and Mol. Biol., 26:227-259, (1991).
Whitbred et al., "Molecular Characterization of CYP73A9 and CYP82A1 P450 Genes Involved in Plant Defense in Pea," Plant Physiol., 124:47-58 (2000).
Written Opinion of the International Searching Authority dated Apr. 23, 2014, in International Patent Application No. PCT/US2014/011035.
Wu et al. "Herbivory Rapidly Activates MAPK Signaling in Attacked and Unattacked Leaf Regions but Not between Leaves of *Nicotiana attenuata*." The Plant Cell, 19:1096-1122 (2007).
Xiong et al., "Different effects on ACC oxidase gene silencing triggered by RNA interference in transgenic tomato," Plant Cell, 23:639-646 (2004).
Xu et al. "Computational Estimation and Experimental Verification of Off-Target Silencing during Posttranscriptional Gene Silencing in Plants," Plant Physiology, 142:429-440 (2006).
Xu et al., "Biochemical and molecular characterizations of nicotine demethylase in tobacco," Physiologia Plantarum, 129(2):307-319 (2007).
Zwart et al., "Rapid Screening for Freshwater Bacterial Groups by Using Reverse Line Blot Hybridization," Appl. Environ. Microbiol., 69(10):5875-5883 (2003).
Chakrabarti, M., et al., "Inactivation of the Cytochrome P450 Gene CYP82E2 by Degenerative Mutations Was a Key Event in the Evolution of the Alkaloid Profile of Modern Tobacco," New Phytol., May 30, 2007, pp. 565-574, vol. 175, No. 3.
Chintapakorn, Y., et al., "Antisense-Mediated Down-Regulation of Putrescine N-Methyltransferase Activity in Transgenic *Nicotiana tabacum* L. Can Lead to Elevated Levels of Anatabine at the Expense of Nicotine," Plant Molecular Biology, 2003, pp. 87-105, vol. 53.
Gavilano, L.B., "Isolation, Cloning and Characterization of Novel Tobacco Cytochrome P450 Genes Involved in Secondary Metabolism," Plant Biology Meeting, Jul. 24-28, 2004, Lake Buena Vista, Florida, Abstract No. 992, Retrieved from the Internet: URL: http://abstracts.aspb.org/pb2004/public/P75/8027.html.
Gavilano, L.B., et al., "Genetic Engineering of Nicotiana tabacum for Reduced Nornicotine Content," J. Agric. Food Chem., Jul. 11, 2006, pp. 9071-9078, vol. 54, No. 24.
Gavilano, L.B., and B. Siminszky, "Isolation and Characterization of the Cytochrome P450 Gene CYP82E5v2 that Mediates Nicotine to Nornicotine Conversion in the Green Leaves of Tobacco," Plant Cell Physiol., Oct. 8, 2007, pp. 1567-1574, vol. 48, No. 11.
Gavilano, L.B., et al., "Functional Analysis of Nicotine Demethylase Genes Reveals Insights into the Evolution of Modern Tobacco," J. Biol. Chem, Jan. 5, 2007, pp. 249-256, vol. 282, No. 1.
Siminszky, B., et al., "Conversion of Nicotine to Nornicotine in Nicotiana tabacum is Mediated by CYP82E4, a Cytochrome P450 Monooxygenase," PNAS, Oct. 11, 2005, pp. 14919-14924, vol. 102, No. 41.
Tang & Galili, "Using RNAi to Improve Plant Nutritional Value: From Mechanism to Application," Trends in Biotechnology, 2004, pp. 463-469, vol. 22, No. 9.
EMBL Database Report for Accession No. DQ350312, Dec. 31, 2006 (XP002511577).
EMBL Database Report for Accession No. EU182719, Dec. 2, 2007 (XP002511576).
Demole, E. and Berthet, D., "A Chemical Study of Burley Tobacco Flavour (*Nicotiana tabacum* L.), I. Volatile to medium-volatile constituents (b. p.≤84°/0.001 Torr," Helvetica Chimica Acta, 1972, pp. 1866-1882, vol. 55, Fasc. 6, Nr. 175-176.
Uniprot Q38Q86 Cytochrome P450 monooxygenase CYP82E4v1—first available online: Nov. 22, 2005.
Gavilano, et al., "Isolation and Characterization of the Cytochrome P450 Gene CYP82E5v2 that Mediates Nicotine to Nornicotine Conversion in the Green Leaves of Tobacco," Plant Cell Physiol., 2007, vol. 48(11), pp. 1567-1574.
Extended European Search Report for European Application No. 12199188.9; dated Feb. 22, 2013.

* cited by examiner

FIG. 1A

```
              1                                                                    50
CYP82E4v2    MLSPIEAIVG  LVTFTFLFYF  LWTKKSQKPS  KPLPPKIPGG  WPVIGHLFHF
CYP82E4v6    MLSPIEAIVG  LVTFTFLFYF  LWTKKSQKPS  KPLPPKIPGG  WPVIGHLFHF
CYP82E4v12   MLSPIEAIVG  LVTFTFLFYF  LWTKKSQKPS  KPLPPKIPGG  WPVIGHLFHF
58-166       MVLPIEAIVG  LVTFTFLFYF  LWTKKSQKPS  KPLPPKIPGG  WPVIGHLFHF
CYP82E3      MVLPVEAIVG  LVTFTFLFYF  LWTKKSQKPS  KPLPPKIPGG  WPVIGHLFYF
CYP82E2v1    MVLPIEAFVG  LVTFTFLLYF  LWTKKSQKLP  KPLPPKIPGG  WPVIGHLFHF
CYP82E2v2    MLSPIEAFVG  LVTFTFLLYF  LWTKKSQKLP  KPLPPKIPGG  WPVIGHLFHF
CYP82E5v2    MVSPVEAIVG  LVTITILFYF  LWRKKFQLPS  KPLPPKIPGG  WPVIGHLFYF 51                                                                   100
CYP82E4v2    NDDGDDRPLA  RKLGDLADKY  GPVFTFRLGL  PLVLVVSSYE  AVKDCFSTND
CYP82E4v6    NDDGDDRPLA  RKLGDLADKY  GPVFTFRLGL  PLVLVVSSYE  AVKDCFSTND
CYP82E4v12   NDDGDDRPLA  RKLGDLADKY  GPVFTFRLGL  PLVLVVSSYE  AVKDCFSTND
58-166       NDDGNDRPLA  RKLGDLADKY  GPVFTFRLGL  PLVLVVSSYE  AIKDCFSTND
CYP82E3      DDDGDDRPLA  RKLGDLADKY  GPVFTFRLGL  PLVLVVSSYE  AIKDCFSTND
CYP82E2v1    NNDGDDRPLA  RKLGDLADKY  GPVFTFRLGL  PLVLVVSSYE  AIKDCFSTND
CYP82E2v2    NNDGDDRPLA  RKLGDLADKY  GPVFTFRLGL  PLVLVVSSYE  AIKDCFSTND
CYP82E5v2    DDDGDDRPLA  RKLGDLADKY  GPVFTFRLGL  PLVLVVSSYE  AVKDCFSTND 101                                                                  150
CYP82E4v2    AIFSNRPAFL  YGDYLGYNNA  MLFLANYGPY  WRKNRKLVIQ  EVLSASRLEK
CYP82E4v6    AIFSNRPAFL  YGDYLGYNNA  MLFLANYGPY  WRKNRKLVIQ  EVLSASRLEK
CYP82E4v12   AIFSNRPAFL  YGDYLGYNNA  MLFLANYGPY  WRKNRKLVIQ  EVLSASRLEK
58-166       AIFSNRPAFL  YGEYLGYNNA  MLFLANYGPY  WRKNRKLVIQ  EVLSASRLEK
CYP82E3      AIFSNRPAFL  YGEYLGYKNA  MLFLANYGSY  WRKNRKLIIQ  EVLSASRLEK
CYP82E2v1    AIFSNRPAFL  YGEYLGYNNN  MLFLANYGPY  WRKNRKLVIQ  EVLSASRLEK
CYP82E2v2    AIFSNRPALL  YGEYLGYNNN  MLFLANYGPY  WRKNRKLVIQ  EVLSASRLEK
CYP82E5v2    AIFSNRPAFL  YGEYLGYSNA  MLFLIKYGPY  WRKNRKLVIQ  EVLSASRLEK 151                                                                  200
CYP82E4v2    FKHVRFARIQ  ASIKNLYTRI  DGNSSTINLT  DWLEELNFGL  IVKMIAGKNY
CYP82E4v6    FKHVRFARIQ  ASIKNLYTRI  DGNSSTINLT  DWLEELNFGL  IVKMIAGKNY
CYP82E4v12   FKHVRFARIQ  ASIKNLYTRI  DGNSSTINLT  DWLEELNFGL  IVKMIAGKNY
58-166       FKHVRFARIQ  TSIKNLYTRI  DNNSSTINLT  DWLEELNFGL  IVKMIAGKNY
CYP82E3      FKHVRFARIQ  TSIKNLYTRI  DGNSSTINLT  DWLEELNFGL  IVKMIAGKNY
CYP82E2v1    FKQVRFTRIQ  TSIKNLYTRI  NGNSSTINLT  DWLEELNFGL  IVKMIAGKNY
CYP82E2v2    FKQVRFTRIQ  TSIKNLYTRI  NGNSSTINLT  DWLEELNFGL  IVKMIAGKNY
CYP82E5v2    LKHVRFCKIQ  TSIKSLYTRI  DGNSSTINLT  DWLEELNFGL  IVKMIAGKNY
```

FIG. 1B

```
              201                                                              250
CYP82E4v2     ESGKGDEQVE  RFKKAFKDFM  ILSMEFVLWD  AFPIPLFKWV  DFQGHVKAMK
CYP82E4v6     ESGKGDEQVE  RFKKAFKDFM  ILSMEFVLWD  AFPIPLFKWV  DFQGHVKAMK
CYP82E4v12    ESGKGDEQVE  RFKKAFKDFM  ILSMEFVLWD  AFPIPLFKWV  DFQGHVKAMK
     58-166   ESGKGDEQVE  RFKKAFKDFM  ILSMEFVLWD  AFPIPLFKWV  DFQGHVKAMK
CYP82E3       ESGKGDEQVE  RFKKAFKDFM  ILSMEFVLWD  AFPIPLFKWV  DFQGHVKAMK
CYP82E2v1     ESGKGDEQVE  RFKNAFKDFM  VLSMEFVLWD  AFPIPLFKWV  DFQGHVKAMK
CYP82E2v2     ESGKGDEQVE  RFKNAFKDFM  VLSMEFVLWD  AFPIPLFKWV  DFQGHVKAMK
CYP82E5v2     ESGKGDEQVE  RFRKAFKDFI  ILSMEFVLWD  AFPIPLFKWV  DFQGHVKAMK 251                                                              300
CYP82E4v2     RTFKDIDSVF  QNWLEEHINK  REK.MEVNAE  GNEQDFIDVV  LSKMSNEYLG
CYP82E4v6     RTFKDIDSVF  QNWLEEHINK  REK.MEVNAE  GNEQDFIDVV  LSKMSNEYLG
CYP82E4v12    RTFKDIDSVF  QNWLEEHINK  REK.MEVNAE  GNEQDFIDVV  LSKMSNEYLG
     58-166   RTFKDIDSVF  QNWLEEHINK  REK.MEVNAE  GNEQDFIDVV  LSKMSNEYLG
CYP82E3       RTFKDIDSVF  QNWLEEHIKK  REKNMEVGTE  GNEQDFIDVV  LSKMSNEYLG
CYP82E2v1     RTFKDIDSVF  QNWLEEHINK  REK.MEVGAE  GNEQDFIDVV  LSKISKEYLG
CYP82E2v2     RTFKDIDSVF  QNWLEEHINK  REK.MEVGAE  GNEQDFIDVV  LSKISKEYLG
CYP82E5v2     RTFKDIDSVF  QNWLEEHVKK  REK.MEVNAQ  GNEQDFIDVV  LSKMSNEYLG 301                                                              350
CYP82E4v2     EGYSRDTVIK  ATVFSLVLDA  ADTVALHINW  GMALLINNQN  ALKKAQEEID
CYP82E4v6     EGYSRDTVIK  ATVFSLVLDA  ADTVALHINW  GMALLINNQN  ALKKAQEEID
CYP82E4v12    EGYSRDTVIK  ATVFSLVLDA  ADTVALHINW  GMALLINNQN  ALKKAQEEID
     58-166   EGYSRDTVIK  ATVFSLVLDA  ADTVALHINW  GMALLINNQN  ALKKAQEEID
CYP82E3       EGYSRDTVIK  ATVFSLVLDA  ADTVALHINW  GMALLINNQN  ALKKAQEEID
CYP82E2v1     EGYSRDTVIK  ATVFSLVLDA  ADTVALHINW  GMTLLINNQN  ALKKAQEEID
CYP82E2v2     EGYSRDTVIK  ATVFSLVLDA  ADTVALHINW  GMTLLINNQN  ALKKAQEEID
CYP82E5v2     EGYSRDTVIK  ATVFSLVLDA  ADTVALHINW  GMALLINNQN  ALKKAQEEID 351                                                              400
CYP82E4v2     TKVGKDRWVE  ESDIKDLVYL  QAIVKEVLRL  YPPGPLLVPH  ENVEDCVVSG
CYP82E4v6     TKVGKDRWVE  ESDIKDLVYL  QAIVKEVLRL  YPPGPLLVPH  ENVEDCVVSG
CYP82E4v12    TKVGKDRWVE  ESDIKDLVYL  QAIVKEVLRL  YPPGPLLVPH  ENVEDCVVSG
     58-166   TIVGKDRWVE  ESDIKDLVYL  QAIVKEVLRL  YPPGPLLVPH  ENIEDCVVSG
CYP82E3       TKVGKDRWVE  ESDIKDLVYL  QAIVKEVLRL  YPPGPLLVPH  ENVEDCVVSG
CYP82E2v1     TKVGKDRWVE  ESDIKDLVYL  QAIVKKVLRL  YPPGPLLVPH  ENVKDCVVSG
CYP82E2v2     TKVGKDRWVE  ESDIKDLVYL  QAIVKKVLRL  YPPGPLLVPH  ENVKDCVVSG
CYP82E5v2     KKVGKERWVE  ESDIKDLVYL  QAIVKEVLRL  YPPGPLLVPH  ENVEDCVVSG 401                                                              450
CYP82E4v2     YHIPKGTRLF  ANVMKLQRDP  KLWSDPDNFD  PERFIATDID  FRGQYYKYIP
CYP82E4v6     YHIPKGTRLF  ANVMKLQRDP  KLWSDPDNFD  PERFIATDID  FRGQYYKYIP
CYP82E4v12    YHIPKGTRLF  ANVMKLQRDP  KLWSDPDNFD  PERFIATDID  FRGQYYKYIP
     58-166   YIIPKGTRLF  ANVMKLQRDP  KLWENPDNFD  PERFYAAGID  FRGQHYEYIP
CYP82E3       YHIPKGTRLF  ANVMKLQRDP  KLWSNPDKFN  PERFIARDID  FHGQHYEYIP
```

FIG. 1B
(cont.)

```
CYP82E2v1   YHIPKGTRLF ANVMKLQRDP KLLSNPDKFD PERFIAGDID FRGHHYEFIP
CYP82E2v2   YHIPKGTRLF ANVMKLQRDP KLLSNPDKFD PERFIAGDID FRGHHYEFIP
CYP82E5v2   YHIPKGTRLF ANVMKLQRDP KLWSNPDKFD PERFFADDID FRGQHYEFIP
```

FIG. 1C

```
              451                                                          500
  CYP82E4v2   FGSGRRSCPG MTYALQVEHL TMAHLIQGFN YRTPNDEPLD MKEGAGITIR
   CYP82E4v6  FGSGRRSCPG MTYALQVEHL TMAHLIQGFN YRTPNDEPLD MKEGAGITIR
  CYP82E4v12  FGSGRRSCPG MTYALQVEHL TMAHLIQGFN YRTPNDEPLD MKEGAGITIR
       58-166 FGSGRRSCPG MTYALQVEHL TMAHLIQGFN YSTPNDEPLD MKEGAGITIR
       CYP82E3 FGSGRRSCPG MTYALQVEHL TMAHLIQGFN YRTPIDEPLD MKEGAGITIR
     CYP82E2v1 FGSGRRSCPG MTYALQVEHL TMAHLIQGFN YKTPNDEALD MKEGAGITIR
     CYP82E2v2 FGSGRRSCPG MTYALQVEHL TMAHLIQGFN YKTPNDEALD MKEGAGITIR
     CYP82E5v2 FGSGRRSCPG MTYALQAEHL TIAHLIQGFN YRTPNDEPLD MKEGAGITIR 501        518
   CYP82E4v2  KVNPVELIIA PRLAPELY
   CYP82E4v6  KVNPVELIIA PRLAPELY
  CYP82E4v12  KVNPVELIIA PRLAPELY
       58-166 KVNPVEVIIM PRLAPELY
       CYP82E3 KVNPVKVIIT PRLAPELY
     CYP82E2v1 KVNPVELIIT PRLAPELY
     CYP82E2v2 KVNPVELIIT PRLAPELY
     CYP82E5v2 KVNPVEVIIT ARLAPELY
```

ALTERATION OF TOBACCO ALKALOID CONTENT THROUGH MODIFICATION OF SPECIFIC CYTOCHROME P450 GENES

CROSS-REFERENCE TO RELATED APPLICATIONS

This application is a continuation of U.S. application Ser. No. 16/860,542, filed Apr. 28, 2020, which is a continuation of U.S. application Ser. No. 15/631,873, filed Jun. 23, 2017, which is a continuation of U.S. application Ser. No. 14/950, 155, filed Nov. 24, 2015, which is a continuation of U.S. application Ser. No. 13/361,235, filed Jan. 30, 2012, which is a divisional of U.S. application Ser. No. 12/269,531, filed Nov. 12, 2008, which claims the benefit of U.S. Provisional Application No. 60/987,243, filed Nov. 12, 2007, the contents of each of which are hereby incorporated in their entirety by reference herein.

U.S. application Ser. No. 14/950,155, filed Nov. 24, 2015, is also a continuation of U.S. application Ser. No. 13/361, 159, filed Jan. 30, 2012, which is a divisional of U.S. application Ser. No. 12/269,531, filed Nov. 12, 2008, which claims the benefit of U.S. Provisional Application No. 60/987,243, filed Nov. 12, 2007, the contents of each of which are hereby incorporated in their entirety by reference herein.

REFERENCE TO SEQUENCE LISTING SUBMITTED ELECTRONICALLY

An official copy of the Sequence Listing is submitted electronically via EFS-Web as an ASCII formatted Sequence Listing with a file named "575405SEQLIST.txt," created on May 18, 2022, having a size of 136 KB. The Sequence Listing contained in this ASCII formatted document is part of the specification and is herein incorporated by reference in its entirety.

FIELD OF THE INVENTION

The present invention relates to compositions and methods for reducing the level of nornicotine and its metabolite, N'-nitrosonornicotine (NNN), in a plant that is a member of the genus *Nicotiana*, particularly compositions and methods for inhibiting expression or function of a cytochrome P450 polypeptide involved in the metabolic conversion of nicotine to nornicotine.

BACKGROUND OF THE INVENTION

A predominant alkaloid found in commercial tobacco varieties is nicotine, typically accounting for 90%-95% of the total alkaloid pool. The remaining alkaloid fraction is primarily three additional pyridine alkaloids: nornicotine, anabasine and anatabine. Nornicotine is generated directly from nicotine by nicotine N-demethylase. Nornicotine usually represents less than 5% of the total pyridine alkaloid pool. However, tobacco plants that initially produce very low amounts of nornicotine can give rise to progeny that metabolically "convert" a large percentage of leaf nicotine to nornicotine. This process is termed "conversion." In tobacco plants that have genetically converted (i.e., "converters"), the great majority of nornicotine production occurs during senescence and curing of a mature leaf (Wernsman & Matzinger (1968) *Tob. Sci.* 12:226-228). Burley tobaccos are particularly prone to genetic conversion, with rates as high as 20% per generation observed in some cultivars.

During curing and processing of the tobacco leaf, a portion of the nornicotine is metabolized to NNN, a tobacco-specific nitrosamine (TSNA) alleged to be carcinogenic in laboratory animals (Hecht & Hoffmann (1990) *Cancer Surveys* 8:273-294; and Hoffmann et al. (1994) *J. Toxicol. Environ. Health* 41:1-52; Hecht (1998) *Chem. Res. Toxicol.* 11:559-603). In flue-cured tobaccos, TSNAs predominantly form through a reaction of alkaloids with minute amounts of nitrogen oxides present in combustion gases in a direct-fired heating systems used in traditional curing barns (Peele & Gentry (1999) "Formation of tobacco-specific nitrosamines in flue-cured tobacco," CORESTA Meeting, Agro-Phyto Groups, Suzhou, China). The combustion gases, however, can be eliminated when curing barns are retrofitted with heat-exchangers, which eliminate the mixing of combustion gases with curing air, thereby reducing TSNAs in tobaccos cured in this manner (Boyette & Hamm (2001) *Rec. Adv. Tob. Sci.* 27:17-22.). In contrast, in air-cured Burley tobaccos, TSNA formation primarily proceeds through a reaction of tobacco alkaloids with nitrite, a process catalyzed by leaf-borne microbes (Bush et al. (2001) *Rec. Adv. Tob. Sci.* 27:23-46). Thus far, attempts to reduce TSNAs through modification of curing conditions while maintaining acceptable quality standards have not been successful for air-cured tobaccos.

In Burley tobacco plants, a positive correlation exists between the nornicotine content of a leaf and an amount of NNN that accumulates in the cured leaf (Bush et al. (2001) *Rec. Adv. Tob. Sci,* 27:23-46; and Shi et al. (2000) *Tob. Chem. Res. Conf.* 54:Abstract 27). However, keeping nornicotine levels at a minimum is difficult in Burley tobacco plants because of conversion. Plant breeders and seed producers are traditionally responsible for minimizing the number of Burley tobacco plants that accumulate high levels of nornicotine. Though the percentage of converters that are ultimately grown in fields are reduced through roguing converters during propagation of seed stocks. Unfortunately, this process is costly, time-consuming and imperfect.

Once a plant converts, the high nornicotine trait is inherited as a single dominant gene (Griffith et al. (1955) *Science* 121:343-344; Burke & Jeffrey (1958) *Tob. Sci.* 2:139-141; and Man et al. (1964) *Crop Sci.* 4:349-353). The nature of this gene, however, is currently unknown. In the simplest of scenarios, the conversion locus may represent a nonfunctional nicotine N-demethylase gene that regains its function in converters, possibly through the mobilization of a mutation-inducting transposable element. Alternatively, the converter locus may encode a protein that initiates a cascade of events that ultimately enables converters to metabolize nicotine to nornicotine, meaning that multiple genes may be involved.

Regardless of whether there are one or many genes associated with conversion, the gene(s) encoding polypeptides having nicotine demethylase activity play a pivotal role in this process. Although the inability to purify active nicotine N-demethylase from crude extracts has impeded the isolation and identification of this enzyme, there is some evidence that a member of the cytochrome P450 superfamily of monooxygenases may be involved (Hao & Yeoman (1996) *Phytochem.* 41:477-482; Hao & Yeoman (1996) *Phytochem.* 42:325-329; Chelvarajan et al. (1993) *J. Agric, Food Chem.* 41:858-862; and Hao & Yeoman (1998) *J. Plant Physiol.* 152:420-426). Unfortunately, these studies are not conclusive, as classic P450 inhibitors, such as carbon monoxide and tetcylasis, fail to lower enzyme activity at rates comparable to other reported P450-mediated reactions (Chelvarajan et al. (1993) *J. Agric. Food Chem.* 41:858-862).

Furthermore, cytochrome P450s are ubiquitous, transmembrane proteins that participate in metabolizing a wide range of compounds (reviewed by Schuler (1996) *Crit. Rev. Plant Sci.* 15:235-284; and Schuler & Werck-Reichhart (2003) *Annu. Rev. Plant Biol.* 54:629-667). Examples of biochemical reactions mediated by cytochrome P450s include hydroxylations, demethylations and epoxidations. In plants, cytochrome P450 gene families are very large. For example, total genome sequence examination revealed 272 predicted cytochrome P450 genes in *Arabidopsis* and at least 455 unique cytochrome P450 genes in rice (see, e.g., Nelson et al. (2004) *Plant Physiol.* 135(2):756-772). Even though cytochrome P450s have been implicated in the conversion of nicotine to nornicotine, identification of key participating members of this protein family remains a challenge.

Aside from serving as a precursor for NNN, recent studies suggest that the nornicotine found in tobacco products has undesirable health consequences. For example, Dickerson & Janda demonstrated that nornicotine causes aberrant protein glycosylation within a cell (Dickerson & Janda (2002) *Proc. Natl. Acad. Sci USA* 99:15084-15088). Likewise, concentrations of nornicotine-modified proteins were much higher in plasma of smokers compared to nonsmokers. Furthermore, nornicotine can covalently modify commonly prescribed steroid drugs such as prednisone, which can alter both the efficacy and toxicity of these drugs.

In view of the difficulties associated with conversion, as well as the undesirable health effects of nornicotine accumulation, improved methods for reducing the nornicotine content in tobacco varieties, particularly Burley tobacco plants, are therefore desirable. Such methods would not only help ameliorate the potential negative health consequences of the nornicotine per se as described above, but also help to reduce NNN levels.

SUMMARY OF THE INVENTION

Compositions and methods are provided for reducing the nornicotine content in plants that are members of the genus *Nicotiana*. Compositions include isolated cytochrome P450 polynucleotides and polypeptides that are involved in conversion of nicotine to nornicotine in plants, particularly *Nicotiana* species. Isolated polynucleotides include those that comprise a nucleic acid sequence as set forth in SEQ ID NO:1, 3 or 4, a nucleic acid sequence encoding a polypeptide as set forth in SEQ ID NO:2, 5-12, 14-24, and fragments and variants thereof. Isolated polypeptides of the invention include those that comprise an amino acid sequence as set forth in SEQ ID NO:2, 5-12 or 14-24, an amino acid sequence encoded by the nucleic acid sequence set forth in SEQ ID NO:1, 3 or 4, and fragments and variants thereof.

In a first aspect, the present invention is summarized as polynucleotides that can suppress expression of a nicotine demethylase involved in the metabolic conversion of nicotine to nornicotine in a plant, including the nicotine demethylases of the present invention. The present invention provides an isolated polynucleotide having a promoter capable of functioning in a plant cell operably linked to a nucleic acid sequence comprising a region of between about 100 nucleic acids and about 350 nucleic acids of SEQ ID NO:1 obtained from a sequence selected from the group of nucleic acids at position 253, 353, 647, 733, 1050, 1397 and combinations thereof. The present invention also provides an isolated polynucleotide comprising a nucleic acid sequence encoding a green-leaf nicotine demethylase, where the amino acid sequence of the encoded nicotine demethylase has a substitution at an amino acid residue in a position selected from the group consisting of residues 235, 449, 174, 410, 224, 72, 143 and 422, where the numbering is according to SEQ ID NO:2. Also provided is an isolated polynucleotide comprising a promoter capable of functioning in a plant cell operably linked to a nucleic acid sequence comprising a region of between about 100 nucleic acids and about 350 nucleic acids of SEQ ID NO:4. Further provided is an isolated polynucleotide encoding an amino acid sequence as set forth in SEQ ID NO:2 with a mutation of a residue that differs from the other P450 polypeptides to a conserved residue. Alternatively provided is an isolated polynucleotide encoding an amino acid sequence as set forth in SEQ ID NO:2 with a mutation at a position selected from the group consisting of residues 85, 118, 216, 245 and 466, where the residue at 85 is not an isoleucine, the residue at 118 is not an asparagine, the residue at 216 is not tyrosine, the residue at 245 is not a tyrosine, and the residue at 466 is not valine.

In a second aspect, the present invention is summarized as an expression cassette comprising a polynucleotide encoding an amino acid sequence of SEQ ID NO:2 operably linked to a promoter that is functional in a plant cell. The present invention provides an expression cassette comprises a polynucleotide comprising a nucleic acid sequence of SEQ ID NO:3, or a fragment of at least 25 contiguous nucleic acids thereof, operably linked to a promoter that is functional in a plant cell. Also provided is an isolated polynucleotide comprising at least 25 nucleotides of a nucleic acid sequence of SEQ ID NO:3. Further provided is an isolated polypeptide comprising an amino acid sequence selected from the group consisting of SEQ ID NO:2, 5-12 and 14-24. In one embodiment of the second aspect, the isolated polypeptide comprises an amino acid sequence 99% identical to SEQ ID NO:2, such that it is capable of converting nicotine to nornicotine in green leaves of tobacco.

In a third aspect, the present invention is summarized as a plant of the genus *Nicotiana* or a plant part thereof comprising an expression cassette, the cassette encoding SEQ ID NO:2, a fragment thereof, or a complement of either. Also provided is a transgenic *Nicotiana* plant having a lower level of nicotine to nornicotine conversion rate in green leaves compared to a non-transgenic plant, the plant comprising an exogenous nucleic acid construct comprising a promoter capable of functioning in a plant cell operably linked to a polynucleotide having a first nucleic acid sequence comprising a region of between about 100 nucleic acids and about 350 nucleic acids of a green-leaf tobacco nicotine demethylase sequence encoding an amino acid sequence of SEQ ID NO:2 and a second nucleic acid sequence capable of forming a double stranded RNA with the first sequence. Further provided is a transgenic *Nicotiana* plant having a lower level of nicotine to nornicotine conversion rate in green leaves compared to a non-transgenic plant, the plant comprising an exogenous nucleic acid construct comprising a promoter capable of functioning in a plant cell operably linked to a polynucleotide having a first nucleic acid sequence comprising a region of between about 100 nucleic acids and about 350 nucleic acids of a green-leaf tobacco nicotine demethylase sequence having the nucleic acid sequence of SEQ ID NO:3 and a second nucleic acid sequence capable of forming a double stranded RNA with the first sequence is provided. Also provided is a transgenic *Nicotiana* plant having a lower level of nicotine to nornicotine conversion rate in green leaves compared to a non-transgenic plant, the plant comprising an exogenous nucleic acid construct comprising a promoter capable of functioning in a plant cell operably linked to a polynucleotide having a first nucleic acid sequence comprising a region of between about 100 nucleic acids and about 350 nucleic acids of a green-leaf tobacco nicotine demethylase sequence having a nucleic acid sequence of SEQ ID NO:4 and a second nucleic acid sequence capable of forming a double stranded RNA with the first sequence.

In a fourth aspect, the present invention is summarized as a seed of a transgenic *Nicotiana* plant having a lower level of nicotine to nornicotine conversion rate in green leaves compared to a non-transgenic plant, the plant comprising a heterologous promoter capable of functioning in a plant cell operably linked to a polynucleotide having a first nucleic acid sequence comprising a region of between about 100 nucleic acids and about 350 nucleic acids of a green-leaf tobacco nicotine demethylase sequence having an amino acid sequence of SEQ ID NO:4 and a second nucleic acid sequence capable of forming a double stranded RNA with the first sequence. Also provided is a tissue culture of regenerable tobacco cells comprising a plant cell that comprises a first polynucleotide having a fragment of the nucleic acid sequence of SEQ ID NO:1, 3 or 4 and a second polynucleotide capable of forming a double stranded RNA with the first.

In a fifth aspect, the present invention is summarized as a tobacco product comprising a transgenic *Nicotiana* plant cell having a lower level of nicotine to nornicotine conversion rate in green leaves compared to a non-transgenic plant, the plant cell comprising a heterologous promoter capable of functioning in a plant cell operably linked to a polynucleotide having a first nucleic acid sequence comprising a region of between about 100 nucleic acids and about 350 nucleic acids of a green-leaf tobacco nicotine demethylase sequence having a nucleic acid sequence of SEQ ID NO:4 and a second polynucleotide capable of forming a double stranded RNA with the first. Also provided is a tobacco cell having a genome altered to inhibit the expression of at least a green-leaf nicotine demethylase, where the cell is homozygous for a mutation in the gene encoding the green-leaf nicotine demethylase. Further provided is a tobacco cell comprising a transgene containing green-leaf nicotine demethylase nucleic acid sequence that flanks a selectable marker gene, where the selectable marker gene disrupts the nicotine demethylase gene, thereby producing a tobacco cell where the endogenous green-leaf nicotine demethylase gene has been disrupted. Alternatively provided is a tobacco cell comprising a transgene containing green-leaf nicotine demethylase nucleic acid sequence that flanks a selectable marker gene, where the selectable marker gene disrupts the nicotine demethylase gene, thereby producing a tobacco cell where the endogenous green-leaf nicotine demethylase gene has been disrupted.

In a sixth aspect, the present invention is summarized as a method for reducing nornicotine levels in a plant part derived from a plant of the genus *Nicotiana*, the method comprising a) inhibiting expression of a nicotine demethylase, where the nicotine demethylase has an amino acid sequence set forth in the group consisting of SEQ ID NOs: 2 and 5-12; and b) reducing nornicotine levels in a plant part derived from a plant of the genus *Nicotiana*. Also provided is a method for reducing nornicotine levels in a tobacco product, the method comprising a) growing a transgenic tobacco plant, where the plant having a plant part that comprises an expression cassette comprising a heterologous promoter and a nicotine demethylase, where the nicotine demethylase has an amino acid sequence selected from the group consisting of SEQ ID NOs:2 and 5-12; and b) preparing a tobacco product from the tobacco plant part. Further provided is a method for reducing nornicotine levels in a tobacco product, the method comprising a) growing a transgenic tobacco plant, where the plant has a plant part that comprises an antibody that specifically binds a polypeptide with an amino acid sequence selected from the group consisting of SEQ ID NOs:2 and 5-12; and b) preparing a tobacco product from the tobacco plant part. Alternatively provided is a method for reducing nornicotine levels in a tobacco product, the method comprising a) growing a transgenic tobacco plant, where the plant has a plant part that comprises a fragment of a green-leaf nicotine demethylase operably linked to a heterologous promoter and the fragment has at least 25 contiguous nucleic acids from a polynucleotide encoding a polypeptide selected from the group consisting of SEQ ID NOs:2 and 5-12; and b) preparing a tobacco product from the tobacco plant part. Also provided is a method for reducing nornicotine levels in a plant part derived from a plant of the genus *Nicotiana*, the method comprising a) modifying the functional CYP82E5v2 allele to change alleles to a nonfunctional CYP82E5v2, where the nonfunctional CYP82E5v2 has a substitution at an amino acid residue in a position selected from the group consisting of residues 235, 449, 174, 410, 224, 72, 143 and 422, where the numbering is according to SEQ ID NO:2; and b) reducing the level of nornicotine in a plant part derived from a plant of the genus *Nicotiana*. The present invention also provides a method for reducing the carcinogenic potential of a tobacco product, the method comprising preparing the tobacco product by a) growing a transgenic tobacco plant, where the plant comprises a plant part that comprises a fragment of a green-leaf nicotine demethylase operably linked to a heterologous promoter and the fragment comprises at least 25 contiguous nucleic acids from a polynucleotide encoding a polypeptide selected from the group consisting of SEQ ID NOs:2 and 5-12; and b) preparing a tobacco product from the tobacco plant part. Further, the present invention provides a method of reducing the conversion of nicotine to nornicotine in a *Nicotiana* plant comprising: a) transforming a *Nicotiana* plant with an nucleic acid construct comprising a promoter capable of functioning in a plant cell operably linked to a polynucleotide having a first nucleic acid sequence comprising a region of between 100 nucleic acids and about 350 nucleic acids of SEQ ID NO:1, 3 or 4 and a second nucleic acid sequence capable of forming a double stranded RNA with the first sequence; and b) regenerating a transgenic *Nicotiana* plant.

In a seventh aspect, the present invention is summarized as a method of screening for a green-leaf nicotine demethylase sequence comprising a) obtaining a nucleic acid sequence that has at least 200 nucleic acids of sequence identity with SEQ ID NO:1; and b) identifying a codon sequence encoding for a stop codon at position 422 of an encoded polypeptide, where the numbering is according to SEQ ID NO:2. Also provided is a method of screening for green-leaf nicotine demethylase sequence comprising a) obtaining a nucleic acid sequence that has at least 200 nucleic acids of sequence identity with SEQ ID NO:1; and b) identifying a codon sequence encoding for a codon that is not a proline at position 449 of an encoded polypeptide, where the numbering is according to SEQ ID NO:2. Further provided is a method for identifying a tobacco plant with low levels of nornicotine, the method comprising a) obtaining a DNA sample from a tobacco plant of interest; and b) screening the sample for a mutation in SEQ ID NO:1. The present invention also provides a method for reducing the level of nornicotine in a plant part derived from a plant of the genus *Nicotiana*, the method comprising a) inhibiting expression of a CYP82E4v2 nicotine demethylase and CYP82E5v2 nicotine demethylase; and b) reducing the level of nornicotine in a plant part derived from a plant of the genus *Nicotiana*. Also included is tobacco plant material comprising a polypeptide with an amino acid sequence of SEQ ID NO:13 having a mutation at a position selected from the group consisting of residues 458, 364, 329 and combinations thereof. Further included is tobacco plant material comprising a CYP82E4v2 having a mutation at a position selected from the group consisting of residues 458, 364, 329 and combinations thereof, where the numbering corresponds to SEQ ID NO:13. Also included is tobacco plant material comprising a CYP82E4v2 having a mutation at residue 376, where the residue is not valine and the numbering of residues corresponds to SEQ ID NO:13.

BRIEF DESCRIPTION OF DRAWINGS

FIG. 1A-C show an amino acid sequence alignment of CYP82E2 gene family members that have been assayed for nicotine demethylase activity in yeast and/or transgenic plants. Sequences in italics and underlined are positive for nicotine demethylase activity (CYP82E4v2 and CYP82E5v2); sequences titled in black failed to show activity in an assay. Residues that differ among the members are shaded in grey. In FIG. 1, CYP82E4v2 is set forth in SEQ ID NO:13; CYP82E4v6 is set forth in SEQ ID NO:26; CYP82E4v12 is set forth in SEQ ID NO:27; 58-166 is set forth in SEQ ID NO:28; CYP82E3 is set forth in SEQ ID NO:29; CYP82E2v1 is set forth in SEQ ID NO:30; CYP82E2v2 is set forth in SEQ ID NO:31; and CYP82E5v2 is set forth in SEQ ID NO:2.

DESCRIPTION OF THE NUCLEIC ACID SEQUENCES

SEQ ID NO:1 sets forth a nucleic acid sequence of a coding region of CYP82E5v2.
SEQ ID NO:2 sets forth an amino acid sequence of a CYP82E5v2.
SEQ ID NO:3 sets forth a nucleic acid sequence of an intron of CYP82E5v2.
SEQ ID NO:4 sets forth a nucleic acid sequence of a genomic CYP82E5v2.
SEQ ID NO:5 sets forth an amino acid sequence of a CYP82E5v2 P235S.
SEQ ID NO:6 sets forth an amino acid sequence of a CYP82E5v2 P449L.
SEQ ID NO:7 sets forth an amino acid sequence of a CYP82E5v2 S174L.
SEQ ID NO:8 sets forth an amino acid sequence of a CYP82E5v2 A410V.
SEQ ID NO:9 sets forth an amino acid sequence of a CYP82E5v2 M224I.
SEQ ID NO:10 sets forth an amino acid sequence of a CYP82E5v2 P72L.
SEQ ID NO:11 sets forth an amino acid sequence of a CYP82E5v2 L143F.
SEQ ID NO:12 sets forth an amino acid sequence of a CYP82E5v2 W422Stop.
SEQ ID NO:13 sets forth an amino acid sequence of a CYP82E4v2.
SEQ ID NO:14 sets forth an amino acid sequence of a CYP82E4v2 P458S.
SEQ ID NO:15 sets forth an amino acid sequence of a CYP82E4v2 K364N.
SEQ ID NO:16 sets forth an amino acid sequence of a CYP82E4v2 P38L.
SEQ ID NO:17 sets forth an amino acid sequence of a CYP82E4v2 E201K.
SEQ ID NO:18 sets forth an amino acid sequence of a CYP82E4v2 R169Q.
SEQ ID NO:19 sets forth an amino acid sequence of a CYP82E4v2 G459R.
SEQ ID NO:20 sets forth an amino acid sequence of a CYP82E4v2 E296K.
SEQ ID NO:21 sets forth an amino acid sequence of a CYP82E4v2 T427I.
SEQ ID NO:22 sets forth an amino acid sequence of a CYP82E4v2 W329Stop.
SEQ ID NO:23 sets forth an amino acid sequence of a CYP82E4v2 V376M.
SEQ ID NO:24 sets forth an amino acid sequence of a CYP82E4v2 D171N.
SEQ ID NO:25 sets forth an amino acid sequence of a CYP82E4.
SEQ ID NO:26 sets forth an amino acid sequence of a CYP82E4v6.
SEQ ID NO:27 sets forth an amino acid sequence of a CYP82E4v12.
SEQ ID NO:28 sets forth an amino acid sequence of a 58-166.
SEQ ID NO:29 sets forth an amino acid sequence of a CYP82E3.
SEQ ID NO:30 sets forth an amino acid sequence of a CYP82E2v1.
SEQ ID NO:31 sets forth an amino acid sequence of a CYP82E2v2.
SEQ ID NO:32 sets forth a nucleic acid sequence of a forward primer for exon 1 of CYP82E4v2.
SEQ ID NO:33 sets forth a nucleic acid sequence of a reverse primer for exon 1 of CYP82E4v2.
SEQ ID NO:34 sets forth a nucleic acid sequence of a forward primer for exon 2 of CYP82E4v2.
SEQ ID NO:35 sets forth a nucleic acid sequence of a reverse primer for exon 2 of CYP82E4v2.
SEQ ID NO:36 sets forth a nucleic acid sequence of a forward primer for exon 1 of CYP82E5v2.
SEQ ID NO:37 sets forth a nucleic acid sequence of a reverse primer for exon 1 of CYP82E5v2.
SEQ ID NO:38 sets forth a nucleic acid sequence of a forward primer for exon 2 of CYP82E5v2.
SEQ ID NO:39 sets forth a nucleic acid sequence of a reverse primer for exon 2 of CYP82E5v2.
SEQ ID NO:40 sets forth a nucleic acid sequence of a primer E5Gen_F1.
SEQ ID NO:41 sets forth a nucleic acid sequence of a primer E5Gen_R1.
SEQ ID NO:42 sets forth a nucleic acid sequence of a primer E5Gen_F2.
SEQ ID NO:43 sets forth a nucleic acid sequence of a primer E5Gen_R2.
SEQ ID NO:44 sets forth a nucleic acid sequence of a primer E4Rt_F.
SEQ ID NO:45 sets forth a nucleic acid sequence of a primer E4Rt_R.
SEQ ID NO:46 sets forth a nucleic acid sequence of a primer E5Rt_F.

SEQ ID NO:47 sets forth a nucleic acid sequence of a primer E5Rt_R.

SEQ ID NO:48 sets forth a nucleic acid sequence of a primer G3PDH_F.

SEQ ID NO:49 sets forth a nucleic acid sequence of a primer G3PDH_R.

SEQ ID NO:50 sets forth a nucleic acid sequence of a coding region of CYP82E4v2 and the encoded protein (i.e., SEQ ID NO:13).

Definitions

The present invention includes compositions and methods for inhibiting expression or function of nicotine demethylase polypeptides that are involved in the metabolic conversion of nicotine to nornicotine in a plant, particularly plants of the *Nicotiana* genus, including tobacco plants of various commercial varieties.

As used herein, "inhibit," "inhibition" and "inhibiting" are defined as any method known in the art or described herein, which decreases the expression or function of a gene product of interest (i.e., the target gene product).

"Inhibiting" can be in the context of a comparison between two plants, for example, a genetically altered plant versus a wild-type plant. The comparison can be between plants, one of which lacks a DNA sequence capable of reducing the agent. Inhibition of expression or function of a target gene product also can be in the context of a comparison between plant cells, organelles, organs, tissues or plant parts within the same plant or between different plants, and includes comparisons between developmental or temporal stages within the same plant or plant part or between plants or plant parts.

"Inhibiting" can include any relative decrement of function or production of a gene product of interest, up to and including complete elimination of function or production of that gene product. When levels of an agent are compared, such a comparison is preferably carried out between organisms with a similar genetic background. Preferably, a similar genetic background is a background where the organisms being compared share 50% or greater, more preferably 75% or greater, and, even more preferably 90% or greater sequence identity of nuclear genetic material. A similar genetic background is a background where the organisms being compared are plants, and the plants are isogenic except for any genetic material originally introduced using plant transformation techniques or a mutation generated by human intervention. Measurement of the level or amount of an agent may be carried out by any suitable method, non-limiting examples of which include, but are not limited to, comparison of mRNA transcript levels, protein or peptide levels, and/or phenotype, especially the conversion of nicotine to nornicotine. As used herein, mRNA transcripts can include processed and non-processed mRNA transcripts, and polypeptides or peptides can include polypeptides or peptides with or without any post-translational modification.

As used herein, "host cell" means a cell that comprises a heterologous nucleic acid sequence of the invention. Though the nucleic acid sequences of the invention, and fragments and variants thereof, can be introduced into any cell of interest, of particular interest are plant cells, more particularly cells of a *Nicotiana* plant species, for example, the tobacco plant species and varieties described herein below.

As used herein, "variant" means a substantially similar sequence. A variant can have different function or a substantially similar function as a wild-type polypeptide of interest. For a nicotine demethylase, a substantially similar function is at least 99%, 98%, 97%, 95%, 90%, 85%, 80%, 75%, 60%, 50%, 25% or 15% of wild-type enzyme function of converting nicotine to nornicotine under the same conditions or in a near-isogenic line. A wild-type CYP82E5v2 is SEQ ID NO:2. A wild-type CYP82E4v2 is SEQ ID NO:13. As used herein, a "variant polynucleotide" or "variant polypeptide" means a nucleic acid or amino acid sequence that is not wild-type.

A variant can have one addition, deletion or substitution; two or less additions, deletions or substitutions; three or less additions, deletions or substitutions; four or less additions, deletions or substitutions; or five or less additions, deletions or substitutions. A mutation includes additions, deletions, and substitutions. Such deletions or additions can be at the C-terminus, N-terminus or both the C- and N-termini. Fusion polypeptides or epitope-tagged polypeptides are also included in the present invention. "Silent" nucleotide mutations do not change the encoded amino acid at a given position. Amino acid substitutions can be conservative. A conservative substitution is a change in the amino acid where the change is to an amino acid within the same family of amino acids as the original amino acid. The family is defined by the side chain of the individual amino acids. A family of amino acids can have basic, acidic, uncharged polar or nonpolar side chains. See, Alberts et al., (1994) *Molecular biology of the cell* (3rd ed., pages 56-57, Garland Publishing Inc., New York, N.Y.), incorporated herein by reference as if set forth in its entirety. A deletion, substitution or addition can be to the amino acid of another CYP82E family member in that same position. See, FIG. 1A-C. As used herein, a "fragment" means a portion of a polynucleotide or a portion of a polypeptide and hence protein encoded thereby.

As used herein, "plant part" means plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the present invention, provided that they comprise the introduced polynucleotides of the invention. As used herein, "tobacco plant material" means any portion of a plant part or any combination of plant parts.

As used herein, "operably linked" means a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the fusing of two protein coding regions, by operably linked is intended that the coding regions are in the same reading frame.

As used herein, "heterologous" means a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Furthermore, as used herein, "chimeric gene" means a coding sequence operably linked to a transcription initiation region that is heterologous to the coding sequence.

DETAILED DESCRIPTION OF THE INVENTION

Nicotine Demethylase Polynucleotides and Polypeptides, and Variants and Fragments Thereof Compositions of the present invention include cytochrome P450 polypeptides. Cytochrome P450 polypeptides can have nicotine demethylase activity. Such nicotine demethylase polynucleotides and polypeptides are involved in the metabolic conversion of nicotine to nornicotine in plants, including commercial varieties of tobacco plants. Also included are variants of such nicotine demethylases. In particular, compositions of the invention include isolated polypeptides comprising amino acid sequences as shown in SEQ ID NOS:2 and 5-24, isolated polynucleotides comprising the nucleic acid sequences as shown in SEQ ID NOS:1, 3 and 4, and the isolated polynucleotides encoding polypeptides comprising amino acid sequences of SEQ ID NOS:2 and 5-24. The polynucleotides of the present invention can find use in inhibiting expression of nicotine demethylase polypeptides or variants thereof that are involved in the metabolic conversion of nicotine to nornicotine in plants, particularly tobacco plants. Some of the polynucleotides of the invention have mutations that inhibit nicotine demethylase activity of the wild-type nicotine demethylase. The inhibition of polypeptides of the present invention is effective in lowering nornicotine levels in tobacco lines where genetic conversion occurs in less than 30%, 50%, 70% and 90% of the population, such as flue-cured tobaccos. The inhibition of polypeptides of the present invention is effective in lowering nornicotine levels in tobacco populations where genetic conversion occurs in at least 90%, 80%, 70%, 60% and 50% of a plant population. A population preferably contains greater than about 25, 50, 100, 500, 1,000, 5,000 or 25,000 plants where, more preferably at least about 10%, 25%, 50%, 75%, 95% or 100% of the plants comprise a polypeptide of the present invention.

The present invention further provides expression cassettes comprising all or a portion of the polynucleotides having a nucleic acid sequence set forth in SEQ ID NO:1, 3 or 4, and the isolated polynucleotides encoding polypeptides having an amino acid sequence of SEQ ID NOS: 2 and 5-24, a complement or fragment thereof, or a sequence having substantial sequence identity to SEQ ID NO:1, 3 or 4, or the polynucleotides encoding polypeptides having an amino acid sequence of SEQ ID NOS:2 and 5-24, or a complement or fragment thereof, operably linked to a heterologous promoter that is functional in a plant cell for use in expressing an inhibitory RNA transcript that interferes with expression (i.e., transcription and/or translation) of nicotine demethylase polypeptides. In some embodiments, the expression cassettes comprise the nucleotide sequence as shown in SEQ ID NO:1, 3 or 4, a complement or fragment thereof, or a sequence having substantial sequence identity to SEQ ID NO:1, 3 or 4, or a complement or fragment thereof. Introduction of these expression cassettes into a Nicotiana plant of interest; particularly a tobacco plant of varieties commonly known as flue or bright varieties, Burley varieties, dark varieties and oriental/Turkish varieties, results in the production of tobacco plants having reduced amounts of nornicotine and NNN. Leaf and stem material from these transgenic plants can be used to produce a variety of tobacco products having, reduced levels of nornicotine, and a concomitant reduction NNN.

The nicotine demethylase polynucleotides and encoded polypeptides of the present invention include a novel cytochrome P450 gene, designated the CYP82E5v2 nicotine demethylase gene, that is newly identified as having a role in the metabolic conversion of nicotine to nornicotine in tobacco plants. Suppression of the expression of the encoded polypeptide in transgenic tobacco plants results in a significant reduction in the accumulation of nornicotine in the green leaves of these transgenic plants. While not being bound by theory, the metabolic role of these polypeptides may be a direct one, i.e., directly catalyzing the N-demethylation reaction, or an indirect one, i.e., in the form of production of a product that leads to the up-regulation of the nicotine demethylase activity of the leaf. Regardless of the mechanism, any means by which expression and/or function of the polypeptides of the present invention are targeted for inhibition or site-directed mutagenesis within a Nicotiana plant will be effective in reducing nornicotine levels, and levels of NNN, within leaves and stems of these plants.

The invention encompasses isolated or substantially purified polynucleotide or polypeptide compositions of the present invention. An "isolated" or "purified" polynucleotide or polypeptide, or biologically active portion thereof, is substantially or essentially free from components that normally accompany or interact with the polynucleotide or protein as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A polypeptide that is substantially free of cellular material includes preparations having less than about 30%, 20%, 10%, 5% or 1% (by dry weight) of contaminating protein. When the polypeptide of the invention or biologically active portion thereof is recombinantly produced, optimally culture medium represents less than about 30% 20%, 10%, 5% or 1% (by dry weight) of chemical precursors or non-protein-of-interest chemicals.

Fragments of the disclosed polynucleotides and polypeptides encoded thereby are also encompassed by the present invention. Fragments of a polynucleotide may encode polypeptide fragments that retain the biological activity of the native polypeptide and hence are involved in the metabolic conversion of nicotine to nornicotine in a plant. Alternatively, fragments of a polynucleotide that are useful as hybridization probes or PCR primers using methods described below generally do not encode fragment polypeptides retaining biological activity. Furthermore, fragments of the disclosed polynucleotides include those that can be assembled within recombinant constructs for use in gene silencing with any method known in the art, including, but not limited to, sense suppression/cosuppression, antisense suppression, double-stranded RNA (dsRNA) interference, hairpin RNA interference and intron-containing hairpin RNA interference, amplicon-mediated interference, ribozymes and small interfering RNA or micro RNA, as described in the art and herein below. Thus, fragments of a polynucleotide may range from at least about 20 nucleotides, about 50 nucleotides, about 70 nucleotides, about 100 nucleotides about 150 nucleotides, about 200 nucleotides, 250 nucleotides, 300 nucleotides and up to the full-length polynucleotide encoding the polypeptides of the invention, depending upon the desired outcome. For example, the fragments of a polynucleotide can be between 100 and about 350 nucleotides, between 100 and about 325 nucleotides, between 100 and about 300 nucleotides, between about 125 and about 300 nucleotides, between about 125 and about 275 nucleotides in length, between about 200 to about 320 contiguous nucleotides, between about 200 and about 420 contiguous nucleotides in length between about 250 and about 450 contiguous nucleotides in length. Alternatively, the fragment can be between about 300 and about 450 contiguous nucleotides in length.

A fragment of a nicotine demethylase polynucleotide of the present invention that encodes a biologically active portion of a cytochrome P450 polypeptide of the present invention will encode at least 15, 25, 30, 50, 75, 100, 125, 150, 175, 200, 250, 300, 350, 400, 450 or 500 contiguous amino acids, or up to the total number of amino acids present in a full-length nicotine demethylase polypeptide of the invention (e.g., 517 amino acids for SEQ ID NOS:2 and 5), or will encode at least 15, 25, 30, 50, 75, 100, 125, 150 or up to the total number of amino acids present in a partial-length cytochrome P450 polypeptide of the invention (e.g., 422 for SEQ ID NO:12). Preferably, the fragment comprises up to amino acid residue 330 of the encoded polypeptide. A biologically active portion of a nicotine demethylase polypeptide can be prepared by isolating a portion of one of the cytochrome P450 polynucleotides of the present invention, expressing the encoded portion of the cytochrome P450 polypeptide (e.g., by recombinant expression in vitro), and assessing the activity of the encoded portion of the cytochrome P450 polypeptide, i.e., the ability to promote conversion of nicotine to nornicotine, using assays known in the art and those provided herein below.

Polynucleotides that are fragments of a cytochrome P450 nucleotide sequence of the present invention comprise at least 16, 20, 50, 75, 100, 150, 200, 250, 300, 350, 400, 450, 500, 550, 600, 650, 700, 800, 900, 950, 1000, 1050, 1100, 1150, 1200, 1250, 1300, 1350, 1400, 1450, 1500, 1550, 1600, 1650 or 1700 contiguous nucleic acids, or up to the number of nucleotides present in a full-length cytochrome P450 polynucleotide as disclosed herein (e.g., 1554 for SEQ ID NO:1; or 2608 for SEQ ID NO:4). Polynucleotides that are fragments of a cytochrome P450 nucleotide sequence of the present invention comprise fragments from about 20 to about 1700 contiguous nucleic acids, from about 50 to about 1600 contiguous nucleic acids, from about 75 to about 1500 contiguous nucleic acids, from about 100 to about 1400 nucleic acids, from about 150 to about 1300 contiguous nucleic acids, from about 150 to about 1200 contiguous nucleic acids, from about 175 to about 1100 contiguous nucleic acids, from about 200 to about 1000 contiguous nucleic acids, from about 225 to about 900 contiguous nucleic acids, from about 500 to about 1600 contiguous nucleic acids, from about 775 to about 1700 contiguous nucleic acids, from about 1000 to about 1700 contiguous nucleic acids, or from about 300 to about 800 contiguous nucleic acids from a cytochrome P450 polynucleotide as disclosed herein. For example, polynucleotide fragment can comprise a polynucleotide sequence containing the nucleic acid sequence from the polynucleotide at about position 700 to about position 1250 of a cytochrome P450 coding sequence, at about position 700 to about position 1250 of a cytochrome P450 genomic sequence, at about position 10 to about position 900 of a cytochrome P450 intron sequence, or at about position 100 to about position 800 of a cytochrome P450 intron sequence.

Variants of the disclosed polynucleotides and polypeptides encoded thereby are also encompassed by the present invention. Naturally occurring variants include those variants that share substantial sequence identity to the disclosed cytochrome P450 polynucleotides and polypeptides disclosed herein. Naturally occurring variants can share substantial functional identity to the disclosed cytochrome P450 polynucleotides disclosed herein. The compositions and methods of the invention can be used to target expression or function of any naturally occurring cytochrome P450 that shares substantial sequence identity to the disclosed cytochrome P450 polypeptides. Such cytochrome P450 can possess the relevant cytochrome P450 activity, i.e., involvement in the metabolic conversion of nicotine to nornicotine in plants, or not. Such variants may result from, e.g., genetic polymorphism or from human manipulation as occurs with breeding and selection. Biologically active variants of a cytochrome P450 protein of the invention, such as variants of the polypeptide set forth in SEQ ID NO:2 and 5-24, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the wild-type protein as determined by sequence alignment programs and parameters described elsewhere herein, and can be characterized by a functional involvement in the metabolic conversion of nicotine to nornicotine in plants or lack thereof. A biologically active variant of a polypeptide of the invention may differ by as few as 1-15 amino acid residues, as few as 10, as few as 9, as few as 8, as few as 7, as few as 6, as few as 5, as few as 4, as few as 3, as few as 2, or as few as 1 amino acid residue from the wild-type polypeptide. A biologically inactive variant of a protein of the invention may differ from that polypeptide by as few as 1-15 amino acid residues, as few as 10, as few as 9, as few as 8, as few as 7, as few as 6, as few as 5, as few as 4, as few as 3, as few as 2, or as few as 1 amino acid residue.

Variants of the polynucleotides of the present invention include those naturally occurring polynucleotides that encode a nicotine demethylase polypeptide that is involved in the metabolic conversion of nicotine to nornicotine in plants. Such polynucleotide variants can comprise a deletion and/or addition of one or more nucleotides at one or more sites within the native polynucleotide disclosed herein and/or a substitution of one or more nucleotides at one or more sites in the native polynucleotide. Because of the degeneracy of the genetic code, conservative variants for polynucleotides include those sequences that encode the amino acid sequence of one of the cytochrome P450 polypeptides of the invention. Naturally occurring variants such as these can be identified with the use of well-known molecular biology techniques, as, e.g., with polymerase chain reaction (PCR) and hybridization techniques as are known in the art and disclosed herein. Variant polynucleotides also include synthetically derived polynucleotides, such as those generated, e.g., by using site-directed mutagenesis but which still share substantial sequence identity to the naturally occurring sequences disclosed herein, and thus can be used in the methods of the invention to inhibit the expression or function of a nicotine demethylase that is involved in the metabolic conversion of nicotine to nornicotine, including the nicotine demethylase polypeptides set forth in SEQ ID NOS:2, 5, 7-11, 13, 16-21 and 23-24. Generally, variants of a particular polynucleotide of the invention, e.g., the polynucleotide sequence of SEQ ID NO:3 or the polynucleotide sequence encoding the amino acid sequence set forth in SEQ ID NO:2 and 5-24, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the present invention (also referred to as the reference polynucleotide) can also be evaluated by comparison of the percent sequence identity between the polypeptide encoded by the reference polynucleotide and the polypeptide encoded by a variant polynucleotide. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity. A variant polypeptide of the present invention can include a polypeptide having a serine at position 458, an asparagine at position 364 of the cytochrome P450 polypeptide, a stop codon at position 329 of the cytochrome P450 or any combination thereof, where the numbering corresponds to SEQ ID NO:13.

Furthermore, the polynucleotides of the invention can be used to isolate corresponding cytochrome P450 sequences from other organisms, particularly other plants, more particularly other members of the *Nicotiana* genus. PCR, hybridization and other like methods can be used to identify such sequences based on their sequence homology to the sequences set forth herein. Sequences isolated based on their sequence identity to the nucleotide sequences set forth herein or to variants and fragments thereof are encompassed by the present invention. Such sequences include sequences that are orthologs of the disclosed sequences.

As used herein, "orthologs" means genes derived from a common ancestral gene that are found in different species as a result of speciation. Genes found in different species are considered orthologs when their nucleotide sequences and/ or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode for a nicotine demethylase polypeptide that is involved in the nicotine-to-nornicotine metabolic conversion and which hybridize under stringent conditions to the cytochrome P450 sequences disclosed herein, or to variants or fragments thereof, are encompassed by the present invention. Such sequences can be used in the methods of the present invention to inhibit expression of nicotine demethylase polypeptides that are involved in the metabolic conversion of nicotine to nornicotine in plants.

Using PCR, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular cloning: a laboratory manual* (2d ed, Cold Spring Harbor Laboratory Press, Plainview, N.Y.). Innis et al., eds. (1990) *PCR protocols: a guide to methods and applications* (Academic Press, New York); Innis & Gelfand, eds. (1995) *PCR strategies* (Academic Press, New York); and Innis & Gelfand, eds. (1999) *PCR methods manual* (Academic Press, New York). Known methods of PCR include, but are not limited to, methods using paired primers, nested primers, single specific primers, degenerate primers, gene-specific primers, vector-specific primers, partially mismatched primers and the like.

Hybridization techniques involve the use of all or part of a known polynucleotide as a probe that selectively hybridizes to other corresponding polynucleotides present in a population of cloned genomic DNA fragments or cDNA fragments (i.e., genomic or cDNA libraries) from a chosen organism.

Hybridization may be carried out under stringent conditions. As used herein, "stringent conditions" or "stringent hybridization conditions" means conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleic acids in length, optimally less than 500 nucleic acids in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl 1% SDS at 37° C., and a wash in 0.5× to 1× SSC at 55 to 60° C. Exemplary high stringency conditions include hybridization in 50% formamide, 1 M NaCl, 1% SDS at 37° C. and a wash in 0.1× SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Preferably, stringency conditions include hybridization in a solution containing 5× SSC, 0.5% SDS, 5×Denhardt's, 0.45 ug/ul poly A RNA, 0.45 ug/ul calf thymus DNA and 50% formamide at 42° C., and at least one post-hybridization wash in a solution comprising from about 0.01× SSC to about 1× SSC. The duration of hybridization is from about 14 to about 16 hours.

Specificity is typically the function of post-hybridization washes, the critical factors being the ionic strength and temperature of the final wash solution. For DNA-DNA hybrids, the $T_m$ can be approximated from the equation of Meinkoth & Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However; severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$, of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory techniques in biochemistry and molecular biology-hybridization with nucleic acid probes*, Part I, Chapter 2 (Elsevier, New York); and Ausubel et al., eds. (1995) *Current protocols in molecular biology, Chapter 2* (Greene Publishing and Wiley-Interscience, New York). See also, Sambrook et al. (1989) *Molecular cloning: a laboratory manual* (2d ed., Cold Spring Harbor Laboratory Press, Plainview, N.Y.).

Hybridization probes may be genomic DNA fragments, cDNA fragments, RNA fragments or other oligonucleotides, and may be labeled with a detectable group such as $^{32}P$, or any other delectable marker. For example, probes for hybridization can be made by labeling synthetic oligonucleotides based on the cytochrome P450 polynucleotides sequences of the present invention. Methods for preparation of probes for hybridization and for construction of cDNA and genomic libraries are generally known in the art and are disclosed in Sambrook et al., supra.

For example, the cytochrome P430 polynucleotides disclosed herein, or one or more portions thereof, may be used as probes capable of specifically hybridizing to corresponding cytochrome P450 polynucleotides and messenger RNAs. To achieve specific hybridization under a variety of conditions, such probes include sequences that are unique among cytochrome P450 polynucleotide sequences or unique to one of the cytochrome P450 polynucleotide sequences, including upstream regions 5' to the coding sequence and downstream regions 3' to the coding sequence and an intron region, and are optimally at least about 10 contiguous nucleotides in length, more optimally at least about 20 contiguous nucleic acids in length, more optimally at least about 50 contiguous nucleic acids in length, more optimally at least about 75 contiguous nucleic acids in length, and more optimally at least about 100 contiguous nucleic acids in length. Such probes may be used to amplify corresponding cytochrome P450 polynucleotides. This technique may be used to isolate additional coding sequences or mutations from a desired plant or as a diagnostic assay to determine the presence of coding sequences in a plant. Hybridization techniques include hybridization screening of plated DNA libraries (either plaques or colonies; see, e.g., Sambrook et al., supra.

As used herein, with respect to the sequence relationships between two or more polynucleotides or polypeptides, the term "reference sequence" means a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means a contiguous and specified segment of a polynucleotide sequence, where the polynucleotide sequence in the comparison window may comprise additions or deletions (i.e., gaps) compared to the reference sequence (which does not comprise additions or deletions) for optimal alignment of the two polynucleotides. Generally, a comparison window is at least 20 contiguous nucleic acids in length, and optionally can be 30, 40, 50 or 100 contiguous nucleic acids or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers & Miller (1988) *CABIOS* 4:11-17; the local alignment algorithm of Smith et al. (1981) *Adv. Appl. Math.* 2:482; the global alignment algorithm of Needleman & Wunsch (1970) *J. Mol. Biol.* 48:443-453; the search-for-local alignment method of Pearson & Lipman (1988) *Proc. Natl. Acad. Sci.* 85:2444-2448; the algorithm of Karlin & Altschul (1990) *Proc. Natl. Acad. Sci. USA* 872264, modified as in Karlin & Altschul (1993) *Proc. Natl. Acad. Sci. USA* 90:5873-5877.

The BLAST programs of Altschul et al. (1990) *J. Mol. Biol.* 215:403 are based on the algorithm of Karlin & Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50. wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used (See www.ncbi.nlna.nih.gov). Alignment may also be performed manually by inspection.

The sequence identity/similarity values provided herein were calculated using the BLASTX (Altschul et al. (1997) supra), Clustal W (Higgins et al. (1994) *Nucleic Acids Res.* 22:4673-4680), and GAP (University of Wisconsin Genetic Computing Group software package) algorithms using default parameters. The present invention also encompasses the use of any equivalent program thereof for the analysis and comparison of nucleic acid and protein sequences. By "equivalent program" is intended any sequence comparison program that, for any two sequences in question, generates an alignment having identical nucleotide or amino acid residue matches and an identical percent sequence identity when compared to the corresponding alignment generated by BLASTX. Clustal W, or GAP.

For purposes of the foregoing discussion of variant nucleotide and polypeptide sequences encompassed by the present invention, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for malting this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics; Mountain View, Calif.).

As used herein, "percentage of sequence identity" means the value determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Thus, cytochrome P450 polynucleotide and polypeptide sequences can be identified using the sequences provided herein. Such methods include obtaining a polynucleotide or polypeptide sequence at least 80%, 85%, 90%, 95%, 98% or 99% sequence identity with the polynucleotide sequence of SEQ ID NO:1, 3 or 4 or a complement or fragment thereof, or a polypeptide sequence of SEQ ID NO:2 or 5-24. A preferred embodiment includes a polypeptide corresponding to SEQ ID NO:13 that has a serine at position 458 or an asparagine at position 364 of the cytochrome P450 polypeptide, or a stop codon at position 329 of the cytochrome P450, or a combination thereof, where the numbering corresponds to SEQ ID NO:13.

Expression Cassettes for Use in the Methods of Invention

Compositions of the present invention further include expression cassettes comprising inhibitory sequences capable of inhibiting expression or function of a nicotine demethylase polypeptide involved in the conversion of nicotine to nornicotine in a *Nicotiana* plant or plant part thereof, where the inhibitory sequences are operably linked to a promoter that is functional in a plant cell. In this manner, expression cassettes comprising all or part of the sequence set forth in SEQ ID NO:1, 3 or 4 or encoding SEQ ID NO:2 or 5-24, a complement or fragment thereof, or sequences sharing substantial sequence identity to such sequences, or a complement or fragment thereof, operably linked to a promoter that is functional in a plant cell are constructed for use in the gene-silencing methods of the present invention described herein below. Such sequences are referred to herein as "inhibitory sequences" or "inhibitory polynucleotide sequences," as they are capable of being expressed as an RNA molecule that inhibits expression (i.e., transcription and/or translation) of the target cytochrome P450 polypeptide, for example, the polypeptide set forth in SEQ ID NO:2 or 5-24 and variants thereof, where the variant polypeptides have substantial sequence identity to these disclosed cytochrome P450 polypeptides. Such variants may or may not be involved in the metabolic conversion of nicotine to nornicotine in a plant. Such sequences also include fragment sequences of the target cytochrome P450 polynucleotide or polypeptide. For example, a fragment sequence can include any portion of the cytochrome P450 sequence, including coding and non-coding sequence (e.g., 5' UTR, intron, and 3' UTR sequences), and can include fragments between 100 and about 350 nucleic acids, between about 125 and about 300 nucleic acids, or between about 125 and about 275 nucleic acids. Preferably, a fragment of nicotine demethylase can be between about 20 and about 420, about 30 and about 420, between about 40 and about 320, between about 50 and about 200, between about 50 and about 400, between about 50 and about 420, between about 60 and about 320, about 70 and about 220, between about 100 and about 200, between about 100 and about 320, between about 150 and about 200, between about 150 and about 220, between about 150 and about 400, between about 200 and about 300, or between about 300 and about 400 contiguous nucleic acids. Alternatively, a fragment of a cytochrome P450 can be about 100, about 150, about 200, about 220, about 250, about 300, about 320, or about 350 contiguous nucleic acids in length. Alternatively yet, a cytochrome P450 fragment can be reduced in length by about 20, about 40, about 60, about 80, about 100, about 120, about 140, about 160, about 180, about 200, about 220, about 240, about 260, about 280, about 290, about 300, about 320, about 340, about 360, about 380, about 400 contiguous nucleic acids compared to the full-length. For all of these cytochrome P450 fragments, the truncation or deletion can start at the 5' end, start at the 3' end, or be internal to a cytochrome P450 or a cytochrome P450 intron. For a cytochrome P450 intron fragment, the entire sequence of a cytochrome P450 intron can be SEQ ID NO:3.

Furthermore, a fragment of a cytochrome P450 polynucleotide or polypeptide can contain contiguous nucleotides from about 1, 2, 5, 10, 20, 30, 40, 50, 60, 70, 80, or 90% of the entire gene. Alternatively stated, a fragment of a cytochrome P450 polynucleotide or polypeptide can be between about 5%-about 80%, between about 10%-about 70%, between about 10%-about 60%, between about 10%-about 50%, between about 25%-about 60%, between about 25%-about 50%, between about 40%-about 60%, between about 40%-about 80%, between about 50%-about 90% of the length of an entire cytochrome P450.

Expression cassettes of the present invention include those that encompass additional domains that modulate the level of expression, the developmental timing of expression, or tissue type that expression occurs in (e.g., AU Patent No. AU-A-77751/94 and U.S. Pat. Nos. 5,466,785 and 5,635,618). Promoters can be selected based on the desired outcome. The nucleic acids of the present invention can be combined with inducible, constitutive, pathogen- or wound-induced, environmentally- or developmentally-regulated, cell- or tissue-preferred promoter, or other promoters for expression in plants.

Chemical-inducible promoters can be used to inhibit the expression of a cytochrome P450 that is involved in the metabolic conversion of nicotine to nornicotine in a plant through the application of an exogenous chemical regulator. Chemical-inducible promoters are known in the art and include, but are not limited to, the tobacco PR-la promoter, which is activated by salicylic acid. Other chemical-inducible promoters of interest include steroid-responsive promoters (see, e.g., the glucocorticoid-inducible promoter (Schena et al. (1991) *Proc. Natl. Acad. Sci. USA* 88:10421-10425; and McNellis et al. (1998) *Plant J.* 14(2):247-257) and tetracycline-inducible promoters (see, e.g., Gatz et al. (1991) *Mol. Gen. Genet.* 227:229-237; and U.S. Pat. Nos. 5,814,618 and 5,789,156), each of which is incorporated herein by reference as if set forth in its entirety.

Constitutive promoters include, e.g., the core promoter of the Rsyn7 promoter and outer constitutive promoters disclosed in U.S. Pat. No. 6,072,050; the core CaMV 35S promoter (Odell et al. (1985) *Nature* 313:810-812); ubiquitin (Christensen et al. (1989) *Plant Mol. Biol.* 12:619-632; and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, e.g., those disclosed in U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target expression of an inhibitory polynucleotide sequence of the present invention within a particular plant tissue. Tissue-preferred promoters include those disclosed in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

Of particular interest herein are leaf preferred promoters that provide for expression predominately in leaf tissues. See, e.g., Yamamoto et al. (1997) *Plant* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; Baszczynski et al. (1988) *Nucl. Acid Res.* 16:4732; Mitra et al. (1994) *Plant Molecular Biology* 26:35-93; Kayaya et al. (1995) *Molecular and General Genetics* 248:668-674; and Matsuoka et al. (1993) *Proc. Natl. Acad. Sci. USA* 90(20):9586-9590. Senecence-regulated et al. (1998) *Plant Physiol.* 116:329-335); SAG 13 (Gan and Amasino (1997) *Plant Physiol.* 113:313-319; SAG 15 (Gan (1995) "Molecular Characterization and Genetic Manipulation of Plant Senescence," Ph.D. Thesis, University of Wisconsin, Madison); SENT (Oh et al. (1996) *Plant Mol. Biol.* 30:739-754; promoter of a senescence-specific gene for expression of IPT (Gan and Amasino 91995) *Science* 270:1986-1988); and the like (see, e.g., Or et al. (1999) *Plant Cell* 11:1073-1080; and McCabe et al. (2001) *Plant Physiol.* 127:505-516).

Expression cassettes of the present invention can include 5' leader sequences that can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acid. Sci. USA* 86:6126-6130); potyvirus leaders, e.g., TEV leader (Tobacco Etch Virus; Gallie et al. (1995) *Gene* 165(2):233-238), MDMV leader (Maize Dwarf Mosaic Virus; *Virology* 154:9-20), and human immunoglobulin heavy-chain binding protein (BiP; Macejak et al. (1991) *Nature* 353:90-94); untranslated leader from the coat protein mRNA of alfalfa mosaic virus (AMV RNA 4; Jobling et al. (1987) *Nature* 325:622-625); tobacco mosaic virus leader (TMV; Gallie et al. (1989) in *Molecular biology of RNA*, ed. Cech (Liss, New York), pp. 237-256); and maize chlorotic mottle virus leader (MCMV; Lommel et al. (1991) *Virology* 81:382-385). See also, Della-Cioppa et al. (1987) *Plant Physiol.* 84:965-968. Other methods known to enhance translation also can be utilized.

Methods for Inhibiting Expression or Function of a Nicotine Demethylase

Methods of reducing the concentration, content and/or activity of a cytochrome P450 polypeptide of the present invention in a *Nicotiana* plant or plant part, particularly the leaf tissue, are provided. Many methods may be used, alone or in combination, to reduce or eliminate the activity of a cytochrome P450 polypeptide of the present invention, more particularly, the CYP82E5v2 nicotine demethylase. In addition, combinations of methods may be employed to reduce or eliminate the activity of two or more different cytochrome P450 polypeptides, more particularly the CYP82E5v2 and CYP82E4v2 nicotine demethylases. Preferably, the CYP82E5v2 is a polypeptide with at least one amino acid mutation in SEQ ID NO:2 that negatively affects conversion in green leaves and the CYP82E4v2 has the sequence set forth in SEQ ID NO:13 with at least one amino acid mutation that negatively affects conversion in senescent leaves.

In accordance with the present invention, the expression of a cytochrome P450 polypeptide of the present invention is inhibited if the protein level of the cytochrome P450 polypeptide is statistically lower than the protein level of the same cytochrome P450 polypeptide in a plant that has not been genetically modified or mutagenized to inhibit the expression of that cytochrome P450 polypeptide, and where these plants have been cultured and harvested using the same protocols. In particular embodiments of the invention, the protein level of the cytochrome P450 polypeptide in a modified plant according to the invention is less than 95%, less than 90%, less than 80%, less than 70%, less than 60%, less than 50%, less than 40%, less than 30%, less than 20%, less than 10%, or less than 5% of the protein level of the same cytochrome P450 polypeptide in a plant that is not a mutant or that has not been genetically modified to inhibit the expression of that cytochrome P450 polypeptide and which has been cultured and harvested using the same protocols. The expression level of the cytochrome P450 polypeptide may be measured directly, for example, by assaying for the level of the cytochrome P450 transcript or cytochrome P450 polypeptide expressed in the *Nicotiana* plant or plant part, or indirectly, e.g., by measuring the conversion of nicotine to nornicotine in the *Nicotiana* plant or plant part. Methods for monitoring expression level of a polypeptide are known in the art, and include, but are not limited to, Northern blot analysis and RNA differentiation assays. Methods for determining the activity of a targeted cytochrome P450 polypeptide in converting nicotine to nornicotine are known in the art and described elsewhere herein below, and include, but are not limited to, alkaloid analysis using gas chromatography.

In some instances, the activity of one or more cytochrome P450 polypeptides is reduced or eliminated by transforming a plant or plant part with an expression cassette comprising a polynucleotide encoding a polypeptide that inhibits the activity of one or more cytochrome P450 polypeptides of the present invention. A number of approaches have been used to combine transgenes or mutations in one plant—including sexual crossing, retransformation, co-transformation and the use of linked transgenes. A chimeric transgene with linked partial gene sequences can be used to coordinately suppress numerous plant endogenous genes. Constructs modeled on viral polyproteins can be used to simultaneously introduce multiple coding genes into plant cells. For a review, see Halpin et al., *Plant Mol. Biol.* 47:295-310 (2001). A plant having a mutation in CYP82E4v2 that inhibits the nicotine demethylase activity in senescent leaves can be crossed with a plant having a mutation in CYP83E5v2 that inhibits nicotine demethylase in green leaves to produce a plant with conversion levels lower than about 0.2%, 0.3%, 0.4%, 0.5%, 0.6% or 0.7%. Alternatively, a plant having one or more mutations in CYP82E4v2 at position 458, 364, 38, 201, 169, 459, 296, 427, 329, 376 or 171 can be crossed with a plant having one or more mutations in CYP83E5v2 at position 235, 449, 174, 410, 224, 72 or 143 to produce a plant with conversion levels lower than 0.2%, 0.3%, 0.4%, 0.5%, 0.6% or 0.7%. Alternatively still, a plant having one or more mutations in CYP82E4v2 at position 458, 364 or 329 can be crossed with a plant having one or more mutations in CYP83E5v2 at position 235, 449, 174, 410, 224, 72, or 143 to produce a plant with conversion levels lower than 0.2%, 0.3%, 0.4%, 0.5%, 0.6%, or 0.7%. A particularly preferred conversion level of nicotine to nornicotine can be between 0.05%-0.4%, between 0.1-0.6%, between 0.1%-0.3%, between 0.1%-0.5%, between 0.1%-0.4%, between 0.1%-0.7%, or between 0.1%-1.0%. Any mutation of a polynucleotide of the present invention that results in a truncation of the CYP83E4v2 or CYP83E5v2 polypeptide before a conserved heme-binding motif will inhibit the enzyme and can be used in a cross described above. The domains of cytochrome P450 proteins are known in the art. See, e.g., Xu et al. (2007) *Physiologia Plantarum* 129:307-319, incorporated herein by reference as if set forth in its entirety. By crossing plants having a nonfunctional or inhibited CYP82E4v2 gene, a nonfunctional or inhibited CYP82E5v2 gene, or nonfunctional or inhibited CYP82E4v2 and CYP82E5v2 genes, nornicotine levels can be reduced in a tobacco plant.

The activity of a nicotine demethylase polypeptide in converting nicotine to nornicotine in a *Nicotiana* plant or plant part is inhibited according to the present invention if this conversion activity is statistically lower than conversion activity of the same cytochrome P450 polypeptide in a *Nicotiana* plant or plant part that has not been genetically modified to inhibit the conversion activity of that cytochrome P450 polypeptide and that has been cultured and harvested using the same protocols. In particular embodiments, activity of a cytochrome P450 polypeptide in converting nicotine to nornicotine in a modified *Nicotiana* plant or plant part according to the invention is inhibited if the activity is less than 95%, less than 90%, less than 80% less than 70%, less than 60%, less than 50%, less than 40%, less than 30%, less than 20% less than 10%, less than 5%, less than 2% or less than 1% of the conversion activity of the same cytochrome P450 polypeptide in a *Nicotiana* plant that has not been genetically modified to inhibit the expression of that nicotine demethylase polypeptide and that has been cultured and harvested using the same protocols. The activity of a nicotine demethylase polypeptide in converting nicotine to nornicotine in a *Nicotiana* plant or plant part is eliminated according to the invention when it is not detectable by the assay methods known in the art or described herein. Methods of determining the activity of a cytochrome P450 polypeptide in converting nicotine to nornicotine in a *Nicotiana* using gas chromatography are disclosed in the examples below.

In specific embodiments, a cytochrome P450 inhibitory polynucleotide or nicotine demethylase mutation described herein is introduced into a *Nicotiana* plant or plant part. Subsequently, a *Nicotiana* plant or plant part having the introduced inhibiting polynucleotide of the present invention is selected using methods known to those of skill in the art including, but not limited to, Southern blot analysis, DNA sequencing, PCR analysis or phenotypic analysis. A polynucleotide or polypeptide sequence of the present invention includes full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. A plant or plant part altered or modified by the foregoing is grown under plant-forming conditions for a time sufficient to modulate the concentration and/or activity of polypeptides of the present invention in the plant. Plant forming conditions are well known in the art and discussed briefly elsewhere herein.

A transformed tobacco plant containing a nicotine demethylase inhibitory polynucleotide sequence described herein has a reduced level of conversion of nicotine to nornicotine. In particular embodiments, conversion of nicotine to nornicotine in a transformed tobacco plant or plant part according to the invention is less than 95%, less than 90%, less than 80% less than 70%, less than 60%, less than 50%, less than 40%, less than 30%, less than 20%, less than 10%, less than 5%, less than 2% or less than 1% of the conversion in a tobacco plant that that has not been genetically modified to inhibit the expression of that nicotine demethylase polypeptide and with has been cultured and harvested using the same protocols. In some instances, the transformed tobacco plant is a converter tobacco plant. Alternatively, the transformed tobacco plant is a nonconverter tobacco plant. Alternatively still, the transformed tobacco plant has a conversion rate lower than the rate observed in commercial non-converter tobacco plants.

The level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350;

5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) *Proc. Natl. Acad. Sci. USA* 96:8774-8778; each of which is incorporated herein by reference as if set forth in its entirety.

The methods of the present invention do not depend on the incorporation of the entire nicotine demethylase inhibitory polynucleotide into the genome, only that the *Nicotiana* plant or plant part thereof is altered as a result of the introduction of this inhibitory polynucleotide into a cell. As such, the genome may be altered following the introduction of the nicotine demethylase inhibitory polynucleotide into a cell. For example, the inhibitory polynucleotide, or any part thereof, may incorporate into the genome of the plant. Alterations to the genome include, but are not limited to, additions, deletions and substitutions of nucleotides into the genome. While the methods of the present invention do not depend on additions, deletions and substitutions of any particular number of nucleotides, it is recognized that such additions, deletions and/or substitutions comprise at least one nucleotide.

Further, one can reduce the level and/or activity of a nicotine demethylase sequence by eliciting the effects of the sequence only during certain developmental stages and to switch the effect off in other stages where expression is no longer desirable. Control of nicotine demethylase expression can be obtained via the use of inducible or tissue-preferred promoters. Alternatively, the gene could be inverted or deleted using site-specific recombinases, transposons or recombination systems, which would also turn on or off expression of the cytochrome P450 sequence.

According to the present invention, changes in levels, ratios, activity or distribution of cytochrome P450 polypeptides of the present invention, or changes in *Nicotiana* plant or plant part phenotype, particularly reduced accumulation of nornicotine and its carcinogenic metabolite, NNN, can be measured by comparing a subject plant or plant part to a control plant or plant part, where the subject plant or plant part and the control plant or plant part have been cultured and/or harvested using the same protocols. As used herein, a subject plant or plant part is one in which genetic alteration, such as transformation, has been affected as to the nicotine demethylase polypeptide of interest, or is a *Nicotiana* plant or plant part that is descended from a *Nicotiana* plant or plant part so altered and which comprises the alteration. A control plant or plant part provides a reference point for measuring changes in phenotype of the subject plant or plant part. The measurement of changes in phenotype can be measured at any time in a plant or plant part, including during plant development, senescence, or after curing. In other embodiments, the measurement of changes in phenotype can be measured in plants grown under any conditions, including from plants grown in growth chamber, greenhouse, or in a field. In one embodiment, changes in phenotype can be measured by determining the nicotine to nornicotine conversion rate. In a preferred embodiment, conversion can be measured by dividing the percentage of nornicotine (as a percentage of the total tissue weight) by the sum of the percentage nicotine and nornicotine (as percentages of the total tissue weight) and multiplying by 100.

According to the present invention, a control plant or plant part may comprise a wild-type *Nicotiana* plant or plant part, i.e., of the same genotype as the starting material for the genetic alteration that resulted in the subject plant or plant part. A control plant or plant part may also comprise a *Nicotiana* plant or plant part of the same genotype as the starting material but that has been transformed with a null construct (i.e., with a construct that has no known effect on the trait of interest, such as a construct comprising a selectable marker gene). Alternatively, a control plant or plan part may comprise a *Nicotiana* plant or plant part that is a non-transformed segregant among progeny of a subject plant or plant part, or a *Nicotiana* plant or plant part genetically identical to the subject plant or plant part but that is not exposed to conditions or stimuli that would induce suppression of the nicotine demethylase gene of interest. Finally, a control plant or plant part may comprise the subject plant or plant part itself under conditions in which the nicotine demethylase inhibitory sequence is not expressed. In all such cases, the subject plant or plant part and the control plant or plant part are cultured and harvested using the same protocols.

As described elsewhere herein, methods are provided to reduce or eliminate the activity and/or concentration of a nicotine demethylase polypeptide of the present invention by introducing into a *Nicotiana* plant or plant part a nicotine demethylase inhibitory polynucleotide sequence than is capable of inhibiting expression or function of a nicotine demethylase polypeptide that is involved in the metabolic conversion of nicotine to nornicotine. In some instances, the inhibitory sequence can be introduced by transformation of the plant or plant part such as a plant cell with an expression cassette that expresses a polynucleotide that inhibits the expression of the nicotine demethylase polypeptide. The polynucleotide may inhibit the expression of a nicotine demethylase polypeptide directly, by preventing translation of the nicotine demethylase polypeptide messenger RNA, or indirectly, by encoding a polypeptide that inhibits the transcription or translation of a nicotine demethylase polypeptide gene encoding a nicotine demethylase polypeptide. Methods for inhibiting or eliminating the expression of a gene product in a plant are well known in the art, and any such method may be used in the present invention to inhibit the expression of nicotine demethylase polypeptides.

In other embodiments, the activity of a nicotine demethylase polypeptide of the present invention may be reduced or eliminated by disrupting the gene encoding the nicotine demethylase polypeptide. The invention encompasses mutagenized plants that carry mutations in cytochrome P450 genes, where the mutations reduce expression of the nicotine demethylase gene or inhibit the activity of an encoded nicotine demethylase polypeptide of the present invention.

To obtain the desired plants, a *Nicotiana* plant or plant part can be transformed with an expression cassette that is capable of expressing a polynucleotide that inhibits the expression of a nicotine demethylase sequence. Such methods may include the use of sense suppression/cosuppression, antisense suppression, double-stranded RNA (dsRNA) interference, hairpin RNA interference and intron-containing hairpin RNA interference, amplicon-mediated interference, ribozymes, and small interfering RNA or micro RNA.

For cosuppression, an expression cassette is designed to express an RNA molecule corresponding to all or part of a messenger RNA encoding a cytochrome P450 polypeptide of interest (for example, a cytochrome P450 polypeptide comprising the sequence set forth in SEQ ID NO:2 or 5-24 or a sequence having substantial sequence identity to SEQ ID NO:2 or 5-24) in the "sense" orientation. Over-expression of the RNA molecule can result in reduced expression of the native gene. Multiple plant lines transformed with the cosuppression expression cassette are then screened to identify those that show the greatest inhibition of nicotine demethylase polypeptide expression.

The polynucleotide used for cosuppression may correspond to all or part of the sequence encoding a cytochrome P450 polypeptide or the present invention, all or part of the 5' and/or 3' untranslated region of a cytochrome P450 polypeptide transcript, or all or part of both the coding sequence and the untranslated regions of a transcript encoding a cytochrome P450 polypeptide. In some embodiments where the polynucleotide comprises all or part of the coding region for a cytochrome P450 polypeptide of the present invention, the expression cassette can be designed to eliminate the start codon of the polynucleotide so that no polypeptide product will be transcribed.

Cosuppression may be used to inhibit the expression of plant genes to produce plants having undetectable levels for the polypeptides encoded by these genes or may also be used to inhibit the expression of multiple proteins in the same plant (e.g., Broin et al. (2002) *Plant Cell* 14:1417-1432; and U.S. Pat. No. 5,942,657). Methods for using cosuppression to inhibit the expression of endogenous genes in plants are described in Flavell et al. (1994) *Proc Natl. Acad. Sci. USA* 91:3490-3496; Jorgensen et al. (1996) *Plant Mol. Biol.* 31:957-973; Johansen and Carrington (2001) *Plant Physiol.* 126:930-938; Brain et al. (2002) *Plant Cell* 14:1417-1432; Stoutjesdijk et al. (2002) *Plant Physiol.* 129:1723-1731; Yu et al. (2003) *Phytochemistry* 63:753-763; and U.S. Pat. Nos. 5,034,323; 5,283,184 and 5,942,657; each of which is incorporated herein by reference as if set forth in its entirety. The efficiency of cosuppression may be increased by including a poly-dT region in the expression cassette at a position 3' to the sense sequence and 5' of the polyadenylation signal. See, US Patent Application Publication No. 2002/0048814, incorporated herein by reference as if set forth in its entirety. Typically, such a nucleotide sequence has substantial sequence identity to the sequence of the transcript of the endogenous gene, preferably greater than about 65% sequence identity, more preferably greater than about 95% sequence identity, most preferably greater than about 99% sequence identity (e.g., U.S. Pat. Nos. 5,283,184 and 5,034,323; incorporated herein by reference as if set forth in its entirety).

Inhibition of the expression of the cytochrome P450 polypeptide of the present invention also can be obtained by antisense suppression. For antisense suppression, the expression cassette is designed to express an RNA molecule complementary to all or part of a messenger RNA encoding the cytochrome P450 polypeptide. Over-expression of the antisense RNA molecule can result in reduced expression of the native gene. Accordingly, multiple plant lines transformed with the antisense suppression expression cassette are screened to identify those that show the greatest inhibition of nicotine demethylase polypeptide expression.

The polynucleotide for use in antisense suppression may correspond to all or part of the complement of the sequence encoding the cytochrome P450 polypeptide, all or part of the complement of the 5' and/or 3' untranslated region of the cytochrome P450 polypeptide transcript, or all or part of the complement of both the coding sequence and the untranslated regions of a transcript encoding the cytochrome P450 polypeptide. In addition, the antisense polynucleotide may be fully complementary (i.e., 100% identical to the complement of the target sequence) or partially complementary (i.e., less than 100% identical to the complement of the target sequence) to the target sequence.

Antisense suppression also can be used to inhibit the expression of multiple proteins in the same plant (e.g., U.S. Pat. No. 5,942,657). Furthermore, portions of the antisense nucleotides may be used to disrupt the expression of the target gene. Generally, sequences of at least 50 nucleic acids, 100, 200, 300, 400, 450, 500, 550 nucleic acids, or greater may be used. Methods for using antisense suppression to inhibit the expression of endogenous genes in plants are described, e.g., in Liu et al. (2002) *Plant Physiol.* 129:1732-1743; and U.S. Pat. Nos. 5,759,829 and 5,942,657; each of which is incorporated herein by reference as if set forth in its entirety. Efficiency of antisense suppression may be increased by including a poly-dT region in the expression cassette at a position 3' to the antisense sequence and 5' of the polyadenylation signal. See, US Patent Application Publication No. 2002/0048814, incorporated herein by reference as if set forth in its entirety.

For dsRNA interference, a sense RNA molecule like that described above for cosuppression and an antisense RNA molecule that is fully or partially complementary to the sense RNA molecule are expressed in the, same cell, resulting in inhibition of the expression of the corresponding endogenous messenger RNA. Expression of the sense and antisense molecules can be accomplished by designing the expression cassette to comprise both a sense sequence and an antisense sequence for the target cytochrome P450 sequence. Alternatively, separate expression cassettes may be used for the sense and antisense sequences. Multiple plant lines transformed with the dsRNA interference expression cassette or expression cassettes are then screened to identify plant lines that show the greatest inhibition of expression of the targeted cytochrome P450 polypeptide. Methods for using dsRNA interference to inhibit the expression of endogenous plant genes are described in Waterhouse et al. (1998) *Pros. Natl. Acad. Sci. USA* 95:13939-13964; Liu et al. (2002) *Plant Physiol.* 129:1732'-1743; and International Patent Application Publication Nos. WO 99/149024, WO 99/153050, WO 99/161631 and WO 00/149035; each of which is incorporated herein by reference as if set forth in its entirety.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for a cytochrome P450 polypeptide that is involved in the metabolic conversion of nicotine to nornicotine). Methods of using amplicons to inhibit the expression of endogenous plant genes are described, e.g., in Angell & Baulcombe (1997) *EMBO J.* 16:3675-3684; Angell & Baulcombe (1999) *Plant J.* 20:357-362; and U.S. Pat. No. 6,646,805, each of which is incorporated herein by reference as if set forth in its entirety.

In some instances, the polynucleotide expressed by the expression cassette of the invention is catalytic RNA or has ribozyme activity specific for the messenger RNA of a cytochrome P450 polypeptide described herein. Thus, the polynucleotide causes the degradation of the endogenous messenger RNA, resulting in reduced expression of the cytochrome P450 polypeptide. This method is described, for example, in U.S. Pat. No. 4,987,071, incorporated herein by reference as if set forth in its entirety.

In other instances, inhibition of the expression of one or more nicotine demethylase polypeptides may be obtained by RNA interference by expression of a gene encoding a micro RNA (miRNA). miRNAs are regulatory agents consisting of about twenty-two ribonucleotides. miRNA are highly efficient at inhibiting the expression of endogenous genes. See, e.g., Javier et al. (2003) *Nature* 425:257-263, incorporated herein by reference as if set forth in its entirety.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of nicotine demethylase polypeptide expression, the 22-nucleotide sequence is selected from a cytochrome P450 polypeptide transcript sequence and contains 22 nucleotides encoding this cytochrome P450 polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

Alternatively still, inhibition of the expression of one or more cytochrome P450 polypeptides may be obtained by hairpin RNA (hpRNA) interference or intron-containing hairpin RNA (ihpRNA) interference. These methods are highly efficient at inhibiting the expression of endogenous genes. See, Waterhouse & Helliwell (20013) *Nat. Rev. Genet.* 4:29-38 and the references cited therein.

The expression cassette for hpRNA interference may also be designed such that the sense sequence and the antisense sequence do not correspond to an endogenous RNA in this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, e.g., International Patent Application Publication No. WO 02/00904, incorporated herein by reference as if set forth in its entirety.

Transcriptional gene silencing (TGS) may be accomplished through use of hpRNA constructs where the inverted repeat of the hairpin shares sequence identity with the promoter region of a gene to be silenced. Processing of the hpRNA into short RNAs that can interact with the homologous promoter region may trigger degradation or methylation to result in silencing (Aufsatz et al. (2002) *Proc. Natl. Acad. Sci.* 99:16499-16506; and Mette et al. (2000) *EMBO J.* 19:5194-5201).

In some instances, the polynucleotide encodes an antibody that binds to at least one cytochrome P450 polypeptide, and reduces the activity of a cytochrome P450 polypeptide of the present invention. In another embodiment, the binding of the antibody results in increased turnover of the antibody-cytochrome P450 polypeptide complex by cellular quality control mechanisms. The expression of antibodies in plant parts and the inhibition of molecular pathways by expression and binding of antibodies to proteins in plant parts are well known in the art. See, e.g., Conrad & Sonnewald (2003) *Nature Biotech.* 21:35-36, incorporated herein by reference as if set forth in its entirety.

The activity of a cytochrome P450 polypeptide of the present invention can be reduced or eliminated by disrupting the gene encoding the cytochrome P450 polypeptide. The gene encoding the cytochrome P450 polypeptide may be disrupted by any method known in the art, e.g., by transposon tagging or by mutagenizing plants using random or targeted mutagenesis and selecting for plants that have reduced nicotine demethylase activity or mutations in CYP82E4v2 or CYP82E5v2.

Transposon tagging may be used to reduce or eliminate the activity of one or more cytochrome P450 polypeptides of the present invention. Transposon tagging comprises inserting a transposon within an endogenous cytochrome P450 gene to reduce or eliminate expression of the cytochrome P450 polypeptide.

Methods for the transposon tagging of specific genes in plants are well known in the art. See, e.g., Maes et al. (1999) *Trends Plant Sci.* 4:90-96; Dharmapuri & Sonti (1999) *FEMS Micerobiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; and Fitzmaurice et al. (1999) *Genetics* 153:1919-1928).

Additional methods for decreasing or eliminating the expression of endogenous genes in plants are also known in the art and can be similarly applied to the instant invention. These methods include other forms of mutagenesis, using mutagenic or carcinogenic compounds including ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima et al. (1998) *Virology* 213:472-481; Okubara et al. (1994) *Genetics* 137:867-874; and Quesada et al. (2000) *Genetics* 154:421-4315; each of which is incorporated herein by reference as if set forth in its entirety. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum et al. (2000) *Nat. Biotechnol.* 18:455-457, herein incorporated by reference.

Mutations that impact gene expression or that interfere with the function of the encoded cytochrome P450 protein can be determined using methods that are well known in the art. Insertional mutations in gene exons usually result in null-mutants. Mutations in conserved residues can be particularly effective in inhibiting the metabolic function of the encoded protein. Conserved residues of plant cytochrome P450 polypeptides suitable for mutagenesis with the goal to eliminate activity of a cytochrome P450 polypeptide in converting nicotine to nornicotine in a *Nicotiana* plant or plant part have been described. Conserved residues of plant cytochrome P450 polypeptides are disclosed in FIG. 1A-C, where the residues that differ from the other P450 polypeptides are shaded in grey. The conserved residue is that which is not shaded in grey at each position. Such mutants can be isolated according to well-known procedures.

Dominant mutants can be used to trigger RNA silencing due to gene inversion and recombination of a duplicated gene locus. See, e.g., Kusaba et al. (2003) *Plant Cell* 15:1455-1467.

While a number of sequences are recognized in the practice of the invention, in particular sequences encoding SEQ ID NO:2 and 13 find particular use. While not intending to be bound by any particular mechanism of action, the inventors believed that these sequences encode a nicotine demethylase that catalyzes the oxidative N-demethylation of nicotine to nornicotine. Thus, methods to specifically inhibit these coding sequences and not other P450 sequences may be beneficial to the recombinant plant. That is, strategies that would lead to inhibition of gene function of this individual locus may prove to be superior to those that inhibit the entire gene family. The P450 enzymes are involved in many mechanisms in the plant, the inhibition of which may prove deleterious or detrimental to the growth and development of the plant or may negatively impact factors such as the disease defense capabilities of the plant. Likewise, because the *Nicotiana* plant P450 enzymes have been implicated in plant metabolites such as phenylpropanoid, alkaloids, terpenoids, lipids, cyanogenic glycosides, glucosinolates, and a host of other chemical entities, disruption of P450 activity may alter components involved in tobacco flavor, texture, or other properties that would impact the commercial usefulness of the plant. Therefore, the use of the methods discussed above to inhibit expression in a manner that specifically targets the sequence coding for SEQ ID NO:2 or 13 may be preferred, including targeted mutational strategies, such as chimeraplasty. See, e.g., Stewart et al. (2000) *Biotechniques* 24:838-843; and Graham et al. (2002) *Biochim Biophys Acta* 1587:1-6; each of which is incorporated herein by reference as if set forth in its entirety. In some embodiments, the methods discussed above are used to inhibit expression in a manner that specifically targets SEQ ID NO:1 (encoding SEQ ID NO:2), SEQ ID NO:50 (encoding SEQ ID NO:13), or both of these sequences.

The compositions of the invention can be used in screening methods to identify nonconverter plants for use in breeding programs. In this manner, the nucleotide sequences of the invention can be used to screen native germplasms for nonconverter plants having a stable mutation in one or more P450 genes identified herein. These nonconverter plants identified by the methods of the invention can be used to develop breeding lines.

In addition to the nucleotide sequences encoding P450 coding sequences, compositions of the invention include an intron sequence in the CYP82E5v2 sequence that can be used in screening methods. While not intending to be bound by any particular mechanism of action, the CYP82E5v2 gene(s) may represent the only member(s) of the cytochrome P450 family involved in the metabolic conversion of nicotine to nornicotine (and as stated previously there is a good likelihood that the CYP82E5v2 cDNAs originated from a single unique genetic locus) in green-leaves of tobacco. For certain applications, it would be useful to have a means of diagnostically differentiating this specific member of the cytochrome P450 gene family from the rest of the closely related sequences within this family. For example, it is possible that within the naturally existing tobacco germplasm (or in mutagenized populations), accessions may exist in which this gene is naturally dysfunctional and may therefore may be valuable as a permanently nonconverter resource. Such dysfunctional genes may include those encoding the polypeptides set forth in SEQ ID NOS:6 and 12. A method to specifically assay for such genotypes (e.g., deletion mutants, rearrangements, and the like) could serve as a powerful tool. The present invention includes primers designed to specifically amplify exon 1 and exon 2 of CYP82E5v2 or CYP82E4v2 where one of the two primer pairs corresponds to the intron between the exons. Examples of primers useful to amplify the exons of CYP82E4v2 include SEQ ID NO:32 with SEQ ID NOS:33-35. Examples of primers useful to amplify the exons of CYP82E5v2 include SEQ ID NO:36 with 37 and SEQ ID NO:38 with 39. These same primers can be used for sequence analysis of the products.

When any cDNA corresponding to a member of the CYP82E2 family is used as a hybridization probe in a Southern blotting assay of tobacco genome is DNA, a complex pattern is observed. This is expected, given that there are multiple, closely related members of this gene family. Because the intron regions of genes are typically less conserved than exons, it is predicted that the use of an intron-specific probe would reduce this complexity and better enable one to distinguish the gene(s) corresponding to the CYP82E4v2 gene or the CYP82E5v2 gene from the other members of the family. The use of a CYP82E4v2 or CYP82E5v2 intron-specific probe, and/or the PCR primers used to generate products provide powerful tools in assays to determine whether any naturally occurring, or mutagenized, tobacco plants possess deletions or rearrangements that may render the gene inactive. Such a plant can then be used in breeding programs to create tobacco lines that are incapable of converting.

Transformed Plants, Plant Parts and Products Having Reduced Nornicotine and NNN Content The cytochrome P450 polynucleotides of the invention, and variants and fragments thereof, can be used in the methods of the present invention to inhibit cvtochrome P450s that are involved in the metabolic conversion of nicotine to nornicotine in a plant. In this manner, inhibitory sequences that target expression or function of a cytochrome P450 polypeptide disclosed herein are introduced into a plant or plant cell of interest. The expression cassettes described herein can be introduced into a plant of interest, for example, a *Nicotiana* plant as noted herein below, using any suitable transformation methods known in the art including those described herein.

The methods of the invention do not depend on a particular method for introducing a sequence into a plant or plant part, only that the desired sequence gains access to the interior of at least one cell of the plant or plant part. Methods for introducing polynucleotide sequences into plants are known in the art and include, but are not limited to, stable transformation methods, transient transformation methods and viral-mediated transformation methods.

Transformation protocols as well as protocols for introducing heterologous polynucleotide sequences into plants vary depending on the type of plant or plant cell targeted for transformation. Suitable methods of introducing polynucleotides into plant cells of the present invention include microinjection (Crossway et al. (1986) *Biotechniques* 4:320-334), electroporation (Shillito et al. (1987) *Meth. Enzymol.* 153:313-336; and Riggs et al. (1986) *Proc. Natl. Acad Sci. USA* 83:5602-56116), *Agrobacterium*-mediated transformation (U.S. Pat. Nos. 5,104,310; 5,149,645; 5,177,010; 5,231,019; 5,463,174; 5,464,763; 5,469,976; 4,762,785; 5,004,863; 5,159,135; 5,563,055 and 5,981,840), direct gene transfer (Paszkowski et al. (1984) *EMBO J.* 1:2717-2722) and ballistic particle acceleration (U.S. Pat. Nos. 4,945,050; 5,141,131; 5,886,244; 5,879,918 and 5,932,782; Tomes et al. (1995) in *Plant cell, tissue, and organ culture fundamental methods*, ed. Gamborg & Phillips (Springer-Verlag, Berlin); McCabe et al. (1988) *Biotechnology* 6:923-926). See also, Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer & McMullen (1991) *In Vitro Cell Dev. Biol.* 27P:175-182 (soybean); Singh et al. (1998) *Theor. Appl. Genet.* 96:319-324 (soybean); De Wet et al. (1985) in *The experimental manipulation of ovule tissues*, ed. Chapman et al. (Longman, New York.); pp. 197-209 (pollen); Kaeppler et al. (1990) *Plant Cell Reports* 9:415-418; and Kaeppler et al. (1992) *Theor. Appl. Genet*, 84:560-566 (whisker-mediated transformation); D'Halluin et al. (1992) *Plant Cell* 4:1495-1505 (electroporation); each of which is incorporated herein by reference as if set forth in its entirety.

Any plant tissue that can be subsequently propagated using clonal methods whether by organogenesis or embryogenesis, may be transformed with a recombinant construct comprising a cytochrome P450 inhibitory sequence, for example, an expression cassette of the present invention. As used herein, "organogenesis" means a process by which shoots and roots are developed sequentially from meristematic centers. As used herein, "embryogenesis" means a process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds and root inersistems) and induced meristem tissue (e.g., cotyledon meristem and hypocotyl meristem), hypocotyls, cotyledons, leaf disks, pollen, embryos and the like.

As used herein, "stable transformation" means that the nucleotide construct of interest introduced into a plant integrates into the genome of the plant and is capable of being inherited by the progeny thereof. Likewise, "transient transformation" means that a sequence is introduced into the plant and is only temporally expressed or is only transiently present in the plant.

The inhibitory sequences of the invention can be provided to a plant using a variety of transient transformation methods. The inhibitory sequences of the invention can be transiently transformed into the plant using techniques known in the art. Such techniques include viral vector systems and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyenlimine (PEI; Sigma 4P3143).

Alternatively, the inhibitory sequence of the invention may be introduced into plants by contacting plants with a virus or viral nucleic acids. Generally, such methods involve incorporating an expression cassette of the invention within a viral DNA or RNA molecule. Promoters for use in the expression cassettes of the invention also encompass promoters utilized for transcription by viral RNA polymerases. Methods for introducing polynucleotides into plants and expressing a protein encoded therein, involving viral DNA or RNA molecules, are known in the art. See, e.g., U.S. Pat. Nos. 5,889,191; 5,889,190; 5,866,785; 5,589,367; 5,316,931; and Porta et al. (1996) *Molecular Biotechnology* 5:209-221; each of which is incorporated herein by reference as if set forth in its entirety.

Transformed cells may be grown into *Nicotiana* plants in accordance with conventional methods. See, e.g., Vasil & Hildebrandt (1965) *Science* 150:889; Negaard & Hoffman (1989) *Biotechniques* 7(8):808-812. These plants may then be grown, and either pollinated with the same transformed line or different lines, and the resulting progeny having expression of the desired phenotypic characteristic identified, i.e., reduced expression of one or more nicotine demethylases that are involved in the metabolic conversion of nicotine to nornicotine, and thus reduced content of nornicotine, and a concomitant reduced content of its nitrosamine metabolite, NNN, in the plant, particularly in the leaf tissues. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

The compositions and methods of the invention can be used to reduce the nornicotine content, particularly in the leaves and stems, of any plant of the genus *Nicotiana* including, but not limited to, the following species: *acuminata, affinis, alata, attenuate, bigelovii, clevelandii, excelsior, forgetiana, glauca, glutinosa, langsdorffii, longiflora, obtusifolia, palmeri, paniculata, plumbaginifolia, qudrivalvis, repanda, rustica, suaveolens, sylvestris, tabacum, tomentosa, trigonophylla* and x *sanderae*. The present invention also encompasses the transformation of any varieties of a plant of the genus *Nicotiana*, including, but not limited to, *Nicotiana acuminata multiflora, Nicotiana alata grandiflora, Nicotiana bigelovii quadrivalvis, Nicotiana bigelovii wallacei, Nicotiana obtusifolia obtusifolia, Nicotiana obtusifolia plameri, Nicotiana quadrivalvis bigelovii, Nicotiana quadrivalvis quadrivalvis, Nicotiana quadrivalvis wallacei,* and *Nicotiana trigonophylla palmeri*, as well as varieties commonly known as flue or bright varieties, Burley varieties, dark varieties and oriental/Turkish varieties.

The transgenic plants of the genus *Nicotiana* as described herein are suitable for conventional growing and harvesting techniques, such as cultivation in manure rich soil or without manure, bagging the flowers or no bagging, or topping or no topping. The harvested leaves and stems may be used in any traditional tobacco product including, but not limited to, pipe, cigar and cigarette tobacco, and chewing tobacco in any form including leaf tobacco, shredded tobacco, or cut tobacco.

Thus the present invention provides a *Nicotiana* plant, particularly leaf tissues of these plants, comprising an expression cassette of the invention and a reduced amount of nornicotine and N'-nitrosonornicotine. As used herein, "a reduced amount" or "a reduced level" means an amount of nornicotine and/or NNN in a treated or transgenic plant of the genus *Nicotiana* or a plant part or tobacco product thereof that is less than what would be found in a plant of the genus *Nicotiana* or a plant part or tobacco product from the same variety of tobacco, processed (i.e., cultured and harvested) in the same manner, that has not been treated or was not made transgenic for reduced nornicotine and/or NNN. The amount of nornicotine may be reduced by about 10% to greater than about 90%, including greater than about 20%, about 30%, about 40%, about 50%, about 60%, about 70% and about 80%. The conversion of nicotine to nornicotine can be less than 0.3%, less than 0.5%, less than 0.7%, between 0.1%-0.5%, between 0.1%-0.4%, between 0.1%-0.7%, or between 0.1%-1.0% in plants, plant parts, and products of the present invention, and more specifically in plants, plant parts having mutations in CYP82E4v2 and CYP825v2.

As used herein, "tobacco products" means, but is not limited to, smoking materials (e.g., any cigarette, including a cigarillo, a non-ventilated or vented recess filter cigarette, a cigar, pipe tobacco), smokeless products (e.g., snuff, chewing tobacco, biodegradable inserts (e.g., gum, lozenges, dissolving strips)). See, e.g., US Patent Application Publication No. 2005/0019448, incorporated herein by reference as if set forth in its entirety. Tobacco product also includes blends that can be made by combining conventional tobacco with differing amounts of the low nornicotine and/or NNN tobacco described herein. Tobacco products also includes plant or plant part of the genus *Nicotiana* as described above is cured tobacco.

The tobacco products described herein reduce the carcinogenic potential of tobacco smoke that is inhaled directly with consumption of a tobacco product such as cigars, cigarettes, or pipe tobacco or inhaled as secondary smoke (i.e., by an individual that inhales the tobacco smoke generated by an individual consuming a tobacco product such as cigars, cigarettes, or pipe tobacco). The cured tobacco described herein can be used to prepare a tobacco product, particularly one that undergoes chemical changes due to heat, comprising a reduced amount of nornicotine and/or NNN in the smoke stream that is inhaled directly or inhaled as secondary smoke. In the same manner, the tobacco products of the invention may be useful in the preparation of smokeless tobacco products such as chewing tobacco, snuff and the like.

The tobacco products derived from the transgenic tobacco plants of the present invention thus find use in methods for reducing the carcinogenic potential of these tobacco products, and reducing the exposure of humans to the carcinogenic nitrosamine, NNN, particularly for individuals that are users of these tobacco products. The following examples are offered by way of illustration and not by way of limitation.

EXPERIMENTAL

The following materials and protocols are utilized in the experiments described herein below.
Plant Materials All plant materials were obtained from Dr. Earl Wernsman, Department of Crop Science, North Carolina State University (Raleigh, N.C.). *N. tomentosiformis* and *N. sylvestris* seed were obtained from the *Nicotiana* germplasm collection maintained by North Carolina State University. Plants were grown in growth chambers for two months until they were transferred to a greenhouse. Burley lines DH 98-325-5 (nonconverter) and DH 98-325-6 (converter) represent near-isogenic lines, i.e., recovered from the same maternal haploid plant. SC58 is a flue-cured tobacco variety, nonconverter individuals of which are designated SC58 ($c_T c_T$). SC58($C_T C_T$) is a near-isogenic stable converter line that originated though the introgression of the single dominant converter locus ($C_r$) found in the tobacco progenitor species *N. tomentosiformis* into SC58 (Mann et al. (1964) *Crop Sci.*, 4:349-353). After eight additional backcrosses to SC58, the near-isogenic SC58($C_T C_T$) line was created and was subsequently maintained via self-fertilization.

All plants were maintained in growth chambers or greenhouses using standard potting soil and fertilizer. Plants kept in a 14/10 light/dark cycle, were watered once a day as needed and fertilized with Peters Professional® All Purpose Plant Food fertilizer (20-20-20; Spectrum Brands Inc.; Madison, Wis.) once a week. To facilitate senescence, detached green leaves were treated by dipping each leaf for 30 seconds in a 0.2% ethephon solution. Leaves were cured in plastic bags under dark conditions until they turned yellow.

For the ethyl methane sulphonate (EMS) mutagenesis, two grams of seed from the strong converter Burley tobacco line DH98-325-6 were surface-sterilized in 50% bleach for 12 minutes and rinsed 6 times in sterile dH$_2$O. Approximately 80 mg aliquots were then placed in screw cap vials and imbibed in 1 ml dH$_2$O for 12 hours. The dH$_2$O was decanted, and the seed was incubated in 1 ml of 0.5% EMS (Sigma; St. Louis, Mo.) and rocked gently on a Nutator® Mixer (TCS Scientific Corp.; New Hope, Pa.) at room temperature for 12 hours in the dark. After removal of the EMS solution, the treated seeds were washed eight times in 1 ml volumes of dH2O with gentle shaking for 5 minutes. After the final wash, seeds were collected onto a Buchner funnel for a final rinse and subsequently allowed to dry on filter paper before sowing on soil. Seedlings were grown on standard float trays for about 7 weeks, then transplanted to a field. Field-grown plants were allowed to self-pollinate, and 5-10 capsules (containing $M_1$ generation seed) per plant were collected and catalogued corresponding to approximately 4000 independent $M_0$ individuals.
Isolation of NtabCYP82E5v2 cDNA Total RNA was extracted from green and senescing leaves of DH98-325-6 tobacco using TRIzol® (Invitrogen; Carlsbad, Calif.) following the protocol of the manufacturer. Genomic DNA was removed by treating the extracts with TURBO DNA-free™ DNase Kit (Ambion; Austin, Tex.) following the protocol of the manufacturer. cDNA synthesis was performed with the StrataScript™ First-Strand Kit (Stratagene; Cedar Creek, Tex.) using oligo dT primers and 3 µg of DNase-free total RNA. Full-length NtabCYP82E5v2 cDNAs were amplified using the E5Orf_F forward and E5Orf_R reverse primers, 10 ng tobacco leaf cDNA library as a template and Long Range™ PCR Enzyme Blend (GeneChoice, Inc.; Frederick, Md.) following the protocol of the manufacturer. DNA sequence information of the primers is listed in the sequence listing and above. PCR conditions were as follows: 3 minutes initial denaturation at 95° C. followed by 33 cycles of denaturation at 94° C. for 30 seconds, annealing at 60° C., for 30 seconds and extension at 68° C. for 90 seconds, followed by an incubation at 68° C. for 7 minutes. PCR products were cloned into pGEM®-T Easy cloning vector (Promega Corp.; Madison, Wis.) and sequenced according to the dideoxy method using synthetic oligonucleotides as primers (Sanger et al. (1977) *Proc. Natl. Acad. Sci. U.S.A.* 74: 5463-5467).
Isolation of the Genomic CYP82E5 Fragments Genomic DNA was isolated from the green leaves of *N. tomentosiformis* and DH98-325-6 tobacco using a cetyltrimethyl ammonium bromide-based extraction procedure according to the instructions of the NucleoSpin® Plant kit (BD Bioscience Clontech; Palo Alto, Calif.).

Genomic fragments of the CYP82E5 orthologs were amplified in two consecutive PCR reactions using nested primers. The first PCR mixture contained 0.5 µM each of the E5Gen_F1 forward (SEQ ID NO:40) and E5Gen_R1 reverse (SEQ ID NO:41) primers, 200 µM of each dNTP, 20 ng of genomic DNA template and 2 U of Platinum® Taq polymerase (Invitrogen). PCR amplification was performed under the following conditions: 90° C. for 3 minutes; 30 cycles of denaturation at 94° C. for 30 seconds, annealing at 57° C. for 30 seconds and extension at 68° C. for 2.2 minutes followed by a final extension at 68° C. for 5 minutes. The composition and conditions of the second PCR were the same as those described for the first amplification, except primers E5Gen_F2 (SEQ ID NO:42) and E5Gen_R2 (SEQ ID NO:43) were added and 1 µl of a 50-fold diluted sample of the first PCR product was used as a template. The purified products of the final PCR were ligated into the pGEM-T-Easy cloning vector and subjected to DNA sequencing.
Expression of the NtabCYP82E5v2 cDNA in Yeast To facilitate the expression of the NtabCYP82E5v2 cDNA in yeast, the open reading frame of the gene was inserted downstream of the galactose-inducible, glucose-repressed GAL10-CYC1 promoter of the pYeDP60 yeast expression vector (Cullin & Pompon 1988). The recombinant plasmid was introduced into WAT11 yeast strain using the lithium-acetate-based transformation method as described by Gietz et al. (1992) *Nucleic Acids Res.* 20:1425-1425. Yeast culturing, galactose-mediated induction of gene expression and the isolation of the microsomal fractions were performed according to the protocol of Pompon et al. (1996) *Methods Enzymol.* 272:51-64.

Kinetic Analysis of NtabCYP82E5-Mediated Nicotine Metabolism

The nicotine metabolism assays were performed in a reaction mixture containing 0.75 mM NADPH, 2.5 µM [pyrrolidine-2-$^{14}$C] nicotine (Moravek Biochemicals; Brea, Calif.) and 90 µg of yeast microsomes in a final volume of 150 µl Pi buffer, pH 7.1. Nicotine concentrations were adjusted by the addition of nonradiolabelled nicotine to final concentrations ranging between 0.7 and 13 µM. Microsomal preparations isolated from yeast containing an empty vector were used as negative control. Reaction mixtures were incubated at 25° C. for 7 minutes, and the reaction was arrested with 50 µl of acetone. After centrifugation at 16,000×g for 3 minutes, 50 µl the sample was spotted on a 250-µm Whatman K6F silica plate. The plates were developed in choloroform:methanol:ammonia (60:10:1) solvent system. Nicotine and its nornicotine derivative were quantified by measuring the relative abundance of their radioactive traces with a Bioscan System 400 imaging scanner. $K_m$ and $v_{max}$ values were calculated by fitting the Michaelis-Menten equation to nicotine demethylation measurements at different substrate concentrations using the SigmaPlot® 10.0 graphing software (Systat Software, Inc.; San Jose, Calif.).

Quantitative Real-Time PCR Analysis of CYP82E4v2 and CYP82E5v2 Expression

Expression of the *N. tomentosiformis* and tobacco orthologs of CYP82E4v2 and CYP82E5v2 were analyzed by allele-specific, quantitative real-time PCR (qrt-PCR) analysis using SYBR® Green I fluorescence chemistry (Morrison et al. (1998) *Biotechniques* 24: 954-962). Total RNA was extracted from the green and cured leaves of 3-month-old plants using the methods already described for NtabCYP82E5v2 cDNA isolation herein. CYP82E4v2 and CYP82E5v2 transcripts were amplified using the E4Rt_F (SEQ ID NO:44) and E5Rt_F (SEQ ID NO:46) forward in conjunction with the E4Rt_R (SEQ ID NO:45) and the E5Rt_R reverse (SEQ ID NO:47) primers, respectively. The qrt-PCR mixture contained 1× iQ™ SYBR® Green Supermix (Bio-Rad Laboratories) 0.5 µM of each primer and 0.5 µg of cDNA. Transcript measurements were obtained using standard curves generated by amplifying known amounts of target DNA and a 220-bp fragment of the glyceraldehyde-3-phosphate dehydrogenase (G3PDH) gene, amplified with the G3PDH_F (SEQ ID NO:48) and G3PDH_R (SEQ ID NO:49) primers, to provide an internal standard for cDNA measurements. DNA amplifications were performed using the real time PCR system (Bio-Rad Laboratories; Hercules, Calif.) under the following conditions: 95° C. for 2 minutes; 35 cycles of 95° C. for 30 seconds, 57 C for 30 seconds, 72° C. for 50 seconds followed by final extension at 72° C. for 5 minutes. DNA sequences of the amplicons generated by qrt-PCR were verified by cloning the PCR products and sequencing 20 randomly selected clones.

Transgenic Plant Analysis

The RNAi-based gene silencing constructs are assembled in a version of the pKYL80 cloning vector (Schardl et al. (1987) Gene 61:1-11) that is engineered to contain a 151-bp fragment of the soybean FAD3 gene intron between the XhoI and SacI restriction sites of the polylinker (pKYLX80I). To create a construct in which the FAD3 intron was flanked by a sense and antisense fragment of CYP82E5v2, a 400-bp intron region is cloned between the HindIII-XhoI and SacI-XbaI restriction sites of pKYLX801 in its sense and antisense orientation, respectively. The resulting HindIII-XbaI fragment containing the CYP8E5v2 sense arm, FAD3 intron, and CYP82E5v2 antisense arm is subcloned into the pKYLX71 plant binary expression vector (Maiti et al. (1993) *Proc. Natl. Acad. Sci. USA* 90:6110-6114) between the 35S CaMV promoter and a rubisco small subunit terminator.

Overexpression constructs are created by replacing the 3-glucuronidase ORF of the plant binary expression vector pBI121 (Clontech) with the full-length coding regions of the CYP82E5v2, CYP82E5v2 variants, or CYP82E4v2 variants cDNAs. This places the tobacco P450s under the transcriptional control of the 35S CaMV promoter. The pBI121- and pKYLX71-based constructs are transformed into *Agrobacterium tumefaciens* strain LBA 4404 and introduced into tobacco cultivars Petite Havana and DH98-325-6 (converter), respectively, using established protocols (Horsch et al. (1985) *Science* 227:1229-1231).

Northern Blot Analysis

Total cellular RNAs are isolated from tobacco leaves using the TRIZOL® method as described by the manufacturer (Invitrogen). Five to ten micrograms of RNA are size fractionated on a 1.2% agarose gel prepared in TBE buffer. RNA immobilization, probe labeling, and signal detection are carried out using the DIG nucleic acid labeling and detection kits according to the manufacturer's instructions (Roche). Alternatively, probes are synthesized using $^{32}$P-dCTP according to protocols accompanying the Random Primed DNA Labeling kit (Roche).

Isolation of DNA from EMS-Mutagenized Plants.

Genomic DNA was isolated from young leaf material of a single greenhouse-grown $M_1$ plant from each independent $M_1$ seed pool. 1.5 ml screw cap vials were used to collect a single leaf disc from each plant and the samples were stored at −80° C. until they were processed. The leaf tissue was deposited to the bottom of the vial by centrifugation, and the tubes were set in a shallow amount of liquid nitrogen to facilitate grinding using plastic pestles. Genomic DNA was isolated from the ground material by adding 320 µl extraction buffer (200 mM Tris-Cl, pH 7.5, 250 mM NaCl, 25 mM EDTA, 0.5% SDS). Samples were vortexed for 20 seconds, and left at room temperature for 5 minutes, followed by a 37° C. incubation for 3 minutes. The lysed material was centrifuged 10 minutes, and the supernatant transferred to fresh tube. 50 µl of protein precipitation solution (Qiagen) was added, the samples briefly vortexed, then set on ice for 5 minutes, followed by a 4 minutes centrifugation at 16,000×g. Precipitation of nucleic acids was accomplished by adding 0.7 volume isopropanol to the supernatant followed by centrifugation for 7 minutes at 12,000×g. After a 70% ethanol wash, the pellet was resuspended in 50 µl TE.

Template Preparation for Sequencing.

CYP82E4v2 and CYP82E5v2 each contain two exons separated by a large intron (1001 bp and 1054 bp, respectively). PCR primers are designed to specifically amplify exon 1 and exon 2 for each gene. Due to the high sequence homology shared among the cDNAs of CYP82E2 gene family members, two primer pairs correspond to intron sequence in order to obtain amplification products specific to the desired gene (owing to the fact that the intron sequences of this gene family are not nearly as conserved as the exon sequences). The exon 1-specific primers for CYP82E4v2 are 5'-TGGAATTATGCCCATCCTACA-3' (forward) (SEQ ID NO:32) and 5'-CATTAGTGGTTGCACCTGAGG-3' (reverse) (SEQ ID NO:33). CYP82E4v2 exon 2-specific primers are 5'-GATGAGATGTGTGCATACTTG-3' (forward) (SEQ ID NO: 34) and 5'-CCAAATT-AGAAAAACTCGTACTG-3' (reverse) (SEQ ID NO:35). For CYP82E5v2, the primers specific for amplifying exon 1 are 5'-ATTGTAGGACTAGTAACCCTTACAC-3' (forward)

(SEQ ID NO:36) and 5'-GAGGCACAAAGAATTCT-CATC-3' (reverse) (SEQ ID NO:37); and for CYP82E5v2 exon 2, the primers 5'-GAGTAGAGGGATTGTTTCCG-3' (forward) (SEQ ID NO:38) and 5'-GTACAATCAAGA-TAAAACATCTAAGG-3' (reverse) (SEQ ID NO:39) are used. PCR reactions were conducted in 96-well microtiter plates using 1 μl of template in a 25 μl reaction volume containing 10 μmoles each primer, 200 μM dNTP, 1.5 mM MgCl and 1.4 units of high fidelity Taq DNA polymerase (Roche). DNA amplification of CYP82E4v2 sequences was performed using an initial 3 minutes denaturation at 94° C., followed by 30 cycles of denaturation at 94° C. for 30 seconds, primer annealing at 55° C. for 30 seconds, and extension at 72° C. for 1.5 minutes, followed by a final 7 minutes 72° C. extension. Amplification conditions for CYP82E5v2 gene fragments were the same except the annealing temperature was 53° C. PCR reaction products were purified using Millipore's Montage PCμ96 filter units. Agarose gel electrophoresis was used to estimate the quantity and quality of the cleaned up PCR products prior to sequencing.

Sequence Analysis.

The PCR products were subjected to cycle sequencing using Applied Biosystems Big Dye Version 3.1 in 96-well format sequencing reactions according to the manufacturer's instructions. The primers used for sequencing (3.2 μmoles per reaction) are as follows: 5'-TGGAATTATGCCCATCC-TACA-3' (SEQ ID NO:32) and 5'-CC-TATAAAAAGGAAGTTGCCG-3' (SEQ ID NO:44) (forward and reverse primers for exon 1 of CYP82E4v2); 5'-GATGAGATGTGTGCATACTTG-3' (SEQ ID NO:34) and 5'-CCAAATTAGAAAAACTCGTACTG-3' (SEQ ID NO:35) (forward and reverse primers for exon 2 of CYP82E4v2); 5'-ATTGTAGGACTAGTAACCCTTACAC-3' (SEQ ID NO:36) and 5'-CTCATCTTTTTTCCATTTAT-CATTC-3' (SEQ ID NO:45) (forward and reverse primers for exon 1 of CYP82E5v2); and 5'-CAAGGTTCGGCAGA-TAGTG-3' (SEQ ID NO:46) and 5'-GTACAATCAAGA-TAAAACATCTAAGG-3' (SEQ ID NO:39) (forward and reverse primers for exon 2 of CYP82E5v2). Sequencing reactions were cleaned up using EdgeBioSystems 96-well plates and analyzed using high-throughput Applied Biosystems 3700 or 3730 capillary sequencers. Sequences were aligned using the Clustal W algorithm as represented in the Vector NTI software package (Invitrogen). Putative mutations are verified by repeating the sequence analysis on sibling $M_1$ plants grown from the cognate $M_0$ seed lot.

Alkaloid Analysis

Alkaloid analyses are performed by gas chromatography as described previously. Briefly, alkaloid analyses are performed by detaching tobacco leaves and dipping them in a solution of 1% ethephon, then, air-curing in a growth chamber for 7-10 days. Cured leaves are dried at 50° C. for two days and ground to a fine powder. A quantitative determination of the nicotine, nornicotine, anatabine and anabasine content was made using a Perkin Elmer Autosystem XL Gas Chromatograph according to the "LC-Protocol" established at the University of Kentucky (available online at the University of Kentucky's website), hereby incorporated by reference.

Example 1: Isolation and Characterization of CYP82E5V2

Nicotine Conversion in *N. tomentosiformis* and Various Tobacco Genotypes

To assess the alkaloid composition of wild-type plants, concentrations of nicotine and nornicotine were determined in the green and cured leaves of *N. tomentosiformis* and various tobacco genotypes using gas chromatography. In *N. tomentosiformis*, nornicotine appears as the predominant alkaloid in both the green and cured leaves (Table 1). Converter Burley cultivar DH-98-325-6 and converter Flue-Cured cultivar SC58C contain low levels of nornicotine (about 3%) in the green leaves, but a large percentage (about 95 and 25%, respectively) nicotine content is metabolized into nornicotine once the leaves senesce (see, Table 1). Levels of nornicotine are low in both the green and cured leaves of nonconverter Burley and Flue-Cured cultivars DH98-325-5 and SC58NC, respectively, although nicotine conversion slightly increases after curing.

TABLE 1

Alkaloid analysis of green and cured leaves of *N. tomentosiformis* and various tobacco genotypes.

| Plant | Phenotype | % Nicotine[a] | | % Nornicotine[a] | | % Conversion[b] | |
| --- | --- | --- | --- | --- | --- | --- | --- |
| | | Green | Cured[c] | Green | Cured[c] | Green | Cured |
| *N. tomentosiformis* | GLC | 0.003[d] | 0.007 | 0.188 | 0.299 | 98.4 | 97.7 |
| | | (0.0002) | (0.001) | (0.022) | (0.031) | (2.4) | (2.1) |
| DH98-325-5 | NC | 1.243 | 1.332 | 0.032 | 0.040 | 2.6 | 3.0 |
| | | (0.334) | (0.321) | (0.006) | (0.008) | (0.2) | (0.3) |
| DH98-325-6 | SLC | 1.113 | 0.082 | 0.041 | 1.416 | 3.5 | 94.4 |
| | | (0.095) | (0.019) | (0.004) | (0.187) | (0.1) | (1.6) |
| SC58NC | NC | 1.422 | 1.487 | 0.032 | 0.039 | 2.2 | 2.5 |
| | | (0.127) | (0.089) | (0.004) | (0.001) | (0.07) | (0.1) |
| SC58C | SLC | 1.171 | 0.501 | 0.029 | 0.164 | 2.4 | 24.7 |

[a]Percentage of leaf dry weight.
[b][% nornicotine (% nicotine + % nornicotine)$^{-1}$] × 100.
[c]Leaves are treated with 0.2% ethephon and cured until they turned yellow.
[d]Mean over the alkaloid content of three plants, except SC58C where one plant was used due to the low frequency of conversion.
[e]Values in parenthesis represent standard error of the mean.
Abbreviations: GLC, green-leaf converter; NC, nonconverter; SLC, senescing-leaf converter.

Isolation of the NtabCYP82E5v2 cDNA from Tobacco

To identify putative nicotine demethylase genes from tobacco, a PCR-based gene amplification strategy was used where the primers are complementary to the 5' and 3' termini of the NtabCYP82E3 coding region. Primer design was based on the observation that all members of the closely-related CYP82E2 gene subfamily display a high degree of DNA sequence identity at the regions immediately following the ATG initiation signal and preceding the TAA stop codon (Siminszky et al. (2005) *Proc. Natl. Acad. Sci. U.S.A.* 102: 14919-14924) providing well conserved primer target sites for the amplification of additional family members. A PCR using CYP82E3-specific primers and permissive annealing temperatures was conducted to amplify putative nicotine demethylase genes from a tobacco green leaf cDNA library. DNA sequence analysis of 20 randomly selected clones generated from the PCR products yielded 19 NtabCYP82E3 cDNA sequences and one cDNA whose DNA sequence is different from all functionally characterized members of the CYP82E2 gene subfamily (Siminszky et al. (2005) *Proc. Natl. Acad. Sci. U.S.A.* 102: 14919-14924). A homology search against the GenBank database using the BLAST algorithm reveals that the clone representing the unique DNA sequence shares a 99.7% nucleotide and a 99.2% predicted amino acid identity with the tobacco CYP82E5v1 cDNA of unknown function. According to the guidelines of the P450 nomenclature committee, the cDNA was named NtabCYP82E5v2. The predicted amino acid sequence of NtabCYP82E5v2 is 89.2, 91.9 and 91.3% identical to that of NtabCYP82E2, NtabCYP82E3 and NtabCYP82E4v2, respectively.

NtabCYP82E5v2 Encodes for a Functional Nicotine Demethylase

To determine whether NtabCYP82E5v2 encodes nicotine demethylase activity, the N.tabCYP82E5 cDNA is expressed in the WAT11 yeast strain. The WAT11 strain was engineered to provide high efficiency transgene expression and an optimal redox environment for P450-mediated reactions by expressing the *Arabidopsis* P450 reductase gene, ATR1, under the transcriptional control of a galactose-inducible promoter (Pompon et al. (1996) *Methods Enzymol.* 272: 51-64). Microsomal fragments isolated from yeast expressing NtabCYP82E5v2 actively catalyze the N-demethylation of nicotine. The $K_m$ and $v_{max}$ values for the NtabCYP82E5v2-mediated nicotine demethylase reaction are 5.6±1.4 µM and 0.7±0.02 nmol min$^{-1}$ mg$^{-1}$ protein (mean±standard error), respectively. In contrast, no nicotine demethylase activity is evident when microsomes isolated from yeast transformed with an empty plasmid are added to the catalytic assay.

NtabCYP82E5v2 is Derived from Progenitor *N. tomentosiformis*

As the allotetraploid genome of tobacco consists of two genetic components, the S genome donated by *N. sylvestris* and the T genome derived from *N. tomentosiformis*, which of the two progenitor species contributed NtabCYP82E5v2 to tobacco is unknown. To this end, CYP82E5-specific primers were designed to amplify a genomic fragment of the CYP82E5 genes from tobacco and the NtabCYP82E5v2-donating progenitor. PCR amplifications produce a distinct 2243 bp product when genomic DNA isolated from tobacco or *N. tomentosiformis* is used as template, but amplicons are not detected when genomic DNA of *N. sylvestris* is amplified indicating that NtabCYP82E5v2 was derived from *N. tomentosiformis*. DNA sequence analysis reveals that the genomic fragments of NtabCYP82E5v2 and NtomCYP82E5 contain a 1054 bp intron flanked by a 604 bp 5' and a 585 bp 3' coding region and differ at 15 positions of which nine and six are located within the coding region and intron, respectively.

Furthermore, the coding regions of ten randomly selected genomic clones isolated from tobacco share 100% nucleotide identity with the NtabCYP82E5v2 cDNA suggesting that NtabCYP82E5v2 is the only CYP82E5 variant located in DH98-325-6 tobacco.

NtabCYP82E5v2 is Expressed at Low Levels in the Green and Yellow Leaves

To investigate the catalytic role of CYP82E5 in planta, the transcriptional profile of CYP82E5v2 in the green and senescing leaves of converter (DH98-325-6) and nonconverter (DH98-325-5) Burley, converter and nonconverter Flue-Cured (SC58) tobacco, and *N. tomentosiformis* was determined using quantitative real-time (qrt)-PCR analysis.

TABLE 2

Absolute quantification of the CYP82E4v2 and CYP82E5v2 cDNA derived from the green and cured leaves of *N. tomentosiformis* and different tobacco genotypes by quantitative real-time polymerase chain reaction analysis.

| Sample | CYP82E4v2 | | CYP82E5v2 | |
|---|---|---|---|---|
| | Green | Cured | Green | Cured |
| | | Pg | | |
| *N. tomentosiformis* | 0.35c | 17.94e | 1.73d | 0.18c |
| | (0.16) | (2.57) | (0.72) | (0.09) |
| DH98-325-5 | 0.0004a | 0.007b | 0.08c | 0.26c |
| | (0.0001) | 0.003) | (0.01) | (0.17) |
| DH98-325-6 | 0.004b | 26.09e | 0.137c | 0.311c |
| | (0.001) | (3.50) | (0.003) | (0.109) |
| SC58NC | 0.0006a | 0.005b | 0.070c | 0.067c |
| | (0.0001) | (0.003) | (0.012) | (0.005) |
| SC58C | 0.0006a | 1.81d | 0.11c | 0.083c |

*Means are for 1 leaf of 3 independent plants, 3 cDNA measurements per sample (n = 9), except SC58C where one plant was used (n = 3).
*Numbers followed by different letters are significantly different according to Fisher's protected LSD (0.05).

Low levels of NtabCYP82E5v2 express in the green or yellow leaves of all tobacco cultivars (see, Table 2). The expression of NtabCYP82E5v2 significantly increased in the cured versus green leaves of converter and nonconverter Burley cultivars but remained unchanged in Flue-Cured tobacco. In the green leaves of *N. tomentosiformis*, expression of NtomCYP82E5 was higher than in tobacco, but no difference was noted between the cured leaves of the two species (Table 2). To compare the expression levels of CYP82E5v2 with that of CYP82E4v2, a previously characterized nicotine demethylase gene whose transcription was shown to be sharply upregulated in senescing leaves of *N. tomentosiformis* and converter tobacco (Gavilano et al. (2007) *J. Biol. Chem.* 282: 249-256), the transcript accumulation of CYP82E4v2 was compared in the same extracts used for quantifying the CYP82E5v2 mRNA. Transcription of NtabCYP82E5v2 is significantly higher than that of NtabCYP82E4v2 in the green leaves of all tobacco cultivars, *N. tomentosiformis* and in the cured leaves of nonconverter tobacco plants. However, the trend is reversed in the cured leaves of converter tobacco and *N. tomentosiformis* (Table 2). Of the two nicotine demethylase genes characterized thus far CYP82E4v2 is the dominant factor in senescence-inducible nornicotine production in *N. tomentosiformis* and tobacco. In addition, the activity of NtabCYP82E5v2 is the key determinant of nicotine conversion in the green leaves of tobacco.

Example 2: Sequence Identity to Cytochrome P450 Gene Family Members

Even though CYP82E5v2 and CYP82E4v2 are both nicotine demethylases, they have less sequence homology to each other than CYP82E5v2 does to CYP82E3, for example.

TABLE 3

Amino acid sequence identity shared between the CYP82E4v2 nicotine demethylase enzyme and the other CYP82E2 proteins that have been assayed for nicotine demethylase activity.

|  | CYP82E4v6 | CYP82E4v12 | 58-166 | CYP82E3 | CYP82E2v1 | CYP82E2v2 | CYP82E5v2 |
|---|---|---|---|---|---|---|---|
| CYP82E4v2 SEQ ID NO: 13 | 99.6% | 99.4% | 94.8% | 94.2% | 92.6% | 92.6% | 91.1% |

CYP82E5v2 and CYP82E4v2 are the only proteins represented that have nicotine demethylase activity.

TABLE 4

Amino acid sequence identity shared between the CYP82E4v2 nicotine demethylase enzyme and other CYP82E2 proteins.

|  | CYP82E4v2 | CYP82E3 | CYP82E2 |
|---|---|---|---|
| CYP82E5v2 SEQ ID NO: 2 | 91.1% | 91.9% | 91.3% |

CYP82E5v2 and CYP82E4v2 are the only proteins represented that have nicotine demethylase activity.

TABLE 5

Expression profiles for the CYP82E2 gene family members that have been assayed for nicotine demethylase activity.

| CYP82E4v2 | CYP82E4v6 | CYP82E4v12 | 58-166 | CYP82E3 | CYP82E2v1 | CYP82E2v2 | CYP82E5v2 |
|---|---|---|---|---|---|---|---|
| Extremely Low in Green Leaf; Extremely High in Ethylene-Induced Senescent Leaf | Low in Green Leaf; High in Ethylene-Induced Senescent Leaf | Not Reported | Extremely Low In Both Green and Ethylene-Induced Senescent Leaves | Low In Both Green and Ethylene-Induced Senescent Leaves | Extremely Low in Green Leaf; Extremely High in Ethylene-Induced Senescent Leaf | Not Reported | Low in Green Leaf; Very Low in Ethylene-Induced Senescent Leaf |

CYP82E5v2 and CYP82E4v2 are the only proteins represented that were positive for nicotine demethylase activity.

Example 3: mutations in CYP82E4V2 AND CYP82E5V2

Obtaining EMS-derived variants of CYP82E4v2

To facilitate the introduction of random mutations into the tobacco genome, thousands of seeds of the strong Converter Burley line DH98-325-6 were treated with the chemical mutagene ethyl methane sulphonate (EMS). Approximately 4000 mutagenized plants (Mo generation) were grown in the field and allowed to self-pollinate. Several capsules from each individual plant were combined to create discrete $M_1$ seed populations, each corresponding to an individual Mo plant. Genomic DNAs were isolated from young leaf tissue of a single greenhouse-grown $M_1$ plant from each $M_1$ seed pool. To identify plants carrying mutations in the CYP82E4v2 gene, specific primers were designed to independently amplify each of the gene's two exons. DNA sequence information was obtained using 96-well high-throughput sequence analysis of the amplification products. The complete analysis of 96 individual plants involved 4 separate 96-well sequencing reactions: forward and reverse sequencing of the exon 1 amplification product, and forward and reverse sequencing of the exon 2 PCR product.

Mutations were identified by conducting a multi-sequence alignment of all 96 sequences for a given run and looking for deviations from the wild-type sequence. Any given mutation that occurred in a parental $M_0$ plant would be expected to be segregating in 1:2:1 ratio in the $M_1$ generation for the mutant versus wild-type alleles. $M_1$ plants that are homozygous for an EMS-induced mutation are readily recognized as polymorphisms deviating from the wild type sequence, verified in both directions. $M_1$ plants that are heterozygous for a mutation in CYP82E4v2 would be expected to have the mutant and wild type alleles each representing 50% of the amplification product. Upon sequencing, the location of such a mutation would be expected to be annotated as an "N", since the fluorescence reading at that site would be a mixture of two alternative bases. The appearance of an "N" at the same nucleotide location using the complementary primers, combined with visual inspection of the corresponding chromatograms distinguishes plants that are truly heterozygous for a mutation in CYP82E4v2, and differentiate these true heterozygotes from artifactual sequence anomalies.

Mutations in CYP82E4v2

High-throughput sequence analysis of 672 independent $M_1$ plants resulted in the identification of eleven individuals possessing point mutations within the CYP82E4v2 gene (see, Table 6). Six of the eleven plants identified carrying CYP82E4v2 mutations are homozygous for the mutant allele (see, Table 6). All eleven mutations result in changes in the predicted amino acid sequence of the encoded protein.

TABLE 6

$M_1$ Lines of EMS Treated DH98-325-6 Plants Possessing Mutations in the CYP82E4v2 Gene.

| Plant Line | Nucleotide Mutation* | Amino Acid Change** | Zygosity of Mutant Allele |
|---|---|---|---|
| DH98-325-6 #101 | C1372T | P458S | Homozygous |
| DH98-325-6 #121 | G1092T | K364N | Homozygous |
| DH98-325-6 #164 | C113T | P38L | Homozygous |
| DH98-325-6 #321 | G601A | E201K | Heterozygous |
| DH98-325-6 #377 | G506A | R169Q | Heterozygous |
| DH98-325-6 #569 | G1375A | G459R | Heterozygous |
| DH98-325-6 #506 | G886A | E296K | Heterozygous |
| DH98-325-6 #453 | C1280T | T427I | Heterozygous |
| DH98-325-6 #775 | G986A | W329Stop | Homozygous |

TABLE 6-continued

M₁ Lines of EMS Treated DH98-325-6 Plants
Possessing Mutations in the CYP82E4v2 Gene.

| Plant Line | Nucleotide Mutation* | Amino Acid Change** | Zygosity of Mutant Allele |
|---|---|---|---|
| DH98-325-6 #610 | G1126A | V376M | Homozygous |
| DH98-325-6 #761 | G511A | D171N | Homozygous |

*Nucleotide location is in reference to the ATG initiator codon of the CYP82E4v2 cDNA (see SEQ ID NO: 50). Nucleotide to the left of the number represents the wild type residue, whereas the nucleotide on the right indicates the mutant residue (e.g. C1372T means that the C residue normally located at position 1372 was mutated to a T residue).
**Amino acid location is in reference to the initiator methionine of the CYP82E4v2 polypeptide (see SEQ ID NO: 13). Amino acid to the left of the number represents the wild type residue, whereas the amino acid on the right indicates the residue produced by the mutant allele (e.g. P458S means that the Proline residue normally located at position 458 of the protein sequence has been changed to a Serine). "Stop" indicates the introduction of a premature stop codon.

Plant #775 possesses a mutation at codon 329 which changes a tryptophan codon (TGG) into a premature stop codon (TAG). This mutation renders the encoded protein completely nonfunctional given that the essential heme-binding domain and other highly conserved regions of the enzyme are located downstream of codon 329. Other plants contain mutations affecting highly conserved motifs shared by the vast majority of P450 enzymes include: plant #101 (where a conserved Pro residue immediately adjacent to the heme-binding Cys amino acid is change to a Ser); plant #164 (Pro residue within the highly conserved Pro-rich "hinge" region of the protein changed to a Leu); and plant #569 (Gly residue that's part of the very highly conserved heme-binding motif changed to an Arg).

Alkaloid Analysis of CYP82E4v2 Variants

An alkaloid analysis was conducted on cured leaves of variant individuals to assess the effect of the mutation on the metabolic conversion of nicotine to nornicotine. As shown in Table 7, three individuals (#101, #121 and #775) show conversion rates similar to nonconverter control plants grown from seed lots that had been screened to eliminate converter individuals (TN90 LC plants). The variant CYP82E4v2 enzymes produced in these plants are completely (or nearly completely) nonfunctional. Two plants (#164 and #761) display high conversion rates and have no detrimental effect on enzyme activity. This result for plant #164 is surprising given that it contains a Pro to Leu mutation within one of the residues defining the highly conserved Pro-rich hinge motif. The Val to Met modification at residue 376 partially inhibits enzyme function as the homozygous mutant plant (#610) shows an intermediate conversion phenotype (41.5%).

The substitution of the Lys residue at position 364 to an Asn of plant #121 within this plant does not occur in any motif conserved among P450 enzymes, nor within any region predicted by Xu et al. (*Physiologia Plantarum* 129: 307-319, 2007) to be a substrate recognition site. A BLAST alignment against protein sequences deposited in GenBank reveals several P450s that possess an Asn residue at the analagous position (e.g. the CYP82A1 gene of Pea—accession number Q43068). The variant CYP82E4v2 gene in plant #121 is completely inactive. Another anomaly with plant #121 lies in the nature of EMS-induced mutations. EMS is known to induce mutations through the alkylation of G residues, resulting in G to A or C to T transition mutations (Anderson, *Methods Cell Biol.* 48:31-58, 1995). Very rarely does EMS lead to a G to T transversion mutation such as that found in plant #121 (see, Table 3). All other mutations described for either the CYP82E4v2 or CYP82E5v2 genes are the expected G to A or C to T transition mutations.

Mutations in CYP82E5v2

A similar high-throughput sequencing strategy was used to identify mutations in CYP82E5v2, the other confirmed nicotine N-demethylase gene that is found within the tobacco genome. A screen of 768 M₁ plants revealed 11 individuals possessing mutations in CYP82E5v2 (see, Table 8). Three plants (#744, #561 and #340) contain silent nucleotide substitutions that did not alter the predicted protein sequence. Of the eight mutations that lead to changes in the protein sequence, two are of particular note. Plant #1013 contains a mutation that would lead to a truncated product that should render the product completely nonfunctional. The G to A mutation at position 1266 changes a Trp codon (TGG) into a premature stop codon (TGA). The predicted CYP82E5v2 protein produced from this truncated reading frame lacks the final 96 amino acids of the enzyme, a region that includes the essential heme-binding domain. Without being limited by mechanism, this truncated protein is probably incapable of catalyzing the oxidative elimination of the N' methyl group of nicotine to form nornicotine. Whatever the mechanism, the #1013 plant has a nonfunctional CYP82E5v2 allele. Plant #680 possesses a mutation that changes a Pro residue at position 449 to a Leu. This Pro is well conserved in plant P450s and lies immediately adjacent to the F-x-x-G-x-R-x-C-x-G motif that defines the heme binding region. The mutation found in plant #680 has a negative impact on enzyme function.

TABLE 7

Alkaloid Content as Percent Dry Weight of M₁ Plants
Homozygous for Mutations in the CYP82E4v2 Gene

| Plant | Nicotine | Nornicotine | Anabasine | Anatabine | % Conversion* |
|---|---|---|---|---|---|
| DH98-325-6 #101 | 2.17 | 0.0376 | 0.00514 | 0.0384 | 1.7% |
| DH98-325-6 #121 | 2.5 | 0.0333 | 0.00557 | 0.043 | 1.3% |
| DH98-325-6 #164 | 0.216 | 0.84 | 0.00499 | 0.0532 | 79.5% |
| DH98-325-6 #610 | 0.214 | 0.152 | 0.00429 | 0.0121 | 41.5% |
| DH98-325-6 #761 | 0.214 | 0.999 | 0.00429 | 0.0426 | 82.4% |
| DH98-325-6 #775 | 0.505 | 0.0159 | 0.00417 | 0.0136 | 3.1% |
| SC58 CtCt (Control)† | 0.206 | 0.565 | 0.00412 | 0.0197 | 73.3% |
| TN90 LC (Control) | 3.11 | 0.0647 | 0.00901 | 0.0487 | 2.0% |
| TN90 LC (Control) | 2.46 | 0.0521 | 0.00846 | 0.0417 | 2.1% |

*[% nornicotine/(% nicotine + % nornicotine)] × 100
†A converter plant of flue-cured genotype SC58 is used as a strong converter control; two plants of genotype TN90 selected from lots screened for low converters (LC) are used as nonconverter controls.

TABLE 8

M₁ Lines of EMS Treated DH98-325-6 Plants Possessing Mutations in the CYP82E5v2 Gene

| Plant Line | Nucleotide Mutation* | Amino Acid Change** | Zygosity of Mutant Allele |
|---|---|---|---|
| DH98-325-6 #198 | C703T | P235S | Heterozygous |
| DH98-325-6 #680 | C1346T | P449L | Homozygous |
| DH98-325-6 #744 | G558A | None | Homozygous |
| DH98-325-6 #163 | C521T | S174L | Heterozygous |
| DH98-325-6 #561 | G1458A | None | Heterozygous |
| DH98-325-6 #154 | C1229T | A410V | Heterozygous |
| DH98-325-6 #340 | G1248A | None | Heterozygous |
| DH98-325-6 #780 | G672A | M224I | Heterozygous |
| DH98-325-6 #799 | C215T | P72L | Heterozygous |
| DH98-325-6 #540 | C427T | L143F | Heterozygous |
| DH98-325-6 #1013 | G1266A | W422Stop | Homozygous |

*Nucleotide location is in reference to the ATG initiator codon of the CYP82E5v2 cDNA (see SEQ ID NO: 1). Nucleotide to the left of the number represents the wild type residue, whereas the nucleotide on the right indicates the mutant residue (e.g. C703T means that the C residue normally located at position 703 was mutated to a T residue).
**Amino acid location is in reference to the initiator methionine of the CYP82E5v2 polypeptide (see SEQ ID NO: 2). Amino acid to the left of the number represents the wild type residue, whereas the amino acid on the right indicates the residue produced by the mutant allele (e.g. P235S means that the Proline residue normally located at position 235 of the protein sequence has been changed to a Serine). "Stop" indicates the introduction of a premature stop codon. "None" indicates mutations resulting in silent substitutions that did not alter the predicted amino acid sequence.

Plants with Mutations in CYP82E4v2 and CYP82E5v2

Tobacco plant lines are generated that show uniformity and stability within the limits of environmental influence for reduced conversion of nicotine to nornicotine at levels of about 0.5% when a plant with a mutation that inhibits nicotine demethylase activity of CYP82E4v2 is crossed with a plant having a mutation that inhibits nicotine demethylase activity of CYP82E5v2.

An illustrative cross is between a CYP82E4v2 mutant plant (of Table 9) and a CYP82E5v2 mutant plant (of Table 9).

TABLE 9

Illustrative Crosses of DH98-325-6 Plants Possessing Mutations in the CYP82E5v2 and CYP82E4v2 Genes

| CYP82E5v2 |
|---|
| DH98-325-6 #198 |
| DH98-325-6 #680 |
| DH98-325-6 #163 |
| DH98-325-6 #154 |
| DH98-325-6 #780 |
| DH98-325-6 #799 |
| DH98-325-6 #540 |
| DH98-325-6 #1013 |
| CYP82E4v2 |
| DH98-325-6 #101 |
| DH98-325-6 #121 |
| DH98-325-6 #775 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A tobacco seed, a tobacco plant grown therefrom, or a part of said tobacco plant, wherein said tobacco seed, tobacco plant grown therefrom, or part of said tobacco plant comprises a variant polynucleotide comprising a non-natural mutation as compared to a reference sequence, wherein said reference sequence comprises at least 95% sequence identity compared to SEQ ID NO:4, and wherein said non-natural mutation is positioned between two sequences corresponding to SEQ ID NOs: 36 and 37.

2. The tobacco seed, a tobacco plant grown therefrom, or a part of said tobacco plant, according to claim 1, wherein said non-natural mutation is selected from the group consisting of a substitution, an addition, and a deletion of at least one nucleotide.

3. The tobacco seed, a tobacco plant grown therefrom, or a part of said tobacco plant, according to claim 2, wherein said non-natural mutation is a null mutation.

4. The tobacco seed, a tobacco plant grown therefrom, or a part of said tobacco plant, according to claim 2, wherein said tobacco plant is homozygous for said non-natural mutation.

5. The tobacco seed, a tobacco plant grown therefrom, or a part of said tobacco plant, according to claim 1, wherein said polynucleotide encodes a polypeptide that is not biologically active.

6. The tobacco seed, a tobacco plant grown therefrom, or a part of said tobacco plant, according to claim 1, wherein said tobacco plant comprises a lower level of nornicotine or N'-nitrosonornicotine compared to a tobacco plant comprising a wild type allele.

7. The tobacco seed, a tobacco plant grown therefrom, or a part of said tobacco plant, according to claim 1, wherein the conversion of nicotine to nornicotine in tobacco material cured from said tobacco plant is selected from the group consisting of less than 0.3%, less than 0.5%, less than 0.7%, between 0.1%-0.5%, between 0.1%-0.4%, between 0.1%-0.7%, and between 0.1%-1.0%.

8. The tobacco seed, a tobacco plant grown therefrom, or a part of said tobacco plant, according to claim 1, wherein said tobacco plant has a non-converter phenotype.

9. The tobacco seed, a tobacco plant grown therefrom, or a part of said tobacco plant, according to claim 1, wherein said tobacco plant is selected from the group consisting of a Burley type, a dark type, a flue-cured type, and an Oriental type.

10. The tobacco seed, a tobacco plant grown therefrom, or a part of said tobacco plant, according to claim 1, wherein said seed, plant, or part further comprises a second variant polynucleotide comprising a second non-natural mutation as compared to a second reference sequence, wherein said second reference sequence comprises at least 95% sequence identity compared to SEQ ID NO:13.

11. A tobacco seed, a tobacco plant grown therefrom, or a part of said tobacco plant, wherein said tobacco seed, tobacco plant grown therefrom, or part of said tobacco plant comprises a variant polynucleotide comprising a non-natural mutation in a conserved residue of a polypeptide encoded by a reference sequence wherein said reference sequence comprises SEQ ID NO:4, wherein said conserved residue is a conserved residue unchanged between SEQ ID NOs: 2, 13, 26, 27, 28, 29, 30, and 31; and wherein said variant polynucleotide comprises at least 95% sequence identity compared to SEQ ID NO:4.

12. The tobacco seed, a tobacco plant grown therefrom, or a part of said tobacco plant, according to claim 11, wherein said non-natural mutation is selected from the group consisting of a substitution, an addition, and a deletion of at least one nucleotide.

13. The tobacco seed, a tobacco plant grown therefrom, or a part of said tobacco plant, according to claim 11, wherein said non-natural mutation is a null mutation.

14. The tobacco seed, a tobacco plant grown therefrom, or a part of said tobacco plant, according to claim 11, wherein said tobacco plant is homozygous for said non-natural mutation.

15. The tobacco seed, a tobacco plant grown therefrom, or a part of said tobacco plant, according to claim 11, wherein said variant polynucleotide encodes a polypeptide that is not biologically active.

16. The tobacco seed, a tobacco plant grown therefrom, or a part of said tobacco plant, according to claim 11, wherein said tobacco plant comprises a lower level of nornicotine or N'-nitrosonornicotine compared to a tobacco plant not comprising said non-natural mutation.

17. The tobacco seed, a tobacco plant grown therefrom, or a part of said tobacco plant, according to claim 11, wherein the conversion of nicotine to nornicotine in tobacco material cured from said tobacco plant is selected from the group consisting of less than 0.3%, less than 0.5%, less than 0.7%, between 0.1%-0.5%, between 0.1%-0.4%, between 0.1%-0.7%, and between 0.1%-1.0%.

18. The tobacco seed, a tobacco plant grown therefrom, or a part of said tobacco plant, according to claim 11, wherein said tobacco plant has a non-converter phenotype.

19. The tobacco seed, a tobacco plant grown therefrom, or a part of said tobacco plant, according to claim 11, wherein said seed, plant, or part further comprises a second variant polynucleotide comprising a second non-natural mutation as compared to a second reference sequence, wherein said second reference sequence comprises at least 95% sequence identity compared to SEQ ID NO: 13.

20. The tobacco seed, a tobacco plant grown therefrom, or a part of said tobacco plant, according to claim 11, wherein said tobacco plant is selected from the group consisting of a Burley type, a dark type, a flue-cured type, and an Oriental type.

21. The tobacco seed, a tobacco plant grown therefrom, or a part of said tobacco plant, according to claim 11, wherein said variant polynucleotide comprises at least 98% sequence identity compared to SEQ ID NO:4.

* * * * *

SEQUENCE LISTING

<160> NUMBER OF SEQ ID NOS: 50

<210> SEQ ID NO 1
<211> LENGTH: 1554
<212> TYPE: DNA
<213> ORGANISM: Nicotiana tabacum

<400> SEQUENCE: 1

```
atggtttctc ccgtagaagc cattgtagga ctagtaaccc ttacacttct cttctacttc      60
ctatggccca aaaatttca aataccttca aaaccattac caccgaaaat tcccggaggg     120
tggccggtaa tcggccatct tttctacttc gatgatgacg gcgacgaccg tccattagct     180
cgaaaactcg gagacttagc tgacaaatac ggcccggttt tcacttttccg gctaggccttt     240 ccgcttgtgt tagttgtaag cagttacgaa gctgtaaaag actgcttctc tacaaatgac     300
gccattttct ccaatcgtcc agcttttctt tacggtgaat accttggcta cagtaatgcc     360
atgctatttt tgacaaaata cggaccttat tggcgaaaaa atagaaaatt agtcattcag     420
gaagttctct ctgctagtcg tctcgaaaaa ttgaagcacg tgagatttgg taaaattcaa     480
acgagcatta agagtttata cactcgaatt gatggaaatt cgagtacgat aaatctaact     540
gattggttag aagaattgaa ttttggtctg atcgtgaaaa tgatcgctgg gaaaaattat     600
gaatccggta aaggagatga acaagtggag agatttagga aagcgtttaa ggattttata     660 atttatcaa tggagtttgt gttatgggat gcttttccaa ttccattgtt caaatgggtg     720
gattttcaag gccatgttaa ggccatgaaa aggacattta aggatataga ttctgttttt     780
cagaattggt tagaggaaca tgtcaagaaa agagaaaaaa tggaggttaa tgcacaaggg     840
```

```
aatgaacaag atttcattga tgtggtgctt tcaaaaatga gtaatgaata tcttgatgaa    900
ggttactctc gtgatactgt cataaaagca acagtgttta gtttggtctt ggatgctgcg    960
gacacagttg ctcttcacat gaattgggga atggcattac tgataaacaa tcaacatgcc   1020
ttgaagaaag cacaagaaga gatcgataaa aaagttggta aggaaagatg ggtagaagag   1080
agtgatatta aggatttggt ctacctccaa gctattgtta agaagtgtt acgattatat    1140
ccaccaggac ctttattagt acctcatgaa aatgtagagg attgtgttgt tagtggatat   1200
cacattccta aagggactag actattcgcg aacgttatga aattgcagcg cgatcctaaa   1260
ctctggtcaa atcctgataa gtttgatcca gagagattct tcgctgatga tattgactac   1320
cgtggtcagc actatgagtt tatcccattt ggttctggaa gacgatcttg tccggggatg   1380
acttatgcat acaagcgga acacctaaca atagcacatt tgatccaggg tttcaattac    1440
aaaactccaa atgacgagcc cttggatatg aaggaaggtg caggattaac tatacgtaaa   1500
gtaaatcctg tagaagtgac aattacggct cgcctggcac ctgagcttta ttaa          1554
```

<210> SEQ ID NO 2
<211> LENGTH: 517
<212> TYPE: PRT
<213> ORGANISM: Nicotiana tabacum

<400> SEQUENCE: 2

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
```

```
                    245                 250                 255
Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
        340                 345                 350

Gly Lys Glu Arg Trp Val Glu Glu Ser Asp Ile Lys Asp Leu Val Tyr
    355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
        420                 425                 430

Phe Phe Ala Asp Asp Ile Asp Tyr Arg Gly Gln His Tyr Glu Phe Ile
    435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
        500                 505                 510

Ala Pro Glu Leu Tyr
        515

<210> SEQ ID NO 3
<211> LENGTH: 1054
<212> TYPE: DNA
<213> ORGANISM: Nicotiana tabacum

<400> SEQUENCE: 3
gtaagttcat tttcattttt cattattcag tctgattttg aggaatagac aggttaataa    60
taatttaagt aattagatta tctaaatact aaggatgatt atatatagta aaaatgtaga   120
atgataaatg gaaaaagat gagaattctt tgtgcctcga ctaatctata tatctttggg   180
agttaaaagt gcttcaccaa agggactttt tcctcatagc tcaagttaga gtttgatta   240 tagatgaaag agtatttatc acttcacgaa ctctgatgat aaaagtaaat gagatataac   300
cagttataat tgatagaata aaacttcatt actcccattg agcataaaaa aaaaagtaaa   360
agggacttct tctctttttt ttagggagaa attcttaaat tgtttgttaa atatagattc   420 atgtttttt ttcttctat ttctaataat aatggttctt gaatcaggtc gttgactttg   480
tagcagcaat atagtcaaag ctaatatcca tgttatttgg ttttcgaaca agttatactg   540
```

```
aaattatata tacgggtatt aaataataac attattattt ataggatata cttttttat        600 tgggtaaata ttacaacaac aacaactgac tcagtgaaat tttactagtg gggtatgggg        660
agggtagtgt gtatgcagac cttaccccta ccccgaagga gtagagggat tgtttccgaa        720
agaccctcgg ctcaagaaaa caaaagaga caatatcagt accaccacag atcatattat         780
taggtaaatg ttatttttatt gaattaaaga tgaaatatac aggtaaggta taaaacgtgt       840
atttgatttt acactagata aatttgacct cgtacatctc taagagaaag ctgaaataaa        900
tgaattttag atttaaaaaa aaaattcatt agtataatga gatgtgcata cttgacaatt       960
actatactaa atagaacaag gttcggcaga tagtgcacact aacctacttt tgcattgaat      1020
tatccttttt aattttattc taatttgtct acag                                   1054

<210> SEQ ID NO 4
<211> LENGTH: 2608
<212> TYPE: DNA
<213> ORGANISM: Nicotiana tabacum

<400> SEQUENCE: 4
atggtttctc ccgtagaagc cattgtagga ctagtaaccc ttacacttct cttctacttc        60
ctatggccca aaaatttca ataccttca aaaccattac caccgaaaat tcccggaggg         120
tggccggtaa tcggccatct tttctacttc gatgatgacg gcgacgaccg tccattagct       180
cgaaaactcg gagacttagc tgacaaatac ggcccggttt tcactttccg gctaggcctt      240
ccgcttgtgt tagttgtaag cagttacgaa gctgtaaaag actgcttctc tacaaatgac      300 gccatttctct ccaatcgtcc agcttttctt tacggtgaat accttggcta cagtaatgcc      360
atgctatttt tgacaaaata cggaccttat tggcgaaaaa atagaaaatt agtcattcag       420
gaagttctct ctgctagtcg tctcgaaaaa ttgaagcacg tgagatttgg taaaattcaa       480
acgagcatta agagtttata cactcgaatt gatggaaatt cgagtacgat aaatctaact      540
gattggttag aagaattgaa ttttggtctg atcgtgaaaa tgatcgctgg gaaaaattat       600
gaatccggta aaggagatga acaagtggag agatttagga aagcgtttaa ggattttata       660 atttatcaa tggagtttgt gttatgggat gcttttccaa ttccattgtt caaatgggtg       720
gattttcaag gccatgttaa ggccatgaaa aggacattta aggatataga ttctgttttt       780
cagaattggt tagaggaaca tgtcaagaaa agagaaaaaa tggaggttaa tgcacaaggg       840
aatgaacaag atttcattga tgtggtgctt tcaaaaatga gtaatgaata tcttgatgaa       900
ggttactctc gtgatactgt cataaaaagca acagtgtttg taagttcatt ttcatttttc       960
attattcagt ctgattttga ggaatagaca ggttaataat aatttaagta attagattat       1020
ctaaatacta aggatgatta tatatagtaa aaatgtagaa tgataaatgg aaaaaagatg       1080
agaattcttt gtgcctcgac taatctatat atctttggga gttaaaagtg cttcaccaaa       1140
ggggactttt cctcatagct caagttagaa gtttgattat agatgaaaga gtatttatca       1200
cttcacgaac tctgatgata aaagtaaatg agatataacc agttataatt gatagaataa       1260
aacttcatta ctcccattga gcataaaaaa aaaagtaaaa gggacttctt ctctttttt       1320 tagggagaaa ttcttttaatt gtttgttaaa tatagattca tgttttttt ttcttctatt      1380 tctaataata atggttcttg aatcaggtcg ttgactttgt agcagcaata tagtcaaagc       1440
taatatccat gttatttggt tttcgaacaa gttatactga aattatatat acgggtatta       1500
aataataaca ttattattta taggatatac ttttttttatt gggtaaatat tacaacaaca      1560
acaactgact cagtgaaatt ttactagtgg ggtatgggga gggtagtgtg tatgcagacc       1620
```

```
ttaccccta ccccgaaggag tagagggatt gtttccgaaa gaccctcggc tcaagaaaac    1680
aaaaagagac aatatcagta ccaccacaga tcatattatt aggtaaatgt tattttattg    1740
aattaaagat gaaatataca ggtaaggtat aaaacgtgta tttgatttta cactagataa    1800
atttgacctc gtacatctct aagagaaagc tgaaataaat gaattttaga tttaaaaaaa    1860
aaattcatta gtataatgag atgtgcatac ttgacaatta ctatactaaa tagaacaagg    1920
ttcggcagat agtgacacta acctactttt gcattgaatt atccttttta attttattct    1980
aatttgtcta cagagtttgg tcttggatgc tgcggacaca gttgctcttc acatgaattg    2040
gggaatggca ttactgataa acaatcaaca tgccttgaag aaagcacaag aagagatcga    2100
taaaaaagtt ggtaaggaaa gatgggtaga agagagtgat attaaggatt tggtctacct    2160
ccaagctatt gttaagaag tgttacgatt atatccacca ggacctttat tagtacctca    2220
tgaaaatgta gaggattgtg ttgttagtgg atatcacatt cctaagggaa ctagactatt    2280
cgcgaacgtt atgaaattgc agcgcgatcc taaactctgg tcaaatcctg ataagtttga    2340
tccagagaga ttcttcgctg atgatattga ctaccgtggt cagcactatg agtttatccc    2400
atttggttct ggaagacgat cttgtccggg gatgacttat gcattacaag cggaacacct    2460
aacaatagca catttgatcc agggtttcaa ttacaaaact ccaaatgacg agcccttgga    2520
tatgaaggaa ggtgcaggat taactatacg taaagtaaat cctgtagaag tgacaattac    2580
ggctcgcctg gcacctgagc tttattaa                                       2608
```

<210> SEQ ID NO 5
<211> LENGTH: 517
<212> TYPE: PRT
<213> ORGANISM: Nicotiana tabacum

<400> SEQUENCE: 5

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190
```

```
Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Ser Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 6
<211> LENGTH: 517
<212> TYPE: PRT
<213> ORGANISM: Nicotiana tabacum

<400> SEQUENCE: 6

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45
```

```
Tyr Phe Asp Asp Asp Gly Asp Arg Pro Leu Ala Arg Lys Leu Gly
     50                  55                  60
Asp Leu Ala Asp Lys Tyr Gly Pro Val Phe Thr Phe Arg Leu Gly Leu
 65                  70                  75                  80
Pro Leu Val Leu Val Ser Ser Tyr Glu Ala Val Lys Asp Cys Phe
                 85                  90                  95
Ser Thr Asn Asp Ala Ile Phe Ser Asn Arg Pro Ala Phe Leu Tyr Gly
             100                 105                 110
Glu Tyr Leu Gly Tyr Ser Asn Ala Met Leu Phe Leu Thr Lys Tyr Gly
             115                 120                 125
Pro Tyr Trp Arg Lys Asn Arg Lys Leu Val Ile Gln Glu Val Leu Ser
    130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Arg Glu
            260                 265                 270
Lys Met Glu Val Asn Ala Gln Gly Asn Glu Gln Asp Phe Ile Asp Val
        275                 280                 285
Val Leu Ser Lys Met Ser Asn Glu Tyr Leu Asp Glu Gly Tyr Ser Arg
    290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
            340                 345                 350
Gly Lys Glu Arg Trp Val Glu Glu Ser Asp Ile Lys Asp Leu Val Tyr
        355                 360                 365
Leu Gln Ala Ile Val Lys Glu Val Leu Arg Leu Tyr Pro Pro Gly Pro
    370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
            420                 425                 430
Phe Phe Ala Asp Asp Ile Asp Tyr Arg Gly Gln His Tyr Glu Phe Ile
        435                 440                 445
Leu Phe Gly Ser Gly Arg Arg Ser Cys Pro Gly Met Thr Tyr Ala Leu
    450                 455                 460
```

```
Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 7
<211> LENGTH: 517
<212> TYPE: PRT
<213> ORGANISM: Nicotiana tabacum

<400> SEQUENCE: 7

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Leu Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
                260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320
```

-continued

```
Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 8
<211> LENGTH: 517
<212> TYPE: PRT
<213> ORGANISM: Nicotiana tabacum

<400> SEQUENCE: 8

Met Val Ser Pro Val Glu Ala Ile Val Gly Leu Val Thr Leu Thr Leu
1               5                  10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
```

```
                  165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Val Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 9
<211> LENGTH: 517
<212> TYPE: PRT
<213> ORGANISM: Nicotiana tabacum

<400> SEQUENCE: 9

Met Val Ser Pro Val Glu Ala Ile Val Gly Leu Val Thr Leu Thr Leu
1               5                   10                  15
```

```
Leu Phe Tyr Phe Leu Trp Pro Lys Lys Phe Gln Ile Pro Ser Lys Pro
                 20                  25                  30

Leu Pro Pro Lys Ile Pro Gly Gly Trp Pro Val Ile Gly His Leu Phe
             35                  40                  45

Tyr Phe Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Ile
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
```

```
                435                 440                 445
Pro Phe Gly Ser Gly Arg Arg Ser Cys Pro Gly Met Thr Tyr Ala Leu
450                 455                 460
Gln Ala Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Val Glu Val Thr Ile Thr Ala Arg Leu
            500                 505                 510
Ala Pro Glu Leu Tyr
            515

<210> SEQ ID NO 10
<211> LENGTH: 517
<212> TYPE: PRT
<213> ORGANISM: Nicotiana tabacum

<400> SEQUENCE: 10

Met Val Ser Pro Val Glu Ala Ile Val Gly Leu Val Thr Leu Thr Leu
1               5                   10                  15
Leu Phe Tyr Phe Leu Trp Pro Lys Lys Phe Gln Ile Pro Ser Lys Pro
                20                  25                  30
Leu Pro Pro Lys Ile Pro Gly Gly Trp Pro Val Ile Gly His Leu Phe
            35                  40                  45
Tyr Phe Asp Asp Gly Asp Asp Arg Pro Leu Ala Arg Lys Leu Gly
        50                  55                  60
Asp Leu Ala Asp Lys Tyr Gly Leu Val Phe Thr Phe Arg Leu Gly Leu
65                  70                  75                  80
Pro Leu Val Leu Val Ser Ser Tyr Glu Ala Val Lys Asp Cys Phe
                85                  90                  95
Ser Thr Asn Asp Ala Ile Phe Ser Asn Arg Pro Ala Phe Leu Tyr Gly
                100                 105                 110
Glu Tyr Leu Gly Tyr Ser Asn Ala Met Leu Phe Leu Thr Lys Tyr Gly
            115                 120                 125
Pro Tyr Trp Arg Lys Asn Arg Lys Leu Val Ile Gln Glu Val Leu Ser
        130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
                180                 185                 190
Lys Met Ile Ala Gly Lys Asn Tyr Glu Ser Gly Lys Gly Asp Glu Gln
            195                 200                 205
Val Glu Arg Phe Arg Lys Ala Phe Lys Asp Phe Ile Ile Leu Ser Met
        210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Arg Glu
                260                 265                 270
Lys Met Glu Val Asn Ala Gln Gly Asn Glu Gln Asp Phe Ile Asp Val
            275                 280                 285
```

```
Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
                340                 345                 350

Gly Lys Glu Arg Trp Val Glu Ser Asp Ile Lys Asp Leu Val Tyr
                355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Asp Asp Ile Asp Tyr Arg Gly Gln His Tyr Glu Phe Ile
                435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
                500                 505                 510

Ala Pro Glu Leu Tyr
            515

<210> SEQ ID NO 11
<211> LENGTH: 517
<212> TYPE: PRT
<213> ORGANISM: Nicotiana tabacum

<400> SEQUENCE: 11

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Phe Ser
    130                 135                 140
```

-continued

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 12
<211> LENGTH: 421
<212> TYPE: PRT
<213> ORGANISM: Nicotiana tabacum -continued

<400> SEQUENCE: 12

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415
```

Arg Asp Pro Lys Leu
        420

<210> SEQ ID NO 13
<211> LENGTH: 517
<212> TYPE: PRT
<213> ORGANISM: Nicotiana tabacum

<400> SEQUENCE: 13

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr

```
            355                 360                 365
Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 14
<211> LENGTH: 517
<212> TYPE: PRT
<213> ORGANISM: Nicotiana tabacum

<400> SEQUENCE: 14

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205
```

```
Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Ser Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 15
<211> LENGTH: 517
<212> TYPE: PRT
<213> ORGANISM: Nicotiana tabacum

<400> SEQUENCE: 15

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60
```

```
Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Val Lys Asp Cys Phe
             85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Asn Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480
```

```
Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 16
<211> LENGTH: 517
<212> TYPE: PRT
<213> ORGANISM: Nicotiana tabacum

<400> SEQUENCE: 16

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Leu Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335
```

```
Asn Gln Lys Ala Leu Thr Lys Ala Gln Glu Ile Asp Thr Lys Val
                340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 17
<211> LENGTH: 517
<212> TYPE: PRT
<213> ORGANISM: Nicotiana tabacum

<400> SEQUENCE: 17

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
```

```
            180                 185                 190
Lys Met Ile Ala Gly Lys Asn Tyr Lys Ser Gly Lys Gly Asp Glu Gln
            195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ala Pro Arg Leu
            500                 505                 510

Ala Pro Glu Leu Tyr
            515

<210> SEQ ID NO 18
<211> LENGTH: 517
<212> TYPE: PRT
<213> ORGANISM: Nicotiana tabacum

<400> SEQUENCE: 18

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30
```

```
Leu Pro Pro Lys Ile Pro Gly Gly Trp Pro Val Ile Gly His Leu Phe
        35              40              45
His Phe Asn Asp Asp Gly Asp Asp Arg Pro Leu Ala Arg Lys Leu Gly
 50              55              60
Asp Leu Ala Asp Lys Tyr Gly Pro Val Phe Thr Phe Arg Leu Gly Leu
 65              70              75              80
Pro Leu Val Leu Val Val Ser Ser Tyr Glu Ala Val Lys Asp Cys Phe
             85              90              95
Ser Thr Asn Asp Ala Ile Phe Ser Asn Arg Pro Ala Phe Leu Tyr Gly
        100             105             110
Asp Tyr Leu Gly Tyr Asn Asn Ala Met Leu Phe Leu Ala Asn Tyr Gly
        115             120             125
Pro Tyr Trp Arg Lys Asn Arg Lys Leu Val Ile Gln Glu Val Leu Ser
        130             135             140
Ala Ser Arg Leu Glu Lys Phe Lys His Val Arg Phe Ala Arg Ile Gln
145             150             155             160
Ala Ser Ile Lys Asn Leu Tyr Thr Gln Ile Asp Gly Asn Ser Ser Thr
        165             170             175
Ile Asn Leu Thr Asp Trp Leu Glu Glu Leu Asn Phe Gly Leu Ile Val
        180             185             190
Lys Met Ile Ala Gly Lys Asn Tyr Glu Ser Gly Lys Gly Asp Glu Gln
        195             200             205
Val Glu Arg Phe Lys Lys Ala Phe Lys Asp Phe Met Ile Leu Ser Met
        210             215             220
Glu Phe Val Leu Trp Asp Ala Phe Pro Ile Pro Leu Phe Lys Trp Val
225             230             235             240
Asp Phe Gln Gly His Val Lys Ala Met Lys Arg Thr Phe Lys Asp Ile
        245             250             255
Asp Ser Val Phe Gln Asn Trp Leu Glu Glu His Ile Asn Lys Arg Glu
        260             265             270
Lys Met Glu Val Asn Ala Glu Gly Asn Glu Gln Asp Phe Ile Asp Val
        275             280             285
Val Leu Ser Lys Met Ser Asn Glu Tyr Leu Gly Glu Gly Tyr Ser Arg
        290             295             300
Asp Thr Val Ile Lys Ala Thr Val Phe Ser Leu Val Leu Asp Ala Ala
305             310             315             320
Asp Thr Val Ala Leu His Ile Asn Trp Gly Met Ala Leu Leu Ile Asn
        325             330             335
Asn Gln Lys Ala Leu Thr Lys Ala Gln Glu Glu Ile Asp Thr Lys Val
        340             345             350
Gly Lys Asp Arg Trp Val Glu Glu Ser Asp Ile Lys Asp Leu Val Tyr
        355             360             365
Leu Gln Ala Ile Val Lys Glu Val Leu Arg Leu Tyr Pro Pro Gly Pro
        370             375             380
Leu Leu Val Pro His Glu Asn Val Glu Asp Cys Val Val Ser Gly Tyr
385             390             395             400
His Ile Pro Lys Gly Thr Arg Leu Phe Ala Asn Val Met Lys Leu Gln
        405             410             415
Arg Asp Pro Lys Leu Trp Ser Asp Pro Asp Thr Phe Asp Pro Glu Arg
        420             425             430
Phe Ile Ala Thr Asp Ile Asp Phe Arg Gly Gln Tyr Tyr Lys Tyr Ile
        435             440             445
Pro Phe Gly Ser Gly Arg Arg Ser Cys Pro Gly Met Thr Tyr Ala Leu
```

```
              450                 455                 460
Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 19
<211> LENGTH: 517
<212> TYPE: PRT
<213> ORGANISM: Nicotiana tabacum

<400> SEQUENCE: 19

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65              70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300
```

-continued

```
Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Arg Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ala Pro Arg Leu
            500                 505                 510

Ala Pro Glu Leu Tyr
        515

<210> SEQ ID NO 20
<211> LENGTH: 517
<212> TYPE: PRT
<213> ORGANISM: Nicotiana tabacum

<400> SEQUENCE: 20

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160
```

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Lys Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 21
<211> LENGTH: 517
<212> TYPE: PRT
<213> ORGANISM: Nicotiana tabacum

<400> SEQUENCE: 21

Met Leu Ser Pro Ile Glu Ala Ile Val Gly Leu Val Thr Phe Thr Phe

-continued

```
1               5                   10                  15
Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Arg Pro Leu Ala Arg Lys Leu Gly
            50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
                115                 120                 125

Pro Tyr Trp Arg Lys Asn Arg Lys Leu Val Ile Gln Glu Val Leu Ser
                130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
                195                 200                 205

Val Glu Arg Phe Lys Lys Ala Phe Lys Asp Phe Met Ile Leu Ser Met
                210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
                275                 280                 285

Val Leu Ser Lys Met Ser Asn Glu Tyr Leu Gly Glu Gly Tyr Ser Arg
                290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
                340                 345                 350

Gly Lys Asp Arg Trp Val Glu Glu Ser Asp Ile Lys Asp Leu Val Tyr
                355                 360                 365

Leu Gln Ala Ile Val Lys Glu Val Leu Arg Leu Tyr Pro Pro Gly Pro
                370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Ile Phe Asp Pro Glu Arg
                420                 425                 430
```

```
Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515

<210> SEQ ID NO 22
<211> LENGTH: 328
<212> TYPE: PRT
<213> ORGANISM: Nicotiana tabacum

<400> SEQUENCE: 22

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
```

-continued

```
            275                 280                 285
Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 23
<211> LENGTH: 517
<212> TYPE: PRT
<213> ORGANISM: Nicotiana tabacum

<400> SEQUENCE: 23

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320
```

```
Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Met Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 24
<211> LENGTH: 517
<212> TYPE: PRT
<213> ORGANISM: Nicotiana tabacum

<400> SEQUENCE: 24

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asn Gly Asn Ser Ser Thr
                165                 170                 175
```

```
Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 25
<211> LENGTH: 517
<212> TYPE: PRT
<213> ORGANISM: Nicotiana tabacum

<400> SEQUENCE: 25

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
```

-continued

```
                    20                  25                  30
Leu Pro Pro Lys Ile Pro Gly Gly Trp Pro Val Ile Gly His Leu Phe
                35                  40                  45
His Phe Asn Asp Asp Gly Asp Asp Arg Pro Leu Ala Arg Lys Leu Gly
            50                  55                  60
Asp Leu Ala Asp Lys Tyr Gly Pro Val Phe Thr Phe Arg Leu Gly Leu
 65                  70                  75                  80
Pro Leu Val Leu Val Ser Ser Tyr Glu Ala Val Lys Asp Cys Phe
                85                  90                  95
Ser Thr Asn Asp Ala Ile Phe Ser Asn Arg Pro Ala Phe Leu Tyr Gly
                100                 105                 110
Asp Tyr Leu Gly Tyr Asn Asn Ala Met Leu Phe Leu Ala Asn Tyr Gly
            115                 120                 125
Pro Tyr Trp Arg Lys Asn Arg Lys Leu Val Ile Gln Glu Val Leu Ser
        130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Lys Lys Ala Phe Lys Asp Phe Met Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Gly Glu Gly Tyr Ser Arg
    290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
                325                 330                 335
Asn Gln Lys Ala Leu Thr Lys Ala Gln Glu Glu Ile Asp Thr Lys Val
            340                 345                 350
Gly Lys Asp Arg Trp Val Glu Ser Asp Ile Lys Asp Leu Val Tyr
        355                 360                 365
Leu Gln Ala Ile Val Lys Glu Val Leu Arg Leu Tyr Pro Pro Gly Pro
    370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
        435                 440                 445
```

```
Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 26
<211> LENGTH: 517
<212> TYPE: PRT
<213> ORGANISM: Nicotiana tabacum

<400> SEQUENCE: 26

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
```

```
            290                 295                 300
Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
                340                 345                 350

Gly Lys Asp Arg Trp Val Glu Glu Ser Asp Ile Lys Asp Leu Val Tyr
                355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Leu
                405                 410                 415

Arg Asp Pro Lys Leu Trp Pro Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
                450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
                515

<210> SEQ ID NO 27
<211> LENGTH: 517
<212> TYPE: PRT
<213> ORGANISM: Nicotiana tabacum

<400> SEQUENCE: 27

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140
```

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Glu Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
                340                 345                 350

Cys Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
        435                 440                 445

Pro Phe Gly Pro Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515

<210> SEQ ID NO 28
<211> LENGTH: 517
<212> TYPE: PRT
<213> ORGANISM: Nicotiana tabacum

<400> SEQUENCE: 28

```
Met Val Phe Pro Ile Glu Ala Ile Val Gly Leu Val Thr Phe Thr Phe
1               5                   10                  15

Leu Phe Tyr Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asn Asp Arg Pro Leu Ala Arg Lys Leu Gly
        50                  55                  60

Asp Leu Ala Asp Lys Tyr Gly Pro Val Phe Thr Phe Arg Leu Gly Leu
65                      70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
        130                 135                 140

Ala Ser Arg Leu Lys Lys Phe Lys His Val Arg Phe Ala Arg Ile Gln
145                 150                 155                 160

Thr Ser Ile Lys Asn Leu Tyr Thr Arg Ile Asp Arg Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Ile Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Asn Ala Leu Lys Lys Ala Gln Glu Glu Ile Asp Thr Ile Val
            340                 345                 350

Gly Lys Asp Arg Trp Val Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Ile Glu Asp Cys Val Val Ser Gly Tyr
385                 390                 395                 400

Tyr Ile Ser Lys Gly Thr Arg Leu Phe Ala Asn Val Met Lys Leu Gln
                405                 410                 415
```

Arg Asp Pro Lys Leu Trp Pro Asn Pro Asp Asn Phe Asp Pro Glu Arg
            420                 425                 430

Phe Val Ala Ala Gly Ile Asp Phe Arg Gly Gln His Tyr Glu Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Ser Thr Pro Asn Asp Glu Pro Leu Asp Met Lys Glu Gly Ala Gly Ile
                485                 490                 495

Thr Ile Arg Lys Val Asn Pro Val Glu Val Ile Ile Met Pro Arg Leu
                500                 505                 510

Ala Pro Glu Leu Tyr
            515

<210> SEQ ID NO 29
<211> LENGTH: 518
<212> TYPE: PRT
<213> ORGANISM: Nicotiana tabacum

<400> SEQUENCE: 29

Met Val Phe Pro Val Glu Ala Ile Val Gly Leu Val Thr Phe Thr Phe
1               5                   10                  15

Leu Phe Tyr Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Ile Lys Asp Cys Phe
            85                  90                  95

Ser Thr Asn Asp Ala Ile Phe Ser Asn Arg Pro Ala Phe Leu Tyr Gly
            100                 105                 110

Glu Tyr Leu Gly Tyr Lys Asn Ala Met Leu Phe Leu Ala Asn Tyr Gly
            115                 120                 125

Ser Tyr Trp Arg Lys Asn Arg Lys Leu Ile Ile Gln Glu Val Leu Ser
            130                 135                 140

Ala Ser Arg Leu Glu Lys Phe Lys His Val Arg Phe Ala Arg Ile Gln
145                 150                 155                 160

Thr Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Lys Lys Arg Glu
            260                 265                 270

```
Lys Ile Met Glu Val Gly Thr Glu Gly Asn Glu Gln Asp Phe Ile Asp
            275                 280                 285

Val Val Leu Ser Lys Met Ser Asn Glu Tyr Leu Gly Glu Gly Tyr Ser
        290                 295                 300

Arg Asp Thr Val Ile Lys Ala Thr Val Phe Ser Leu Val Leu Asp Ala
305                 310                 315                 320

Ala Asp Thr Val Ala Leu His Ile Asn Cys Gly Met Ala Leu Leu Ile
                325                 330                 335

Asn Asn Gln Asn Ala Leu Lys Lys Ala Gln Glu Glu Ile Asp Thr Lys
                340                 345                 350

Val Gly Lys Asp Arg Trp Val Glu Glu Ser Asp Ile Lys Asp Leu Val
            355                 360                 365

Tyr Leu Gln Ala Ile Val Lys Glu Val Leu Arg Leu Tyr Pro Pro Gly
        370                 375                 380

Pro Leu Leu Val Pro His Glu Asn Val Glu Asp Cys Val Val Ser Gly
385                 390                 395                 400

Tyr His Ile Pro Lys Gly Thr Arg Leu Phe Ala Asn Val Met Lys Leu
                405                 410                 415

Gln Arg Asp Pro Lys Leu Trp Ser Asn Pro Asp Lys Phe Asn Pro Glu
                420                 425                 430

Arg Phe Ile Ala Arg Asp Ile Asp Phe His Gly Gln His Tyr Glu Tyr
            435                 440                 445

Ile Pro Phe Gly Ser Gly Arg Arg Ser Cys Pro Gly Met Thr Tyr Ala
        450                 455                 460

Leu Gln Val Glu His Leu Thr Met Ala His Leu Ile Gln Gly Phe Asn
465                 470                 475                 480

Tyr Arg Thr Pro Thr Asp Glu Pro Leu Asp Met Lys Glu Gly Ala Gly
                485                 490                 495

Ile Thr Ile Arg Lys Val Asn Pro Val Lys Val Ile Thr Pro Arg
            500                 505                 510

Leu Ala Pro Glu Leu Tyr
        515

<210> SEQ ID NO 30
<211> LENGTH: 517
<212> TYPE: PRT
<213> ORGANISM: Nicotiana tabacum

<400> SEQUENCE: 30

Met Val Phe Pro Ile Glu Ala Phe Val Gly Leu Val Thr Phe Thr Phe
1               5                   10                  15

Leu Leu Tyr Phe Leu Trp Thr Lys Lys Ser Gln Lys Leu Pro Lys Pro
                20                  25                  30

Leu Pro Pro Lys Ile Pro Gly Gly Trp Pro Val Ile Gly His Leu Phe
            35                  40                  45

His Phe Asn Asn Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Thr Met Leu Phe Leu Ala Asn Tyr Gly
```

115                 120                 125
Pro Tyr Trp Arg Lys Asn Arg Lys Leu Val Ile Gln Glu Val Leu Ser
    130                 135                 140

Ala Ser Arg Leu Glu Lys Phe Lys Gln Val Arg Phe Thr Arg Ile Gln
145                 150                 155                 160

Thr Ser Ile Lys Asn Leu Tyr Thr Arg Ile Asn Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Asn Ala Phe Lys Asp Phe Met Val Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Ile Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Gly Ala Glu Gly Asn Glu Gln Asp Phe Ile Asp Val
        275                 280                 285

Val Leu Ser Lys Leu Ser Lys Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Thr Leu Leu Ile Asn
                325                 330                 335

Asn Gln Asn Ala Leu Met Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Lys Val Leu Arg Leu Tyr Pro Pro Gly Pro
    370                 375                 380

Leu Leu Val Pro His Glu Asn Val Lys Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Leu Ser Asn Pro Asp Lys Phe Asp Pro Glu Arg
            420                 425                 430

Phe Ile Ala Gly Asp Ile Asp Phe Arg Gly His His Tyr Glu Phe Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Lys Thr Pro Asn Asp Glu Ala Leu Asp Met Lys Glu Gly Ala Gly Ile
                485                 490                 495

Thr Ile Arg Lys Val Asn Pro Val Glu Leu Ile Ile Thr Pro Arg Leu
            500                 505                 510

Ala Pro Glu Leu Tyr
        515

<210> SEQ ID NO 31

```
<211> LENGTH: 517
<212> TYPE: PRT
<213> ORGANISM: Nicotiana tabacum

<400> SEQUENCE: 31

Met Leu Ser Pro Ile Glu Ala Phe Val Gly Leu Val Thr Phe Thr Phe
1               5                   10                  15

Leu Leu Tyr Phe Leu Trp Thr Lys Lys Ser Gln Lys Leu Pro Lys Pro
            20                  25                  30

Leu Pro Pro Lys Ile Pro Gly Gly Trp Pro Val Ile Gly His Leu Phe
        35                  40                  45

His Phe Asn Asn Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Leu Leu Tyr Gly
            100                 105                 110

Glu Tyr Leu Gly Tyr Asn Asn Thr Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys Gln Val Arg Phe Thr Arg Ile Gln
145                 150                 155                 160

Thr Ser Ile Lys Asn Leu Tyr Thr Arg Ile Asn Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Asn Ala Phe Lys Asp Phe Met Val Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Ile Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Ile Glu Val Gly Ala Glu Gly Asn Glu Gln Asp Phe Ile Asp Val
        275                 280                 285

Val Leu Ser Lys Leu Ser Lys Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Thr Leu Leu Ile Asn
                325                 330                 335

Asn Gln Asn Ala Leu Met Lys Ala Gln Glu Glu Ile Asp Thr Lys Val
            340                 345                 350

Gly Lys Asp Arg Trp Val Glu Ser Asp Ile Lys Asp Leu Val Tyr
        355                 360                 365

Leu Gln Ala Ile Val Lys Lys Val Leu Arg Leu Tyr Pro Pro Gly Pro
    370                 375                 380

Leu Leu Val Pro His Glu Asn Val Lys Asp Cys Val Val Ser Gly Tyr
```

```
                385                 390                 395                 400
His Ile Pro Lys Gly Thr Arg Leu Phe Ala Asn Val Met Lys Leu Gln
                405                 410                 415

Arg Asp Pro Lys Leu Leu Ser Asn Pro Asp Lys Phe Asp Pro Glu Arg
                420                 425                 430

Phe Ile Ala Gly Asp Ile Asp Phe Arg Gly His His Tyr Glu Phe Ile
                435                 440                 445

Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Lys Thr Pro Asn Asp Glu Ala Leu Asp Met Lys Glu Gly Ala Gly Ile
                485                 490                 495

Thr Ile Arg Lys Val Asn Pro Val Glu Leu Ile Ile Thr Pro Arg Leu
                500                 505                 510

Ala Pro Glu Leu Tyr
        515

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggaattatg cccatcctac a                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cattagtggt tgcacctgag g                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatgagatgt gtgcatactt g                                              21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccaaattaga aaaactcgta ctg                                            23
```

```
<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
attgtaggac tagtaaccct tacac                                             25

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaggcacaaa gaattctcat c                                                 21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagtagaggg attgtttccg                                                   20

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtacaatcaa gataaaacat ctaagg                                            26

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cggtgaatac cttggctaca g                                                 21

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aattgtcact tctacaggat ttact                                             25

<210> SEQ ID NO 42
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atggtttttc cggtagaa                                                       18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttaataaagc tcaggtgc                                                       18

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acgtgatcct aaactctggt ctg                                                 23

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcctgcacct tccttcatg                                                      19

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggatgactt atgcattaca agc                                                 23

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aattgtcact tctacaggat ttact                                               25

<210> SEQ ID NO 48
<211> LENGTH: 20
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ggtgtccaca gacttcgtgg					20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gactcctcac agcagcacca					20

<210> SEQ ID NO 50
<211> LENGTH: 1733
<212> TYPE: DNA
<213> ORGANISM: Nicotiana sp.
<220> FEATURE:
<221> NAME/KEY: CDS
<222> LOCATION: (1)...(1551)

<400> SEQUENCE: 50

| atg | ctt | tct | ccc | ata | gaa | gcc | att | gta | gga | cta | gta | acc | ttc | aca | ttt | 48 |
| Met | Leu | Ser | Pro | Ile | Glu | Ala | Ile | Val | Gly | Leu | Val | Thr | Phe | Thr | Phe | |
| 1 | | | | 5 | | | | | 10 | | | | | 15 | | |

| ctc | ttc | ttc | ttc | cta | tgg | aca | aaa | aaa | tct | caa | aaa | cct | tca | aaa | ccc | 96 |
| Leu | Phe | Phe | Phe | Leu | Trp | Thr | Lys | Lys | Ser | Gln | Lys | Pro | Ser | Lys | Pro | |
| | | | 20 | | | | | 25 | | | | | 30 | | | |

| tta | cca | ccg | aaa | atc | ccc | gga | gga | tgg | ccg | gta | atc | ggc | cat | ctt | ttc | 144 |
| Leu | Pro | Pro | Lys | Ile | Pro | Gly | Gly | Trp | Pro | Val | Ile | Gly | His | Leu | Phe | |
| | | 35 | | | | | 40 | | | | | 45 | | | | |

| cac | ttc | aat | gac | gac | ggc | gac | gac | cgt | cca | tta | gct | cga | aaa | ctc | gga | 192 |
| His | Phe | Asn | Asp | Asp | Gly | Asp | Asp | Arg | Pro | Leu | Ala | Arg | Lys | Leu | Gly | |
| | 50 | | | | | 55 | | | | | 60 | | | | | |

| gac | tta | gct | gac | aaa | tac | ggc | ccc | gtt | ttc | act | ttt | cgg | cta | ggc | ctt | 240 |
| Asp | Leu | Ala | Asp | Lys | Tyr | Gly | Pro | Val | Phe | Thr | Phe | Arg | Leu | Gly | Leu | |
| 65 | | | | | 70 | | | | | 75 | | | | | 80 | |

| ccc | ctt | gtc | tta | gtt | gta | agc | agt | tac | gaa | gct | gta | aaa | gac | tgt | ttc | 288 |
| Pro | Leu | Val | Leu | Val | Val | Ser | Ser | Tyr | Glu | Ala | Val | Lys | Asp | Cys | Phe | |
| | | | | 85 | | | | | 90 | | | | | 95 | | |

| tct | aca | aat | gac | gcc | att | ttt | tcc | aat | cgt | cca | gct | ttt | ctt | tac | ggc | 336 |
| Ser | Thr | Asn | Asp | Ala | Ile | Phe | Ser | Asn | Arg | Pro | Ala | Phe | Leu | Tyr | Gly | |
| | | | 100 | | | | | 105 | | | | | 110 | | | |

| gat | tac | ctt | ggc | tac | aat | aat | gcc | atg | cta | ttt | ttg | gcc | aat | tac | gga | 384 |
| Asp | Tyr | Leu | Gly | Tyr | Asn | Asn | Ala | Met | Leu | Phe | Leu | Ala | Asn | Tyr | Gly | |
| | | 115 | | | | | 120 | | | | | 125 | | | | |

| cct | tac | tgg | cga | aaa | aat | cga | aaa | tta | gtt | att | cag | gaa | gtt | ctc | tcc | 432 |
| Pro | Tyr | Trp | Arg | Lys | Asn | Arg | Lys | Leu | Val | Ile | Gln | Glu | Val | Leu | Ser | |
| | 130 | | | | | 135 | | | | | 140 | | | | | |

| gct | agt | cgt | ctc | gaa | aaa | ttc | aaa | cac | gtg | aga | ttt | gca | aga | att | caa | 480 |
| Ala | Ser | Arg | Leu | Glu | Lys | Phe | Lys | His | Val | Arg | Phe | Ala | Arg | Ile | Gln | |
| 145 | | | | | 150 | | | | | 155 | | | | | 160 | |

| gcg | agc | att | aag | aat | tta | tat | act | cga | att | gat | gga | aat | tcg | agt | acg | 528 |
| Ala | Ser | Ile | Lys | Asn | Leu | Tyr | Thr | Arg | Ile | Asp | Gly | Asn | Ser | Ser | Thr | |
| | | | | 165 | | | | | 170 | | | | | 175 | | |

| ata | aat | tta | act | gat | tgg | tta | gaa | gaa | ttg | aat | ttt | ggt | ctg | atc | gtg | 576 |

```
Ile Asn Leu Thr Asp Trp Leu Glu Glu Leu Asn Phe Gly Leu Ile Val
            180                 185                 190 aag atg atc gct gga aaa aat tat gaa tcc ggt aaa gga gat gaa caa      624
Lys Met Ile Ala Gly Lys Asn Tyr Glu Ser Gly Lys Gly Asp Glu Gln
            195                 200                 205 gtg gag aga ttt aag aaa gcg ttt aag gat ttt atg att tta tca atg      672
Val Glu Arg Phe Lys Lys Ala Phe Lys Asp Phe Met Ile Leu Ser Met
210                 215                 220 gag ttt gtg tta tgg gat gca ttt cca att cca tta ttt aaa tgg gtg      720
Glu Phe Val Leu Trp Asp Ala Phe Pro Ile Pro Leu Phe Lys Trp Val
225                 230                 235                 240 gat ttt caa ggg cat gtt aag gct atg aaa agg act ttt aaa gat ata      768
Asp Phe Gln Gly His Val Lys Ala Met Lys Arg Thr Phe Lys Asp Ile
            245                 250                 255 gat tct gtt ttt cag aat tgg tta gag gaa cat att aat aaa aga gaa      816
Asp Ser Val Phe Gln Asn Trp Leu Glu Glu His Ile Asn Lys Arg Glu
                260                 265                 270 aaa atg gag gtt aat gca gaa ggg aat gaa caa gat ttc att gat gtg      864
Lys Met Glu Val Asn Ala Glu Gly Asn Glu Gln Asp Phe Ile Asp Val
            275                 280                 285 gtg ctt tca aaa atg agt aat gaa tat ctt ggt gaa ggt tac tct cgt      912
Val Leu Ser Lys Met Ser Asn Glu Tyr Leu Gly Glu Gly Tyr Ser Arg
        290                 295                 300 gat act gtc att aaa gca acg gtg ttt agt ttg gtc ttg gat gca gca      960
Asp Thr Val Ile Lys Ala Thr Val Phe Ser Leu Val Leu Asp Ala Ala
305                 310                 315                 320 gac aca gtt gct ctt cac ata aat tgg gga atg gca tta ttg ata aac     1008
Asp Thr Val Ala Leu His Ile Asn Trp Gly Met Ala Leu Leu Ile Asn
                325                 330                 335 aat caa aag gcc ttg acg aaa gca caa gaa gag ata gac aca aaa gtt     1056
Asn Gln Lys Ala Leu Thr Lys Ala Gln Glu Glu Ile Asp Thr Lys Val
            340                 345                 350 ggt aag gac aga tgg gta gaa gag agt gat att aag gat ttg gta tac     1104
Gly Lys Asp Arg Trp Val Glu Glu Ser Asp Ile Lys Asp Leu Val Tyr
        355                 360                 365 ctc caa gct att gtt aaa gaa gtg tta cga tta tat cca cca gga cct     1152
Leu Gln Ala Ile Val Lys Glu Val Leu Arg Leu Tyr Pro Pro Gly Pro
370                 375                 380 ttg tta gta cca cac gaa aat gta gaa gat tgt gtt gtt agt gga tat     1200
Leu Leu Val Pro His Glu Asn Val Glu Asp Cys Val Val Ser Gly Tyr
385                 390                 395                 400 cac att cct aaa ggg aca aga tta ttc gca aac gtc atg aaa ctg caa     1248
His Ile Pro Lys Gly Thr Arg Leu Phe Ala Asn Val Met Lys Leu Gln
                405                 410                 415 cgt gat cct aaa ctc tgg tct gat cct gat act ttc gat cca gag aga     1296
Arg Asp Pro Lys Leu Trp Ser Asp Pro Asp Thr Phe Asp Pro Glu Arg
            420                 425                 430 ttc att gct act gat att gac ttt cgt ggt cag tac tat aag tat atc     1344
Phe Ile Ala Thr Asp Ile Asp Phe Arg Gly Gln Tyr Tyr Lys Tyr Ile
        435                 440                 445 ccg ttt ggt tct gga aga cga tct tgt cca ggg atg act tat gca ttg     1392
Pro Phe Gly Ser Gly Arg Arg Ser Cys Pro Gly Met Thr Tyr Ala Leu
450                 455                 460 caa gtg gaa cac tta aca atg gca cat ttg atc caa ggt ttc aat tac     1440
Gln Val Glu His Leu Thr Met Ala His Leu Ile Gln Gly Phe Asn Tyr
465                 470                 475                 480 aga act cca aat gac gag ccc ttg gat atg aag gaa ggt gca ggc ata     1488
Arg Thr Pro Asn Asp Glu Pro Leu Asp Met Lys Glu Gly Ala Gly Ile
                485                 490                 495
```

-continued

```
act ata cgt aag gta aat cct gtg gaa ctg ata ata gcg cct cgc ctg      1536
Thr Ile Arg Lys Val Asn Pro Val Glu Leu Ile Ile Ala Pro Arg Leu
            500                 505                 510 gca cct gag ctt tat taaaacctaa gatctttcat cttggttgat cattgtataa       1591
Ala Pro Glu Leu Tyr
        515 tactcctaaa tggatattca tttacctttt atcaattaat tgtcagtacg agtttttcta     1651 atttggtaca tttgtaataa taagtaaaga ataattgtgc taatatataa aggtttgtag     1711 aagataattg actgattgtc cc                                              1733
```